US012577213B2

(12) United States Patent
Liu et al.

(10) Patent No.: US 12,577,213 B2
(45) Date of Patent: Mar. 17, 2026

(54) DEUTERATED 1,4-BENZODIAZEPINE-2,5-DIONE COMPOUND AND USE THEREOF

(71) Applicant: NINGBO COMBIREG PHARMACEUTICAL TECHNOLOGY CO., LTD., Zhejiang (CN)

(72) Inventors: Gang Liu, Zhejiang (CN); Yao Ma, Zhejiang (CN); Wenjun Yu, Zhejiang (CN)

(73) Assignee: NINGBO COMBIREG PHARMACEUTICAL TECHNOLOGY CO., LTD., Zhejiang (CN)

( * ) Notice: Subject to any disclaimer, the term of this patent is extended or adjusted under 35 U.S.C. 154(b) by 421 days.

(21) Appl. No.: 18/252,039

(22) PCT Filed: Oct. 25, 2021

(86) PCT No.: PCT/CN2021/125995
§ 371 (c)(1),
(2) Date: May 7, 2023

(87) PCT Pub. No.: WO2022/105542
PCT Pub. Date: May 27, 2022

(65) Prior Publication Data

US 2024/0002353 A1 Jan. 4, 2024

(30) Foreign Application Priority Data

Nov. 17, 2020 (CN) ........................ 202011287532.X

(51) Int. Cl.
*C07D 243/14* (2006.01)
*A61P 35/00* (2006.01)

(52) U.S. Cl.
CPC ............ *C07D 243/14* (2013.01); *A61P 35/00* (2018.01); *C07B 2200/05* (2013.01)

(58) Field of Classification Search
CPC ..... C07D 243/14; C07D 243/08; A61P 35/00; A61P 35/02; C07B 2200/05; C07B 59/002
See application file for complete search history.

(56) References Cited

FOREIGN PATENT DOCUMENTS

| | | | | |
|---|---|---|---|---|
| CN | 105693634 A | * | 6/2016 | ........... C07D 403/12 |
| CN | 106831614 A | | 6/2017 | |
| WO | 95/26325 A2 | | 10/1995 | |

OTHER PUBLICATIONS

Jan. 25, 2022 International Search Report issued in International Patent Application No. PCT/CN2021/125995.
Jan. 25, 2022 Written Opinion of the International Searching Authority issued in International Patent Application No. PCT/CN2021/125995.
Mar. 15, 2023 Chinese Office Action issued in Chinese Patent Application No. 2021112388357.
Yan, Fang et al. Pharmacokinetic Advantage and Clinical Development of Deuterated Drugs, The Chinese Journal of Clinical Pharmacology vol. 36, No. 16, Aug. 31, 2020 pp. 2558-2563.
May 7, 2024 the First Examination report issued in Japanese Patent Application No. 2023-530560.
Nov. 5, 2024 the Second Examination report issued in Japanese Patent Application No. 2023-530560.
Jun. 12, 2024 the First Examination report issued in Canadian Patent Application No. 3, 199, 129.
Sep. 11, 2024 extended European Search Report issued in European Patent Application No. 21893690.4.
Roger Tung, The Development of Deuterium-Containing Drugs, Mar. 1, 2010, pp. 24-26, 28, XP009148260.
Liming Shao, et al., The kinetic isotope effect in the search for deuterated drugs, vol. 23, No. 6, Jan. 1, 2010, pp. 398-404, XP009139025.
Wako Organic Square, 2010, No. 33, pp. 2-3.
Oct. 19, 2023 the First Examination report issued in Australian Patent Application No. 2021382771.
Aug. 8, 2025 the Second Office Action issued in Canadian Patent Application No. 3,199,129.

* cited by examiner

*Primary Examiner* — Kamal A Saeed
*Assistant Examiner* — Meghan C Heasley
(74) *Attorney, Agent, or Firm* — Houston Beshining Law Office PLLC; Liangang Ye

(57) ABSTRACT

Disclosed are a deuterated 1,4-benzodiazepine-2,5-dione compound and the use thereof. Provided is a compound as represented by formula I or a pharmaceutically acceptable salt thereof. The disclosed 1,4-benzodiazepine-2,5-dione active compound maintains the activity of inhibiting tumor cells and tumor stem cells, and prolongs the degradation function of in-vitro human liver microsomes on the compound, such that the half-life period is significantly prolonged, which provides a safer and more reliable candidate for developing new anti-tumor drugs.

16 Claims, 1 Drawing Sheet

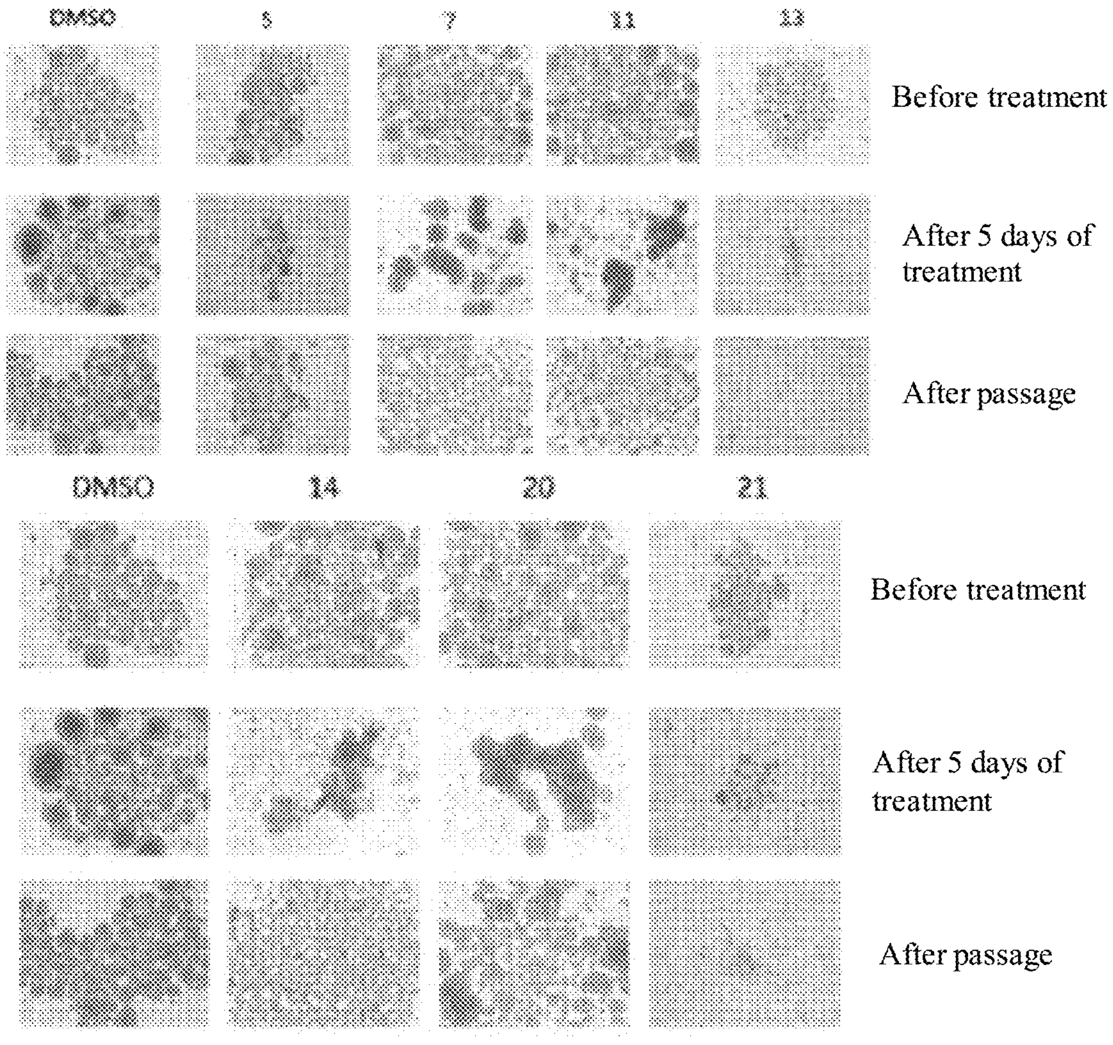
DMSO
5
7
11
13
Before treatment
After 5 days of treatment
After passage
DMSO
14
20
21
Before treatment
After 5 days of treatment
After passage

DEUTERATED 1,4-BENZODIAZEPINE-2,5-DIONE COMPOUND AND USE THEREOF

The present application is a National Stage of International Application No. PCT/CN2021/125995, filed on Oct. 25, 2021, which claims the priorities of the Chinese Patent Application NO. CN202011287532.X filed on Nov. 17, 2020. The contents of the Chinese patent application are incorporated herein by reference in their entireties.

TECHNICAL FIELD

The present disclosure relates to a class of deuterated 1,4-benzodiazepine-2,5-dione compounds and their use in the treatment of proliferative diseases, especially cancer.

BACKGROUND

Isotopes, which are different atoms of the same chemical element, have different masses due to the presence of different numbers of neutrons in the nucleus. Based on physical properties, isotopes can be classified into two forms: radioactivity and stability. There are three isotopes of hydrogen in nature: protium (1H, H), deuterium (2H, D) and tritium (3H, T). Among them, deuterium is a stable non-radioactive isotope with a content of 0.015% in nature. There are two main ways to introduce deuterium into compounds: one is proton exchange with hydrogen, and the other is synthesis using deuterated raw materials. Currently, the second method is more commonly used. Since the deuterium content in the synthesized deuterated compound is much higher than that of 0.015% in nature, it is regarded as a new compound.

The 1,4-benzodiazepine-2,5-dione compounds disclosed in the granted patent NO. ZL201610154581.3 can not only inhibit the growth of 60 human tumor cell lines, but also inhibit the self-renewal ability of tumor stem cells, which may provide a new class of anti-tumor drugs to completely eliminate tumors and tumor stem cells. However, its metabolic stability and anti-tumor pharmacodynamics need to be further improved.

Content of the Present Invention

The technical problem to be solved by the present disclosure is to provide a deuterated 1,4-benzodiazepine-2,5-dione compound and a use thereof in response to the short half-life and other defects of the 1,4-benzodiazepine-2,5-dione compound in the prior arts. The 1,4-benzodiazepine-2,5-dione active compound of the present disclosure maintains the activity of inhibiting tumor cells and tumor stem cells, and prolongs the degradation function of human liver microsomes on the compound in vitro, such that the half-life is significantly prolonged, which provides a safer and more reliable candidate for developing new anti-tumor drugs.

The present disclosure solves the above-mentioned technical problem through the following technical solutions.

The present disclosure provides a compound represented by formula I or a pharmaceutically acceptable salt thereof,

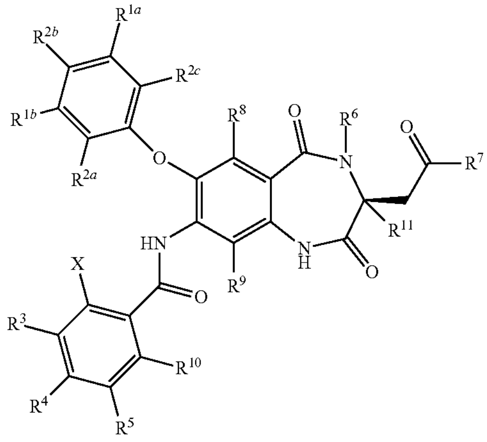

I wherein, X is hydrogen, fluorine, chlorine, bromine or iodine;

$R^{1a}$ and $R^{1b}$ are independently hydrogen, deuterium, $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl, $C_{2-4}$ alkenyl, $C_{2-4}$ alkynyl or deuterated $C_{1-3}$ alkyl;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently $C_{1-3}$ alkyl, deuterated $C_{1-3}$ alkyl or deuterated $C_{1-3}$ alkyl-O—; $R^{15}$ and $R^{16}$ are independently H, $C_{1-3}$ alkyl or deuterated $C_{1-3}$ alkyl;

$R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—;

or, $R^{13}$ and $R^{14}$ together with the attached nitrogen atom form: a 4- to 6-membered aliphatic heterocycle or a 4- to 6-membered aliphatic heterocycle substituted by one or more $R^{19}$; the 4- to 6-membered aliphatic heterocycle in the 4- to 6-membered aliphatic heterocycle and the 4- to 6-membered aliphatic heterocycle substituted by one or more $R^{19}$ contains 0-2 heteroatoms selected from N, O or S, besides the 1 shown N attached to the shown carbonyl;

$R^{19}$ is halogen, O═, $C_{1-3}$ alkyl or deuterated $C_{1-3}$ alkyl;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group.

In some preferred embodiments of the present disclosure, some groups in the compound represented by formula I or the pharmaceutically acceptable salt thereof are defined as follows (the groups not mentioned are the same as those described in any solution of the present disclosure), X is chlorine or bromine; such as bromine.

In some preferred embodiments of the present disclosure, some groups in the compound represented by formula I or the pharmaceutically acceptable salt thereof are defined as follows (the groups not mentioned are the same as those described in any solution of the present disclosure), $R^{1a}$ and $R^{1b}$ are the same.

In some preferred embodiments of the present disclosure, some groups in the compound represented by formula I or the pharmaceutically acceptable salt thereof are defined as follows (the groups not mentioned are the same as those described in any solution of the present disclosure), $R^{1a}$ and $R^{1b}$ are independently $C_{1-3}$ alkyl (such as methyl) or deuterated $C_{1-3}$ alkyl (such as $CD_3$); such as $C_{1-3}$ alkyl.

In some preferred embodiments of the present disclosure, some groups in the compound represented by formula I or the pharmaceutically acceptable salt thereof are defined as follows (the groups not mentioned are the same as those described in any solution of the present disclosure), $R^{2a}$, $R^{2b}$ and $R^{2c}$ are the same.

In some preferred embodiments of the present disclosure, some groups in the compound represented by formula I or the pharmaceutically acceptable salt thereof are defined as follows (the groups not mentioned are the same as those described in any solution of the present disclosure), $R^{2a}$, $R^{2b}$ and $R^{2c}$ are independently hydrogen.

In some preferred embodiments of the present disclosure, some groups in the compound represented by formula I or the pharmaceutically acceptable salt thereof are defined as follows (the groups not mentioned are the same as those described in any solution of the present disclosure), Any two or three of $R^3$, $R^4$ and $R^5$ are the same; for example, $R^3$, $R^4$ and $R^5$ are the same.

In some preferred embodiments of the present disclosure, some groups in the compound represented by formula I or the pharmaceutically acceptable salt thereof are defined as follows (the groups not mentioned are the same as those described in any solution of the present disclosure), $R^3$, $R^4$ and $R^5$ are independently $C_{1-3}$ alkyl-O— (such as methyl-O—), deuterated $C_{1-3}$ alkyl (such as $CD_3$ or $-CD_2-CD_3$) or deuterated $C_{1-3}$ alkyl-O— (such as $CD_3$-O—);

for example, $R^4$ is $C_{1-3}$ alkyl-O—, deuterated $C_{1-3}$ alkyl or deuterated $C_{1-3}$ alkyl-O—; which can be methyl-O—, $CD_3$ or $CD_3$-O—;

$R^3$ and $R^5$ are independently $C_{1-3}$ alkyl-O— or deuterated $C_{1-3}$ alkyl-O—; which can be methyl-O— or $CD_3$-O—.

For example, $R^3$, $R^4$ and $R^5$ are independently $C_{1-3}$ alkyl-O— or deuterated $C_{1-3}$ alkyl-O—; which can be deuterated $C_{1-3}$ alkyl-O—.

In some preferred embodiments of the present disclosure, some groups in the compound represented by formula I or the pharmaceutically acceptable salt thereof are defined as follows (the groups not mentioned are the same as those described in any solution of the present disclosure), $R^6$ is H, $C_{1-3}$ alkyl (such as methyl), $C_{2-4}$ alkynyl or deuterated $C_{1-3}$ alkyl (such as $CD_3$); for example, H, $C_{1-3}$ alkyl or deuterated $C_{1-3}$ alkyl; for example, H or $C_{1-3}$ alkyl; for example, H.

In some preferred embodiments of the present disclosure, some groups in the compound represented by formula I or the pharmaceutically acceptable salt thereof are defined as follows (the groups not mentioned are the same as those described in any solution of the present disclosure), $R^7$ is $-OR^{12}$, $R^{12}$ is $C_{1-3}$ alkyl or deuterated $C_{1-3}$ alkyl; for example, deuterated $C_{1-3}$ alkyl, for example, $CD_3$.

In some preferred embodiments of the present disclosure, some groups in the compound represented by formula I or the pharmaceutically acceptable salt thereof are defined as follows (the groups not mentioned are the same as those described in any solution of the present disclosure), $R^7$ is $-NR^{13}R^{14}$; $R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—; for example, OH, methyl, ethyl, $CD_3$, $-CD_2-CD_3$ or $CD_3$-O—;

for example, $R^{13}$ is OH, $C_{1-3}$ alkyl (such as methyl or ethyl), deuterated $C_{1-3}$ alkyl (such as $CD_3$ or $-CD_2-CD_3$), $C_{1-3}$ alkyl-O— (such as methyl-O—) or deuterated $C_{1-3}$ alkyl-O— (such as $CD_3$-O—);

$R^{14}$ is $C_{1-3}$ alkyl or deuterated $C_{1-3}$ alkyl (such as $CD_3$ or $-CD_2-CD_3$);

for example, $R^{13}$ and $R^{14}$ are independently $C_{1-3}$ alkyl, which can be methyl.

In some preferred embodiments of the present disclosure, some groups in the compound represented by formula I or the pharmaceutically acceptable salt thereof are defined as follows (the groups not mentioned are the same as those described in any solution of the present disclosure), $R^7$ is $-NR^{13}R^{14}$; $R^{13}$ and $R^{14}$ together with the attached nitrogen atom form: a 4- to 6-membered aliphatic heterocycle or a 4- to 6-membered aliphatic heterocycle substituted by one or more $R^{19}$; for example, 4- to 6-membered heterocyclic alkyl or 4- to 6-membered heterocyclic alkyl substituted by one or more $R^{19}$; the 4- to 6-membered heterocyclic alkyl in the 4- to 6-membered heterocyclic alkyl and the 4- to 6-membered heterocyclic alkyl substituted by one or more $R^{19}$ contains 0-1 heteroatoms selected from N, O or S, besides the 1 shown N attached to the shown carbonyl; for example,

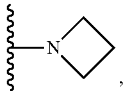,
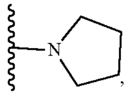,
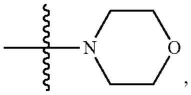,
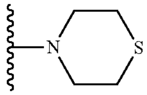,
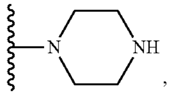,
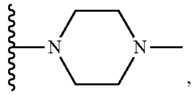,
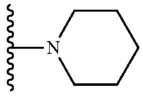,
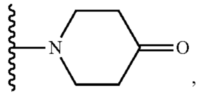,
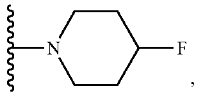,
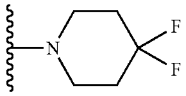 or
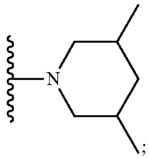;

for example,

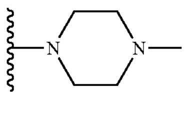 or 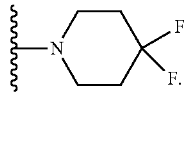.

In some preferred embodiments of the present disclosure, some groups in the compound represented by formula I or the pharmaceutically acceptable salt thereof are defined as follows (the groups not mentioned are the same as those described in any solution of the present disclosure), $R^7$ is $-C(R^{15}R^{16})-P(=O)(OR^{17}OR^{18})$;

$R^{15}$ and $R^{16}$ are independently $C_{1-3}$ alkyl; for example, methyl;

$R^{17}$ and $R^{11}$ are independently $C_{1-3}$ alkyl; for example, methyl.

In some preferred embodiments of the present disclosure, some groups in the compound represented by formula I or the pharmaceutically acceptable salt thereof are defined as follows (the groups not mentioned are the same as those described in any solution of the present disclosure), $R^{15}$ and $R^{16}$ are the same.

In some preferred embodiments of the present disclosure, some groups in the compound represented by formula I or the pharmaceutically acceptable salt thereof are defined as follows (the groups not mentioned are the same as those described in any solution of the present disclosure), $R^{17}$ and $R^{18}$ are the same.

In some preferred embodiments of the present disclosure, some groups in the compound represented by formula I or the pharmaceutically acceptable salt thereof are defined as follows (the groups not mentioned are the same as those described in any solution of the present disclosure), $R^{19}$ is halogen, O═, $C_{1-3}$ alkyl or deuterated $C_{1-3}$ alkyl; for example, halogen (such as F), O═ or $C_{1-3}$ alkyl (such as methyl); for example, F or methyl.

In some preferred embodiments of the present disclosure, some groups in the compound represented by formula I or the pharmaceutically acceptable salt thereof are defined as follows (the groups not mentioned are the same as those described in any solution of the present disclosure), $R^8$ is hydrogen.

In some preferred embodiments of the present disclosure, some groups in the compound represented by formula I or the pharmaceutically acceptable salt thereof are defined as follows (the groups not mentioned are the same as those described in any solution of the present disclosure), $R^9$ is hydrogen.

In some preferred embodiments of the present disclosure, some groups in the compound represented by formula I or the pharmaceutically acceptable salt thereof are defined as follows (the groups not mentioned are the same as those described in any solution of the present disclosure), $R^{10}$ is hydrogen.

In some preferred embodiments of the present disclosure, some groups in the compound represented by formula I or the pharmaceutically acceptable salt thereof are defined as follows (the groups not mentioned are the same as those described in any solution of the present disclosure), $R^{11}$ is hydrogen.

In some preferred embodiments of the present disclosure, some groups in the compound represented by formula I or the pharmaceutically acceptable salt thereof are defined as follows (the groups not mentioned are the same as those described in any solution of the present disclosure), $R^{1a}$ and $R^{1b}$ are independently $C_{1-3}$ alkyl;

$R^{2a}$, $R^{2b}$ and $R^{2c}$ are independently hydrogen;

for example, $R^{1a}$ and $R^{1b}$ are the same;

and/or, $R^{2a}$, $R^{2b}$ and $R^{2c}$ are the same.

In some preferred embodiments of the present disclosure, some groups in the compound represented by formula I or the pharmaceutically acceptable salt thereof are defined as follows (the groups not mentioned are the same as those described in any solution of the present disclosure), X is chlorine or bromine;

$R^4$ is $C_{1-3}$ alkyl-O—, deuterated $C_{1-3}$ alkyl or deuterated $C_{1-3}$ alkyl-O—;

$R^3$ and $R^5$ are independently $C_{1-3}$ alkyl-O— or deuterated $C_{1-3}$ alkyl-O—;

for example, $R^3$, $R^4$ and $R^5$ are independently $C_{1-3}$ alkyl-O— or deuterated $C_{1-3}$ alkyl-O—;

and/or, $R^3$, $R^4$ and $R^5$ are the same.

In some preferred embodiments of the present disclosure, some groups in the compound represented by formula I or the pharmaceutically acceptable salt thereof are defined as follows (the groups not mentioned are the same as those described in any solution of the present disclosure), $R^6$ is H; $R^7$ is —$OR^{12}$.

In some preferred embodiments of the present disclosure, some groups in the compound represented by formula I or the pharmaceutically acceptable salt thereof are defined as follows (the groups not mentioned are the same as those described in any solution of the present disclosure), $R^6$ is H; $R^7$ is —$C(R^{15}R^{16})$—P(═O)($OR^{17}OR^{18}$); for example, —$C(Me)_2P$(═O)$(OMe)_2$, —$CH_2$—P(═O)$(OMe)_2$.

In some preferred embodiments of the present disclosure, some groups in the compound represented by formula I or the pharmaceutically acceptable salt thereof are defined as follows (the groups not mentioned are the same as those described in any solution of the present disclosure), $R^6$ is H; $R^7$ is —$NR^{13}R^{14}$; $R^{13}$ and $R^{14}$ together with the attached nitrogen atom form: a 4- to 6-membered aliphatic heterocycle or a 4- to 6-membered aliphatic heterocycle substituted by one or more $R^{19}$; $R^{19}$ is halogen;

for example,

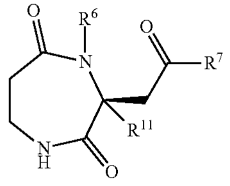

is

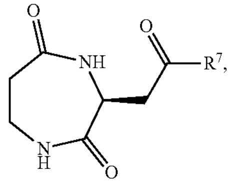

$R^7$ is

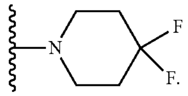 [SMILES: *N1CCC(F)(F)CC1]

In some preferred embodiments of the present disclosure, some groups in the compound represented by formula I or the pharmaceutically acceptable salt thereof are defined as follows (the groups not mentioned are the same as those described in any solution of the present disclosure), $R^6$ is H; $R^7$ is —$NR^{13}R^{14}$; $R^{13}$ is methyl, deuterated $C_{1-3}$ alkyl (such as $CD_3$ or —$CD_2$-$CD_3$), $C_{1-3}$ alkyl-O— (such as methyl-O—) or deuterated $C_{1-3}$ alkyl-O— (such as $CD_3$-O—);

$R^{14}$ is methyl or deuterated $C_{1-3}$ alkyl (such as $CD_3$ or —$CD_2$-$CD_3$);

for example,

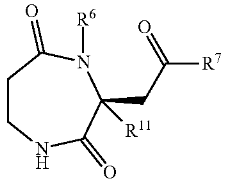

is

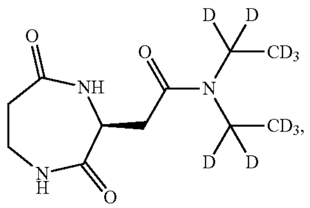

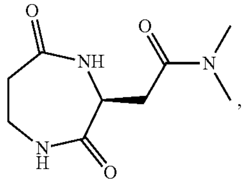

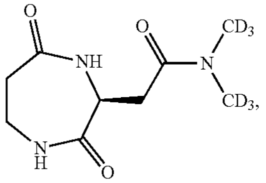

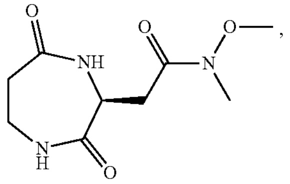

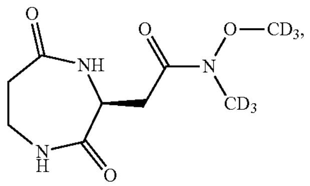

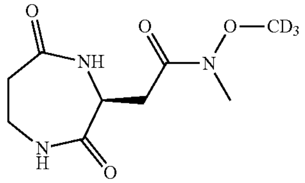

or

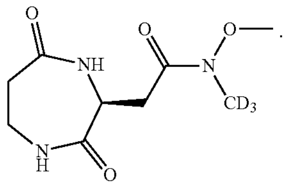

In some preferred embodiments of the present disclosure, some groups in the compound represented by formula I or the pharmaceutically acceptable salt thereof are defined as follows (the groups not mentioned are the same as those described in any solution of the present disclosure), $R^6$ is $C_{1-3}$ alkyl; $R^7$ is —$NR^{13}R^{14}$; $R^{13}$ is OH, $C_{1-3}$ alkyl (such as methyl), deuterated $C_{1-3}$ alkyl (such as $CD_3$) or deuterated $C_{1-3}$ alkyl-O— (such as $CD_3$-O—);

$R^{14}$ is $C_{1-3}$ alkyl (such as methyl) or deuterated $C_{1-3}$ alkyl (such as $CD_3$);

for example,

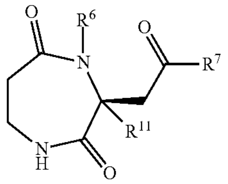

is

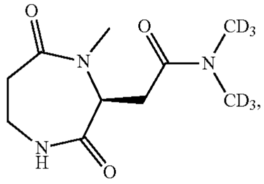

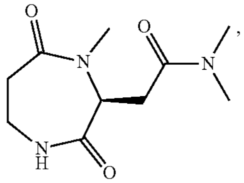

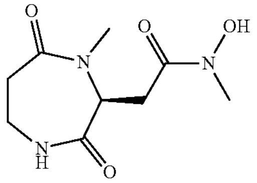

or

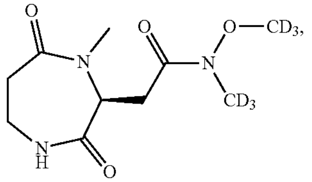

such as

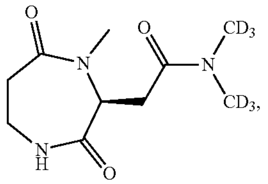

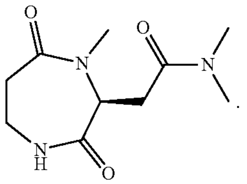

In some preferred embodiments of the present disclosure, some groups in the compound represented by formula I or the pharmaceutically acceptable salt thereof are defined as follows (the groups not mentioned are the same as those described in any solution of the present disclosure), at least one of $R^{1a}$, $R^{1b}$, $R^3$, $R^4$, $R^5$, $R^6$ and $R^7$ is deuterium or a deuterated group;

for example, at least one or a group of "$R^{1a}$ and $R^{1b}$", "$R^3$, $R^4$ and $R^5$", $R^6$ and $R^7$ is deuterium or a deuterated group;

for example, at least one or a group of "$R^{1a}$ and $R^{1b}$", "$R^3$, $R^4$ and $R^5$", $R^6$ and $R^7$ is deuterium or a deuterated group; and $R^{2a}$, $R^{2b}$ and $R^{2c}$ are independently hydrogen.

In some preferred embodiments of the present disclosure, some groups in the compound represented by formula I or the pharmaceutically acceptable salt thereof are defined as follows (the groups not mentioned are the same as those described in any solution of the present disclosure), at least one of $R^3$, $R^4$, $R^5$, $R^6$ and $R^7$ is deuterium or a deuterated group;

for example, at least one or a group of "$R^3$, $R^4$ and $R^5$", $R^6$ and $R^7$ is deuterium or a deuterated group;

for example, at least one or a group of "$R^3$, $R^4$ and $R^5$", $R^6$ and $R^7$ is deuterium or a deuterated group; and $R^{1a}$ and $R^{1b}$ are independently hydrogen or $C_{1-3}$ alkyl, and $R^{2a}$, $R^{2b}$ and $R^{2c}$ are independently hydrogen.

In some preferred embodiments of the present disclosure, some groups in the compound represented by formula I or the pharmaceutically acceptable salt thereof are defined as follows (the groups not mentioned are the same as those described in any solution of the present disclosure), one or two (groups) of "$R^3$, $R^4$ and $R^5$", $R^6$ and $R^7$ are deuterium or deuterated group;

for example, "$R^3$, $R^4$ and $R^5$" and/or $R^7$ are a deuterated group, $R^6$ and/or $R^7$ are deuterium or a deuterated group; the remaining groups in Formula I are not deuterium or deuterated groups.

In some preferred embodiments of the present disclosure, some groups in the compound represented by formula I or the pharmaceutically acceptable salt thereof are defined as follows (the groups not mentioned are the same as those described in any solution of the present disclosure), wherein, X is chlorine or bromine;

$R^{1a}$ and $R^{1b}$ are independently $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—; for example, $C_{1-3}$ alkyl-O—, deuterated $C_{1-3}$ alkyl or deuterated $C_{1-3}$ alkyl-O—;

$R^6$ is halogen, $C_{1-3}$ alkyl or deuterated $C_{1-3}$ alkyl;

$R^7$ is —$OR^{12}$, —$NR^{13}R^{14}$ or —$C(R^{15}R^{16})$—P(=O)($OR^{17}OR^{18}$), wherein $R^{12}$ is deuterated $C_{1-3}$ alkyl;

$R^{15}$ and $R^{16}$ are independently $C_{1-3}$ alkyl or deuterated $C_{1-3}$ alkyl; $R^{17}$ and $R^{18}$ are independently $C_{1-3}$ alkyl;

$R^{13}$ is OH, $C_{1-3}$ alkyl, deuterated $C_{1-3}$ alkyl, $C_{1-3}$ alkyl-O— or deuterated $C_{1-3}$ alkyl-O—; $R^{14}$ is $C_{1-3}$ alkyl or deuterated $C_{1-3}$ alkyl;

or, $R^{13}$ and $R^{14}$ together with the attached nitrogen atom form: a 4- to 6-membered aliphatic heterocycle or a 4- to 6-membered aliphatic heterocycle substituted by one or more $R^{19}$;

$R^{19}$ is halogen, O=, $C_{1-3}$ alkyl or deuterated $C_{1-3}$ alkyl; for example, halogen or $C_{1-3}$ alkyl;

$R^8$, $R^9$, $R^{10}$ and $R^{11}$ are hydrogen;

wherein, at least one of $R^{1a}$, $R^{1b}$, $R^3$, $R^4$, $R^5$, $R^6$ and $R^7$ is deuterium or a deuterated group;

for example, $R^{1a}$ and $R^{1b}$ are the same;

and/or, $R^{2a}$, $R^{2b}$ and $R^{2c}$ are the same;

and/or, $R^3$, $R^4$ and $R^5$ are the same.

In some preferred embodiments of the present disclosure, some groups in the compound represented by formula I or the pharmaceutically acceptable salt thereof are defined as follows (the groups not mentioned are the same as those described in any solution of the present disclosure), wherein, X is chlorine or bromine;

$R^{1a}$ and $R^{1b}$ are independently $C_{1-3}$ alkyl; and $R^{1a}$ and $R^{1b}$ are the same;

$R^{2a}$, $R^{2b}$ and $R^{2c}$ are independently hydrogen; and $R^{2a}$, $R^{2b}$ and $R^{2c}$ are the same;

$R^3$, $R^4$ and $R^5$ are independently $C_{1-3}$ alkyl-O— or deuterated $C_{1-3}$ alkyl-O—; and $R^3$, $R^4$ and $R^5$ are the same;

$R^6$ is H; $R^7$ is —$OR^{12}$, —$NR^{13}R^{14}$, or —$C(R^{15}R^{16})$—P(=O)($OR^{17}OR^{18}$); wherein $R^{12}$ is independently deuterated $C_{1-3}$ alkyl; $R^{15}$ and $R^{16}$ are independently $C_{1-3}$ alkyl; $R^{17}$ and $R^{18}$ are independently $C_{1-3}$ alkyl; $R^{13}$ is methyl, deuterated $C_{1-3}$ alkyl, $C_{1-3}$ alkyl-O— or deuterated $C_{1-3}$ alkyl-O—; $R^{14}$ is methyl or deuterated $C_{1-3}$ alkyl; or, $R^{13}$ and $R^{14}$ together with the attached nitrogen atom form: a 4- to 6-membered aliphatic heterocycle or a 4- to 6-membered aliphatic heterocycle substituted with one or more $R^{19}$; $R^{15}$, $R^{16}$, $R^{17}$ and $R^{18}$ are independently $C_{1-3}$ alkyl; $R^{19}$ is halogen;

or, $R^6$ is $C_{1-3}$ alkyl; $R^7$ is —$NR^{13}R^{14}$; $R^{13}$ is OH, $C_{1-3}$ alkyl, deuterated $C_{1-3}$ alkyl or deuterated $C_{1-3}$ alkyl-O—; $R^{14}$ is $C_{1-3}$ alkyl or deuterated $C_{1-3}$ alkyl;

$R^8$, $R^9$, $R^{10}$ and $R^{11}$ are hydrogen;

wherein, at least one of $R^3$, $R^4$, $R^5$, $R^6$ and $R^7$ is deuterium or a deuterated group;

for example,

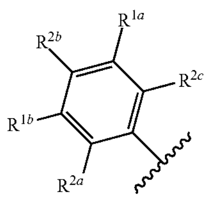

is

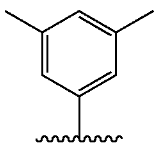

;

for example,

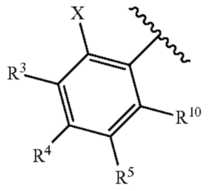

is

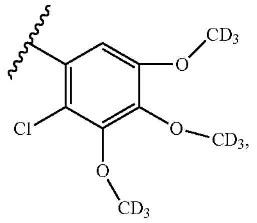

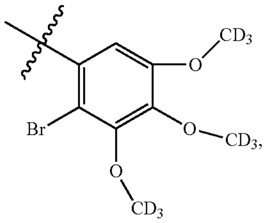

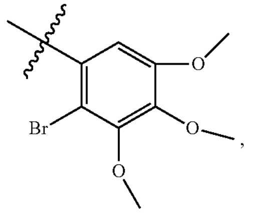

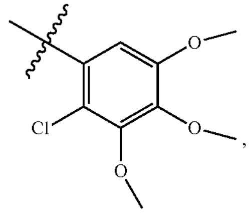

for example,

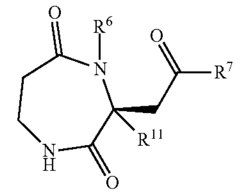

is

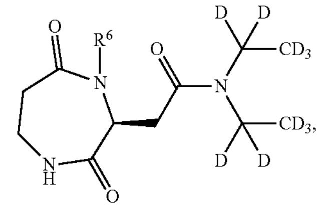

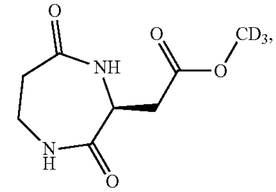

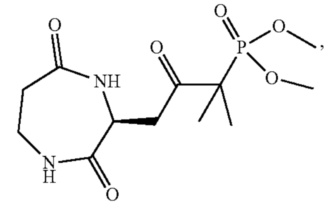

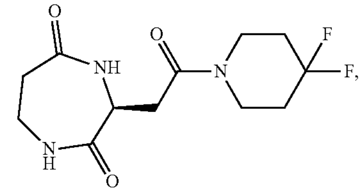

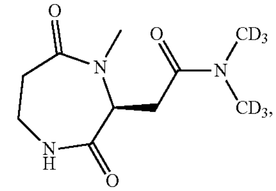

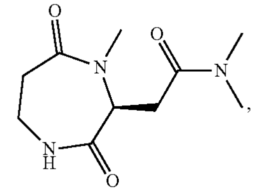

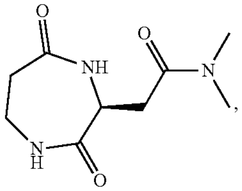

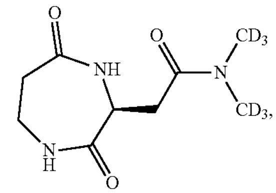

-continued

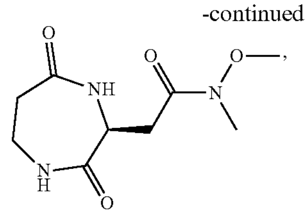

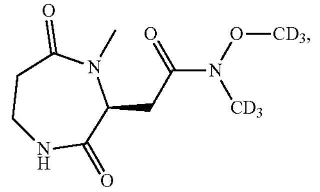

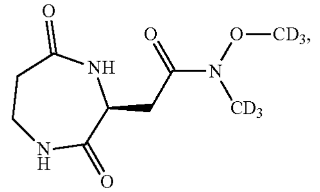

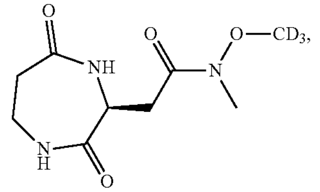

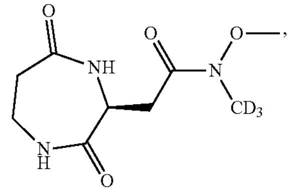

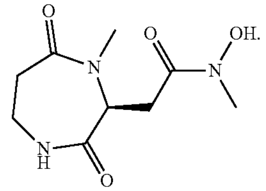

In some preferred embodiments of the present disclosure, some groups in the compound represented by formula I or the pharmaceutically acceptable salt thereof are defined as follows (the groups not mentioned are the same as those described in any solution of the present disclosure), when $R^{1a}$ and $R^{1b}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl can be methyl, ethyl, n-propyl or isopropyl; such as methyl.

In some preferred embodiments of the present disclosure, some groups in the compound represented by formula I or the pharmaceutically acceptable salt thereof are defined as follows (the groups not mentioned are the same as those described in any solution of the present disclosure), when $R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—, the $C_{1-3}$ alkyl in the $C_{1-3}$ alkyl, $C_{1-3}$ alkyl-O—, deuterated $C_{1-3}$ alkyl and deuterated $C_{1-3}$ alkyl-O— can be methyl, ethyl, n-propyl or isopropyl; such as methyl.

In some preferred embodiments of the present disclosure, some groups in the compound represented by formula I or the pharmaceutically acceptable salt thereof are defined as follows (the groups not mentioned are the same as those described in any solution of the present disclosure), when $R^6$ is $C_{1-3}$ alkyl or deuterated $C_{1-3}$ alkyl, the $C_{1-3}$ alkyl and the $C_{1-3}$ alkyl in the deuterated $C_{1-3}$ alkyl can be methyl, ethyl, n-propyl or isopropyl; such as methyl.

In some preferred embodiments of the present disclosure, some groups in the compound represented by formula I or the pharmaceutically acceptable salt thereof are defined as follows (the groups not mentioned are the same as those described in any solution of the present disclosure), when $R^6$ is $C_{2-4}$ alkenyl, the $C_{2-4}$ alkenyl can be vinyl, 1-propenyl, or

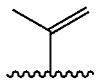 or 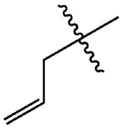.

In some preferred embodiments of the present disclosure, some groups in the compound represented by formula I or the pharmaceutically acceptable salt thereof are defined as follows (the groups not mentioned are the same as those described in any solution of the present disclosure), when $R^6$ is $C_{2-4}$ alkynyl, the $C_{2-4}$ alkynyl can be ethynyl or

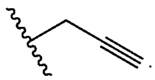 [SMILES: *CC#C].

In some preferred embodiments of the present disclosure, some groups in the compound represented by formula I or the pharmaceutically acceptable salt thereof are defined as follows (the groups not mentioned are the same as those described in any solution of the present disclosure), when $R^{12}$, $R^{17}$ and $R^{18}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl can be methyl, ethyl, n-propyl or isopropyl; such as methyl.

In some preferred embodiments of the present disclosure, some groups in the compound represented by formula I or the pharmaceutically acceptable salt thereof are defined as follows (the groups not mentioned are the same as those described in any solution of the present disclosure), when $R^{15}$ and $R^{16}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl can be methyl, ethyl, n-propyl or isopropyl; such as methyl or ethyl.

In some preferred embodiments of the present disclosure, some groups in the compound represented by formula I or the pharmaceutically acceptable salt thereof are defined as follows (the groups not mentioned are the same as those described in any solution of the present disclosure), when $R^{13}$ and $R^{14}$ are independently $C_{1-3}$ alkyl, deuterated $C_{1-3}$ alkyl, $C_{1-3}$ alkyl-O— or deuterated $C_{1-3}$ alkyl-O—, the $C_{1-3}$ alkyl in the $C_{1-3}$ alkyl, deuterated $C_{1-3}$ alkyl, $C_{1-3}$ alkyl-O— or deuterated $C_{1-3}$ alkyl-O— can be methyl, ethyl, n-propyl or isopropyl; such as methyl or ethyl.

In some preferred embodiments of the present disclosure, some groups in the compound represented by formula I or the pharmaceutically acceptable salt thereof are defined as follows (the groups not mentioned are the same as those described in any solution of the present disclosure), when $R^{13}$ and $R^{14}$ together with the attached nitrogen atom form: a 4- to 6-membered aliphatic heterocycle or a 4-6-membered aliphatic heterocycle substituted by one or more $R^{19}$, the 4- to 6-membered aliphatic heterocycle in the 4- to 6-membered aliphatic heterocycle and the 4- to 6-membered aliphatic heterocycle substituted by one or more $R^{19}$ is 4- to 6-membered heterocyclic alkyl, wherein containing 0-1 heteroatoms selected from N, O or S, besides the 1 shown N attached to the shown carbonyl; such as

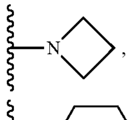, 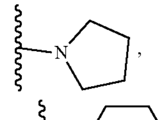, 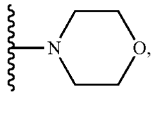, 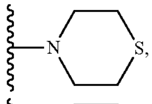, 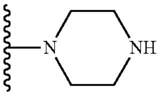 or 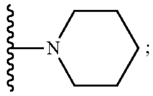;

such as 6-membered heterocyclic alkyl, wherein containing 0-1 heteroatoms selected from N O or S, besides the 1 shown N attached to the shown carbonyl; such as

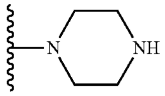 or 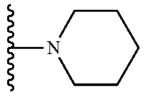.

In some preferred embodiments of the present disclosure, some groups in the compound represented by formula I or the pharmaceutically acceptable salt thereof are defined as follows (the groups not mentioned are the same as those described in any solution of the present disclosure), when the $R^{19}$ is halogen, the halogen can be fluorine, chlorin, bromine or iodine; for example, fluorine or chlorin, for example, fluorine.

In some preferred embodiments of the present disclosure, some groups in the compound represented by formula I or the pharmaceutically acceptable salt thereof are defined as follows (the groups not mentioned are the same as those described in any solution of the present disclosure), when $R^{19}$ is $C_{1-3}$ alkyl or deuterated $C_{1-3}$ alkyl, the $C_{1-3}$ alkyl in the $C_{1-3}$ alkyl and the deuterated $C_{1-3}$ alkyl can be methyl, ethyl, n-propyl or isopropyl; such as methyl.

In some preferred embodiments of the present disclosure, some groups in the compound represented by formula I or the pharmaceutically acceptable salt thereof are defined as follows (the groups not mentioned are the same as those described in any solution of the present disclosure), X is hydrogen, fluorine, chlorine, bromine or iodine;

$R^{1a}$ and $R^{1b}$ are independently $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl, $C_{2-4}$ alkynyl or deuterated $C_{1-3}$ alkyl;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently $C_{1-3}$ alkyl or deuterated $C_{1-3}$ alkyl; $R^{11}$ and $R^{16}$ are independently H, $C_{1-3}$ alkyl or deuterated $C_{1-3}$ alkyl;

$R^{13}$ and $R^{14}$ are independently OH, $C_{1-3}$ alkyl, deuterated $C_{1-3}$ alkyl, $C_{1-3}$ alkyl-O— or deuterated $C_{1-3}$alkyl-O—; or, $R^{13}$ and $R^{14}$ together with the attached nitrogen atom form: a 4- to 6-membered aliphatic heterocycle or a 4- to 6-membered aliphatic heterocycle substituted by one or more $R^{19}$; $R^{19}$ is halogen, O═, $C_{1-3}$ alkyl or deuterated $C_{1-3}$ alkyl;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group.

In some preferred embodiments of the present disclosure, some groups in the compound represented by formula I or the pharmaceutically acceptable salt thereof are defined as follows (the groups not mentioned are the same as those described in any solution of the present disclosure), X is hydrogen, fluorine, chlorine, bromine or iodine;

$R^{1a}$ and $R^{1b}$ are independently $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl,

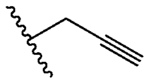

or deuterated $C_{1-3}$ alkyl;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently $C_{1-3}$ alkyl or deuterated $C_{1-3}$ alkyl; $R^{15}$ and $R^{16}$ are independently H, $C_{1-3}$ alkyl or deuterated $C_{1-3}$ alkyl;

$R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—; or, $R^{13}$ and $R^{14}$ together with the attached nitrogen atom form a 4- to 6-membered aliphatic heterocycle or a 4- to 6-membered aliphatic heterocycle substituted by one or more $R^{19}$;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group.

In some preferred embodiments of the present disclosure, some groups in the compound represented by formula I or the pharmaceutically acceptable salt thereof are defined as follows (the groups not mentioned are the same as those described in any solution of the present disclosure), X is fluorine, chlorine or bromine;

$R^{1a}$ and $R^{1b}$ are independently methyl or deuterated methyl;

$R^{2a}$, $R^{2b}$ and $R^{2c}$ are independently hydrogen or deuterium;

$R^3$, $R^4$ and $R^5$ are independently methyl methyl-O—, $CD_3$ or $CD_3$-O—;

$R^6$ is H, methyl,

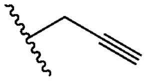 [SMILES: *CC#C]

or $CD_3$;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently methyl, ethyl, $CD_3$ or —$CD_2$-$CD_3$;

$R^{15}$ and $R^{16}$ are independently methyl, ethyl, $CD_3$ or —$CD_2$-$CD_3$;

$R^{13}$ and $R^{14}$ are independently OH, methyl, ethyl, $CD_3$, —$CD_2$-$CD_3$ or $CD_3$-O—, or, $R^{13}$ and $R^{14}$ together with the attached nitrogen atom form:

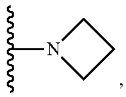, 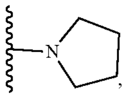, 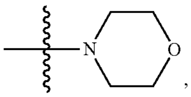, 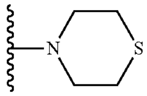, 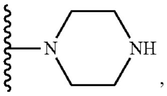, 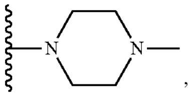, 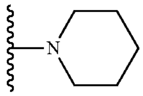, 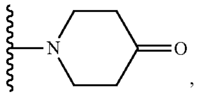, 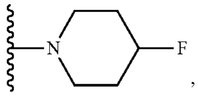, 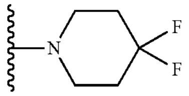 or 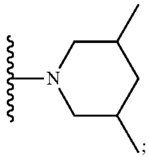;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group.

In some preferred embodiments of the present disclosure, some groups in the compound represented by formula I or the pharmaceutically acceptable salt thereof are defined as follows (the groups not mentioned are the same as those described in any solution of the present disclosure), X is chlorine or bromine;

$R^{1a}$ and $R^{1b}$ are independently methyl or $CD_3$;

$R^{2a}$, $R^{2b}$ and $R^{2c}$ are independently hydrogen or deuterium;

$R^3$, $R^4$ and $R^5$ are independently methyl, methyl-O—, $CD_3$ or $CD_3$-O—;

$R^6$ is H, methyl, or $CD_3$;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently methyl, ethyl, $CD_3$ or —$CD_2$-$CD_3$; such as methyl or $CD_3$;

$R^{15}$ and $R^{16}$ are independently methyl;

$R^{13}$ and $R^{14}$ are independently methyl, ethyl, methyl-O—, $CD_3$, —$CD_2$-$CD_3$ or $CD_3$-O—;

or, $R^{13}$ and $R^{14}$ together with the attached nitrogen atom form:

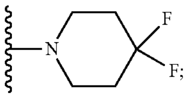 [SMILES: *N1CCC(F)(F)CC1]

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$ and $R^7$ is deuterium or a deuterated group;

In some preferred embodiments of the present disclosure, some groups in the compound represented by formula I or the pharmaceutically acceptable salt thereof are defined as follows (the groups not mentioned are the same as those described in any solution of the present disclosure),

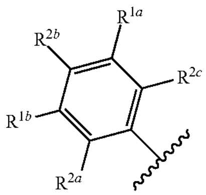

is

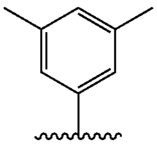

,

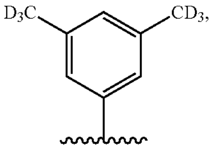

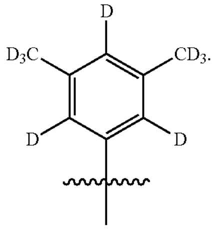

In some preferred embodiments of the present disclosure, some groups in the compound represented by formula I or the pharmaceutically acceptable salt thereof are defined as follows (the groups not mentioned are the same as those described in any solution of the present disclosure),

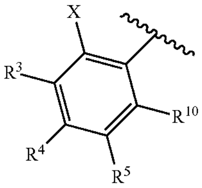

is

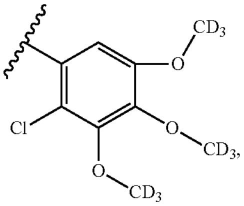

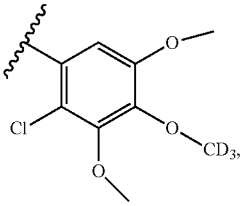

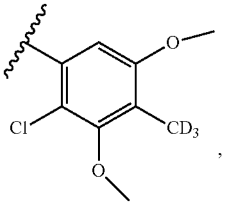

,

-continued

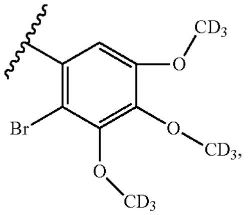

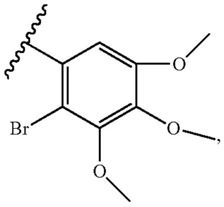

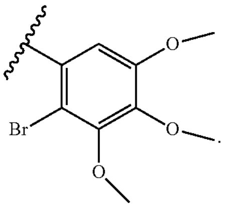

In some preferred embodiments of the present disclosure, some groups in the compound represented by formula I or the pharmaceutically acceptable salt thereof are defined as follows (the groups not mentioned are the same as those described in any solution of the present disclosure),

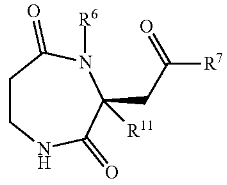

is

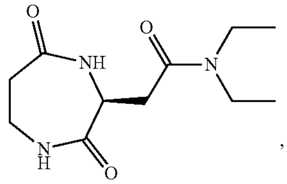

,

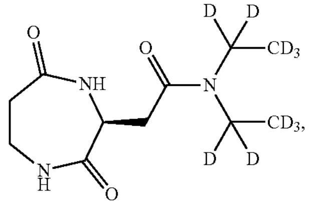

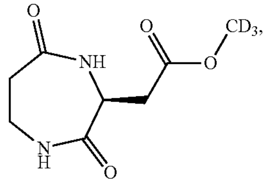

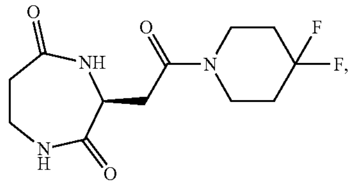

-continued
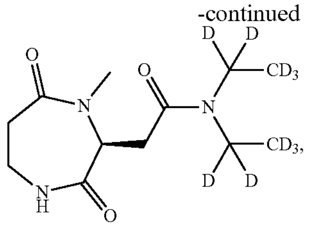
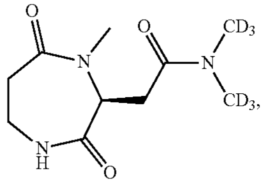
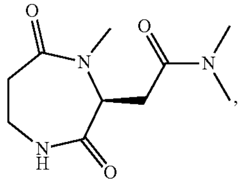
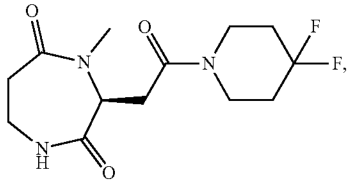
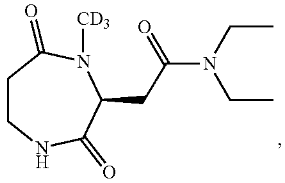
,
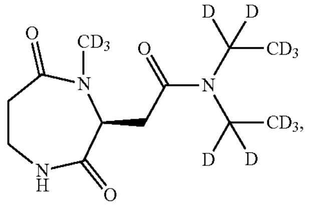
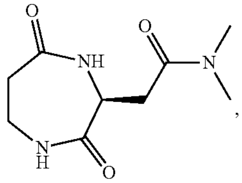
,
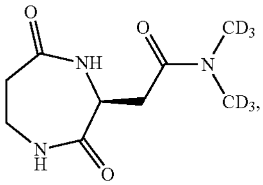
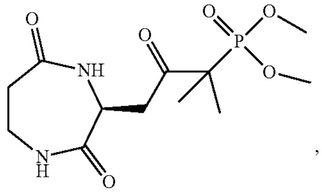
,
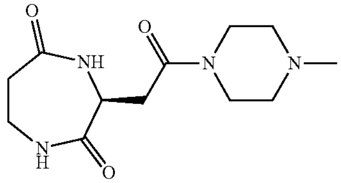
,
-continued
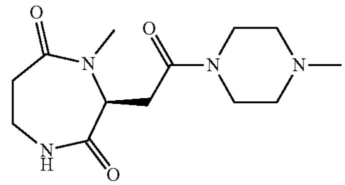
,
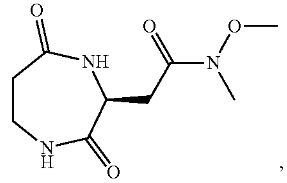
,
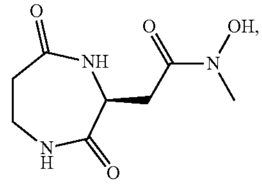
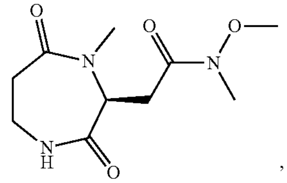
,
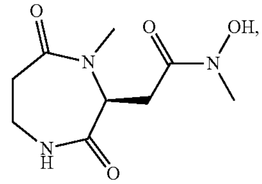
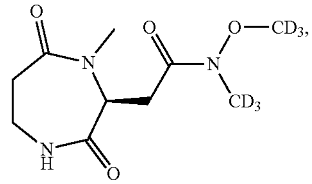
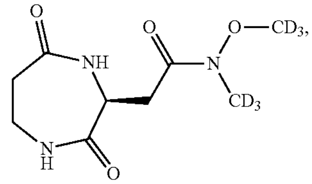
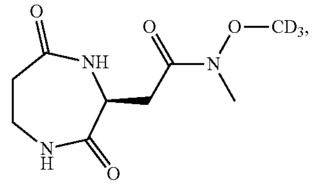
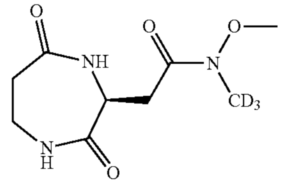
.

In some preferred embodiment of the present disclosure, the compound represented by formula I or the pharmaceutically acceptable salt thereof is any of the following compounds:
Compound 1
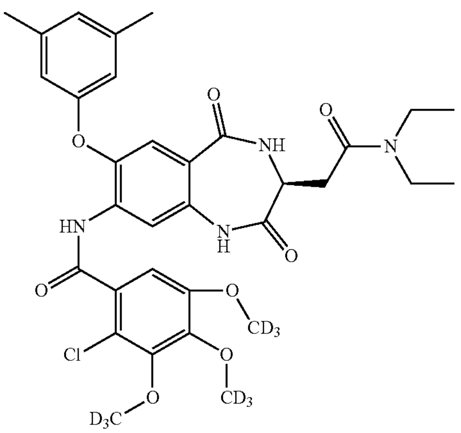
Compound 2
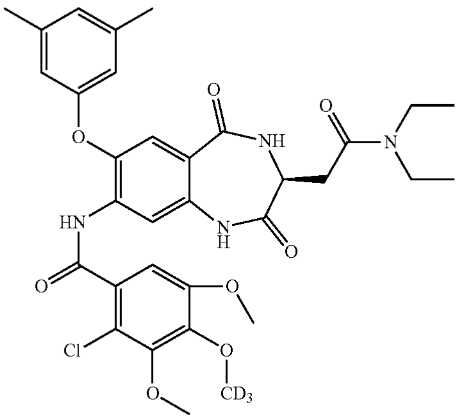
Compound 3
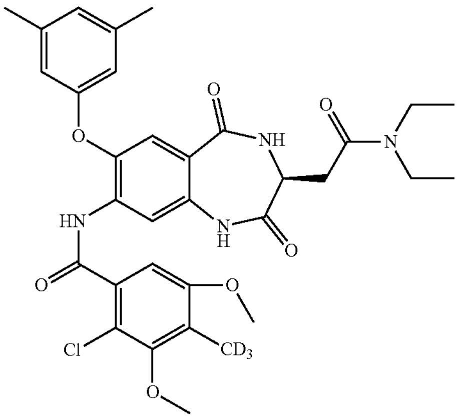
-continued
Compound 4
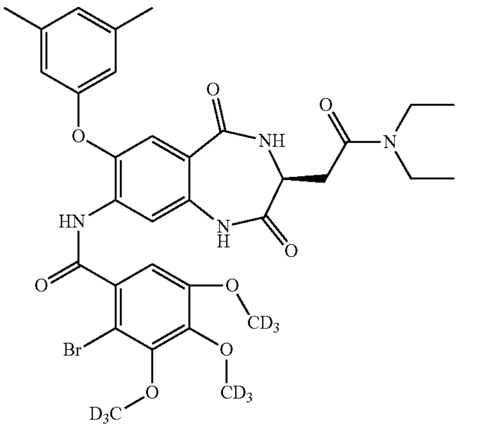
Compound 5
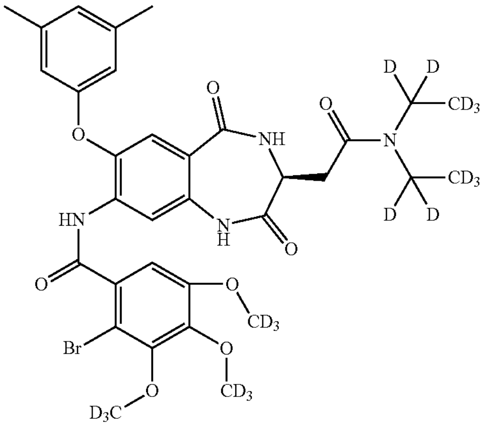
Compound 6
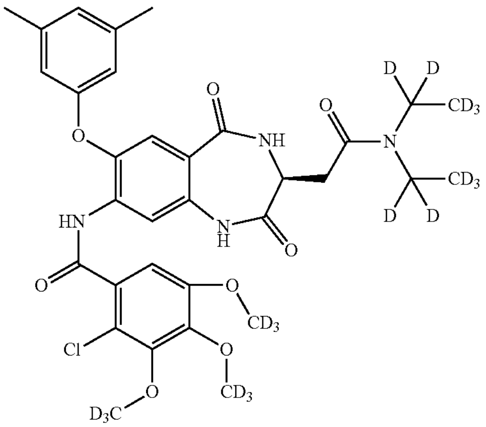

-continued
Compound 7
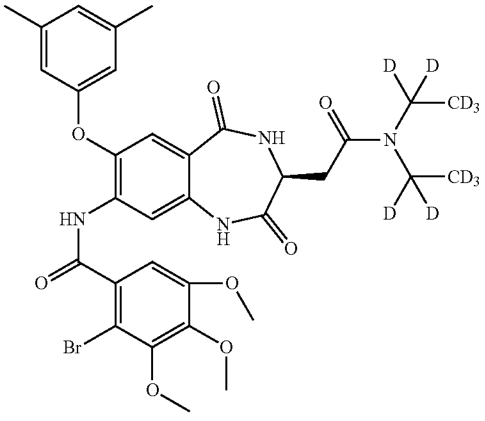
Compound 8
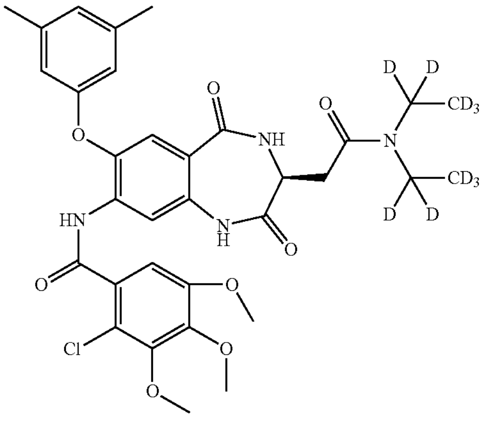
Compound 9
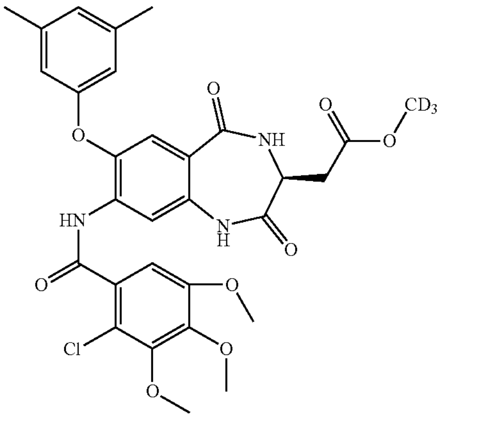
-continued
Compound 10
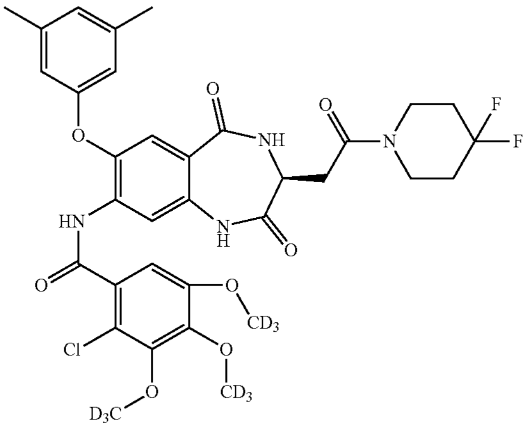
Compound 11
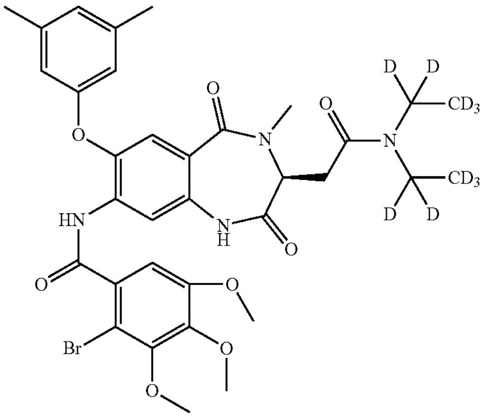
Compound 12
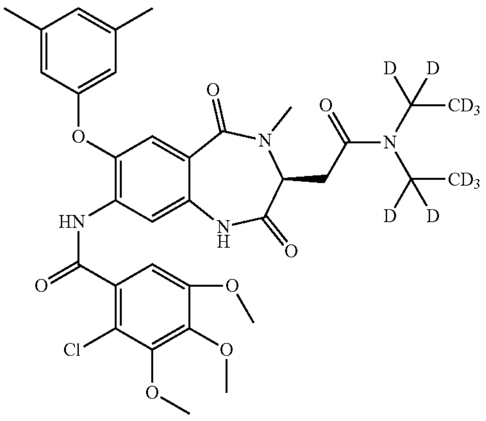

-continued
Compound 13
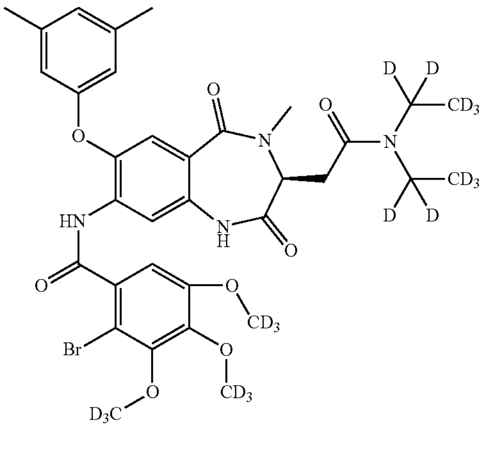
Compound 14
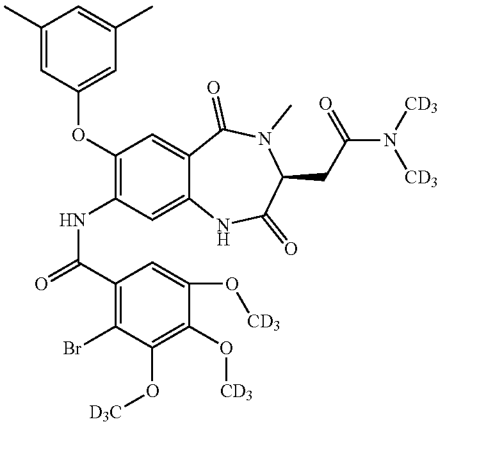
Compound 15
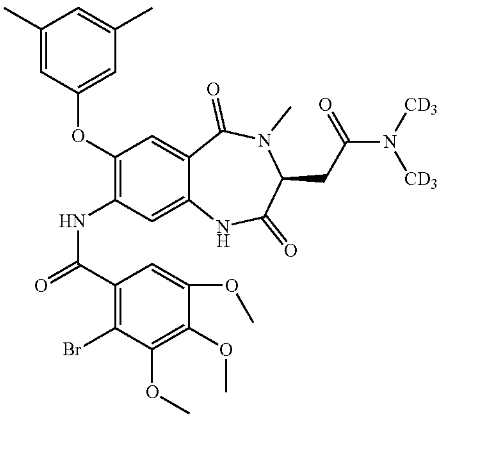
-continued
Compound 16
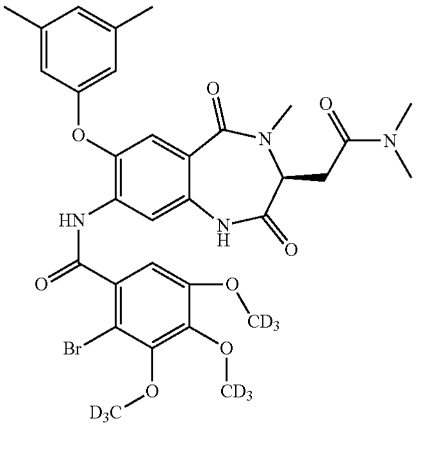
Compound 17
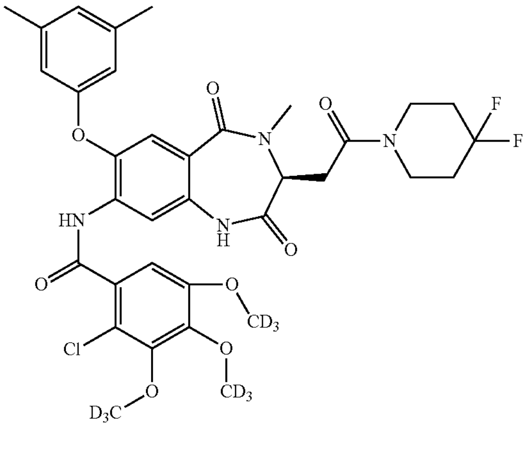
Compound 18
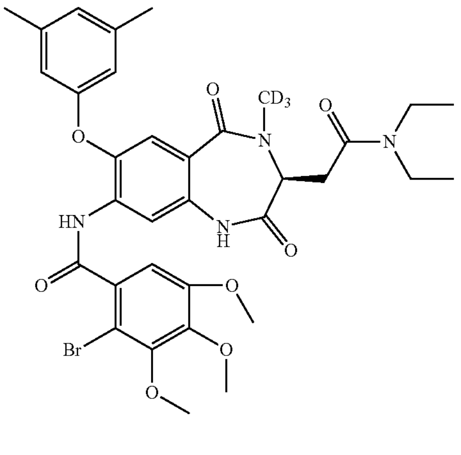

Compound 19
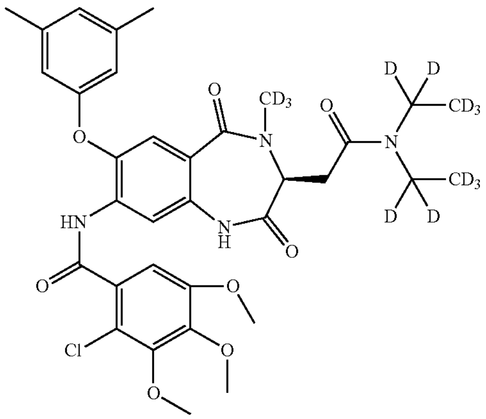
Compound 20
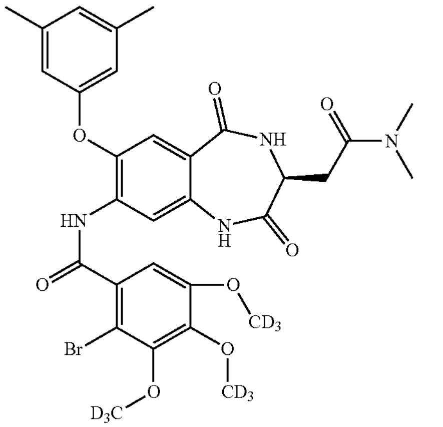
Compound 21
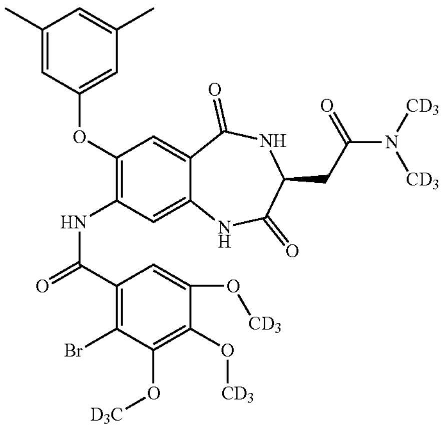
Compound 22
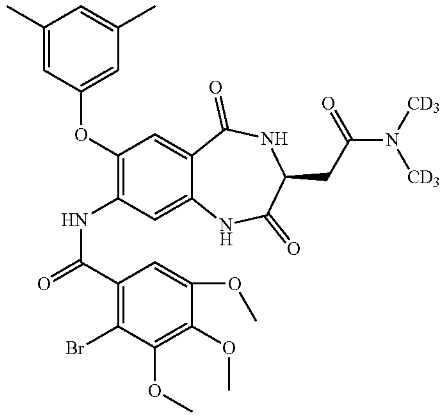
Compound 23
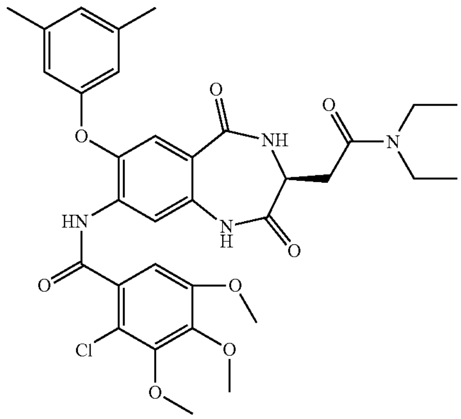
Compoung 25
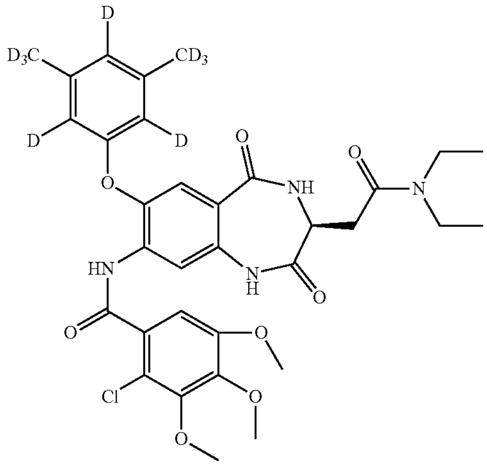

-continued
Compound 26
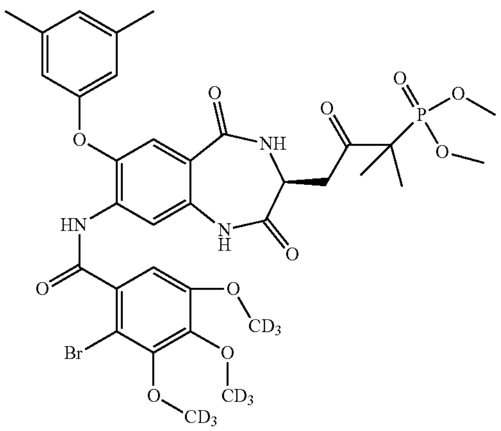
Compound 27
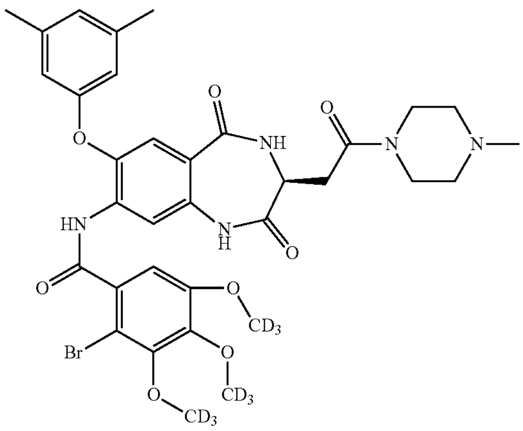
HCl
Compound 28
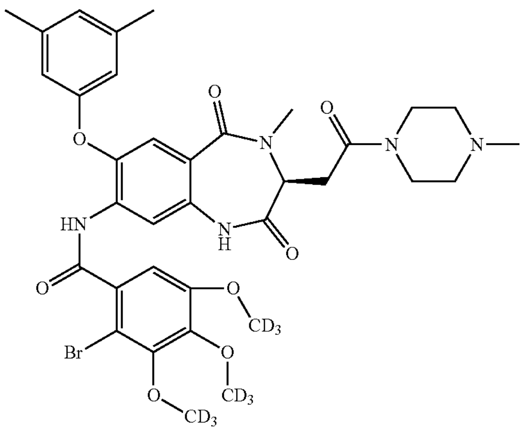
-continued
Compound 29
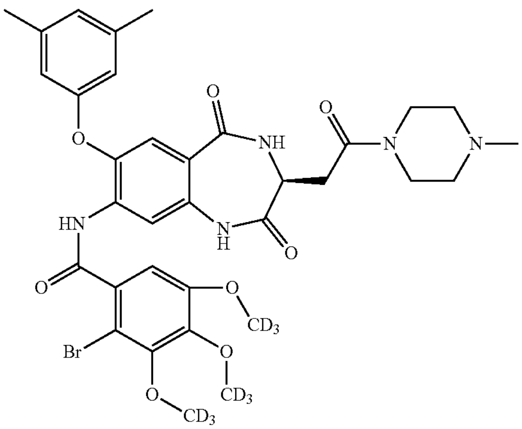
Compound 30
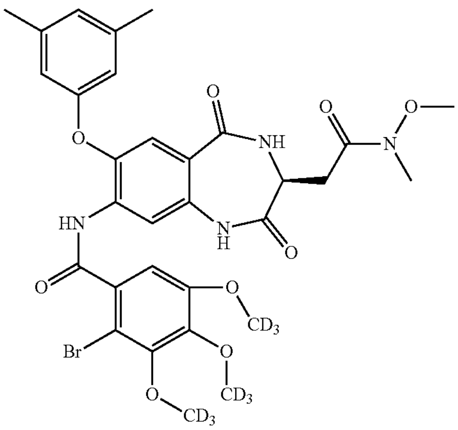
Compound 31
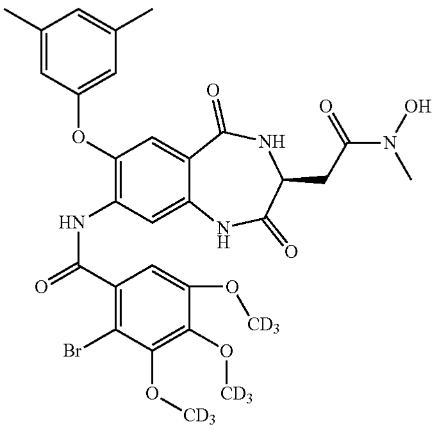

Compound 32
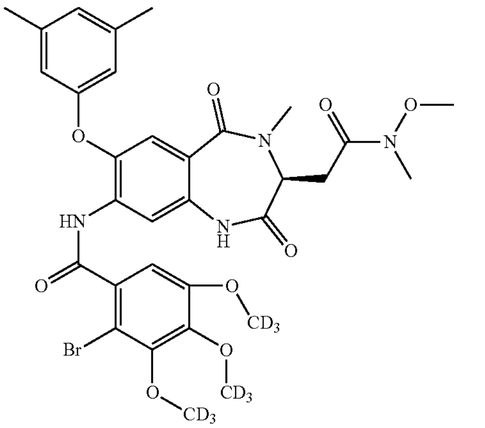
Compooound 33
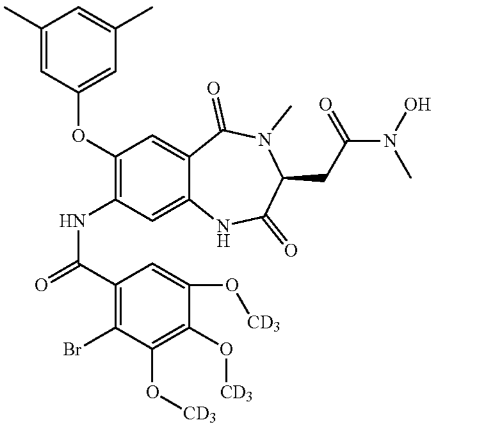
Compound 34
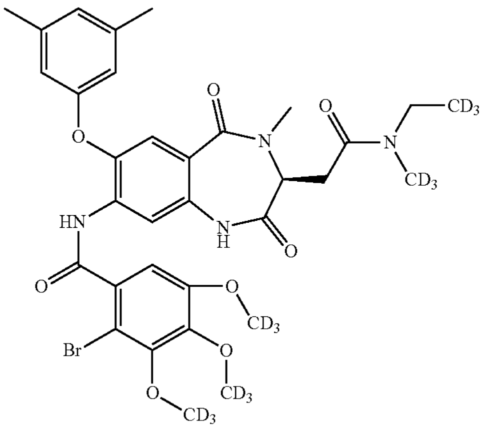
Compound 35
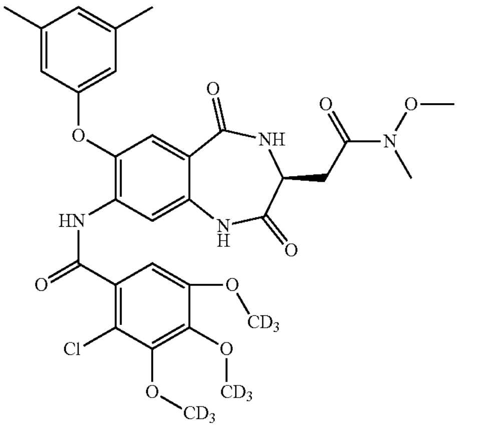
Compound 36
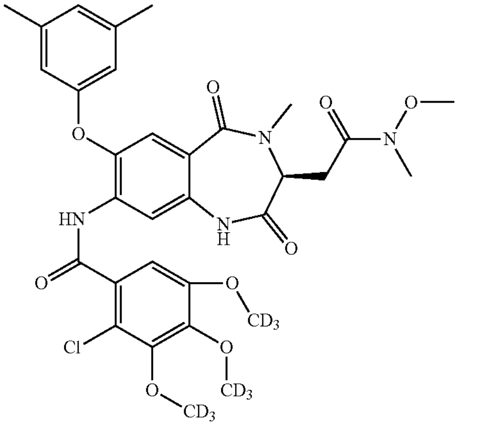
Compound 37
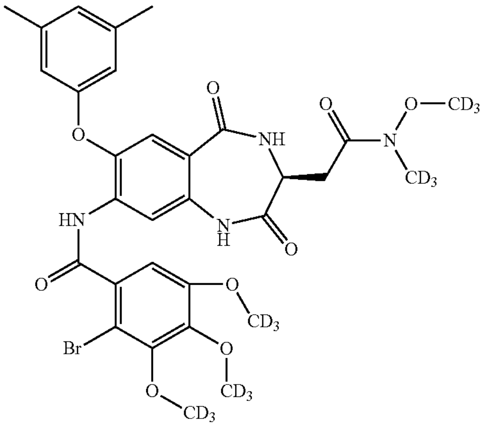

-continued

Compound 38

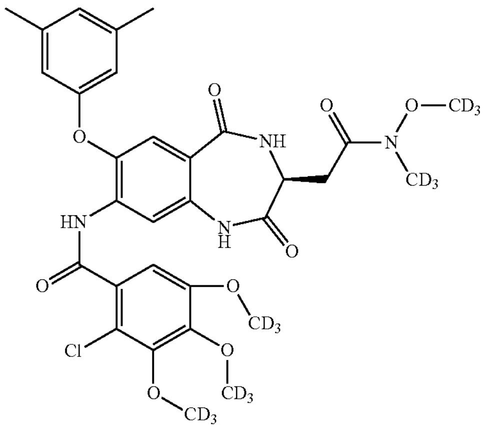

Compound 39

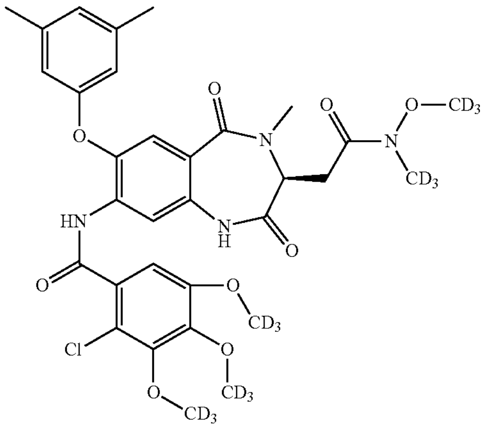

Compound 40

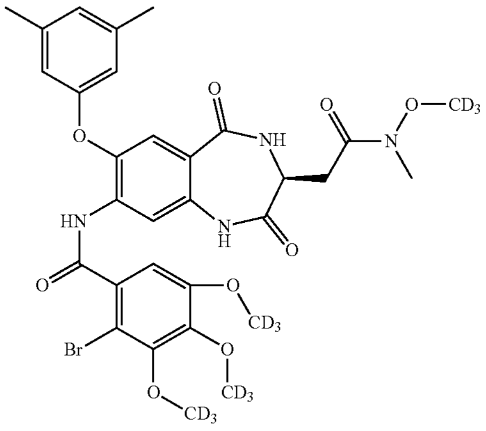

-continued

Compound 41

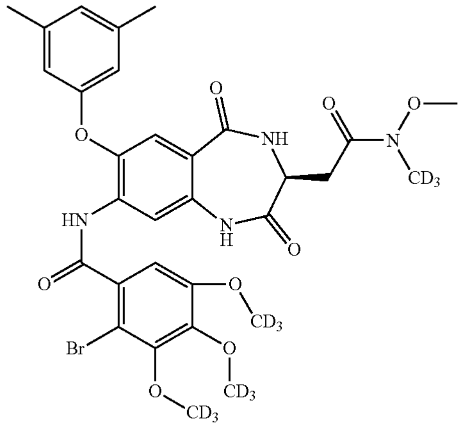

The compound represented by formula I or the pharmaceutically acceptable salt thereof in the present disclosure can be synthesized by methods including methods similar to those known in the chemical field, and steps and conditions of which can refer to the steps and conditions of similar reactions in the art, especially according to the description herein. Starting materials are typically derived from commercial sources such as Aldrich or can be readily prepared by methods known to those skilled in the art (available through SciFinder, Reaxys online databases).

The raw materials or reagents necessary for the preparation of the compound represented by formula I or the pharmaceutically acceptable salt thereof can be obtained commercially or prepared by synthetic methods known in the art. The compound of the present disclosure that are a free base or an acid addition salt thereof can be prepared by the method described in the experimental part below. The term pharmaceutically acceptable salt refers to the pharmaceutically acceptable salt as defined herein, and has all the effects of the parent compound. The pharmaceutically acceptable salt can be prepared by adding a corresponding acid into an appropriate organic solvent of an organic base and treating according to conventional methods.

Examples of salt formation include: for a base addition salt, it is possible to prepare an alkali metal (such as sodium, potassium or lithium) or alkaline earth metal (such as aluminum, magnesium, calcium, zinc or bismuth) salt by treating the compound of the present disclosure with appropriate acidic protons in an aqueous medium using an alkali metal or alkaline earth metal hydroxide or alkoxide (such as an ethanol salt or a methanol salt) or an appropriate alkaline organic amine (such as diethanolamine, choline or meglumine).

Or, for an acid addition salt, the salt formed with an inorganic acid, such as hydrochloric acid, hydrobromic acid, sulfuric acid, nitric acid, phosphoric acid; and the salt formed with an organic acid, such as acetic acid, benzenesulfonic acid, benzoic acid, camphorsulfonic acid, ethanesulfonic acid, fumaric acid, glucoheptonic acid, glutamic acid, glycollic acid, hydroxynaphthoic acid, 2-hydroxyethanesulphonic acid, lactic acid, maleic acid, malic acid, oxalic acid, pyruvic acid, malonic acid, mandelic acid, methanesulfonic acid, muconic acid, 2-naphthalenesulfonic acid, propionic acid, salicylic acid, succinic acid, tartaric acid, citric acid, cinnamic acid, p-toluenesulfonic acid or trimethylacetic acid.

In the present disclosure, the compound represented by formula I or the pharmaceutically acceptable salt thereof can also be obtained by peripheral modifications of the compound represented by formula I or the pharmaceutically acceptable salt thereof, which has already been prepared, to obtain other carbonyl heterocyclic compound represented by formula I or the pharmaceutically acceptable salt thereof, using conventional methods in the art.

Generally, the compound in the present disclosure can be prepared by the methods described herein, unless further specified, wherein the substituents are defined as represented by formula I.

A second aspect of the present disclosure also relates to a pharmaceutical composition comprising the compound of the present disclosure as an active ingredient.

The present disclosure provides a pharmaceutical composition, comprising the compound represented by formula I or the pharmaceutically acceptable salt thereof as described above, and a pharmaceutically acceptable carrier. In the pharmaceutical composition, a dosage of the compound represented by formula I or the pharmaceutically acceptable salt thereof can be a therapeutically effective amount.

The pharmaceutical composition can be prepared according to methods known in the art. The compound of the present disclosure can be combined with one or more pharmaceutically acceptable carriers (such as solid or liquid excipients and/or adjuvants) to make any dosage form suitable for human or animal use. The content of the compound of the present disclosure in the pharmaceutical composition is usually 0.1-95%.

The compound of the present disclosure or the pharmaceutical composition comprising it can be administered in unit dose form, and the route of administration can be intestinal or non-intestinal, such as oral, intravenous, intramuscular, subcutaneous, nasal, oral mucosa, eyes, lungs and respiratory tract, skin, vagina, rectum, etc.

The dosage form can be a liquid dosage form, a solid dosage form or a semi-solid dosage form. The liquid dosage form can be solution (including true solution and colloidal solution), emulsion (including o/w type, w/o type and multiple emulsion), suspension, injection (including water injection, powder injection and infusion), eye drop, nasal drop, lotions and liniment, etc.; the solid dosage form can be tablet (including ordinary tablet, enteric-coated tablet, buccal tablet, dispersible tablet, chewable tablet, effervescent tablet, orally disintegrating tablet), capsule (including hard capsule, soft capsule, enteric capsule), granule, powder, pellet, dropping pill, suppository, film, patche, gas (powder) aerosol, spray, etc.; the semi-solid dosage form can be ointment, gel, paste, etc.

The compound of the present disclosure can be made into ordinary preparation, and can also be made into sustained release preparation, controlled release preparation, targeted preparation and various particulate delivery systems.

In order to make the compound of the present disclosure into tablet, a wide variety of excipients known in the art can be used, including diluent, humectant, binder, disintegrant, lubricant, and flow aid. The diluent can be starch, dextrin, sucrose, glucose, lactose, mannitol, sorbitol, xylitol, microcrystalline cellulose, calcium sulfate, calcium hydrogen phosphate, calcium carbonate, etc.; the humectant can be water, ethanol, isopropanol, etc.; the binder can be starch slurry, dextrin, syrup, honey, glucose solution, microcrystalline cellulose, acacia mucilage, gelatin mucilage, sodium carboxymethyl cellulose, methyl cellulose, hydroxypropyl methyl cellulose, ethyl cellulose, acrylic resin, carbomer, polyvinylpyrrolidone, polyethylene glycol, etc.; the disintegrant can be dry starch, microcrystalline cellulose, low-substituted hydroxypropyl cellulose, cross-linked polyvinylpyrrolidone, cross-linked sodium carboxymethyl cellulose, sodium carboxymethyl starch, sodium bicarbonate and citric acid, polyoxyethylene sorbitol fatty acid ester, sodium dodecyl sulfonate, etc.; the lubricant and the flow aid can be talc powder, silicon dioxide, stearate, tartaric acid, liquid paraffin, polyethylene glycol, etc.

The tablet can also be further made into coated tablet, such as sugar-coated tablet, film-coated tablet, enteric-coated tablet, or double layer and multi-layer tablets.

In order to make drug delivery unit into capsule, the compound of the present disclosure as an active ingredient can be mixed with the diluent and the flow aid, and the mixture can be placed directly in hard or soft capsule. The compound of the present disclosure as an active ingredient can also be mixed with the diluent, the binder and the disintegrant to make granule or pellet, then be placed in hard or soft capsules. The various diluents, humectants, binders, disintegrants, and flow aids used to prepare the tablet of the compound of the present disclosure can also be used to prepare capsule of the compound of the present disclosure.

In order to make the compound of the present disclosure into injection, water, ethanol, isopropanol, propylene glycol or their mixture can be used as solvent, and appropriate amounts of solubilizer, cosolvent, pH regulator and osmotic regulator commonly used in the art can be added. The solubilizer or cosolvent can be poloxamer, lecithin, hydroxypropyl-beta-cyclodextrin, etc.; the pH regulator can be phosphate, acetate, hydrochloric acid, sodium hydroxide, etc.; the osmotic regulator can be sodium chloride, mannitol, glucose, phosphate, acetate, etc. If freeze-dried powder injection is prepared, mannitol, glucose, etc. can also be added as proppant.

In addition, if necessary, colorants, preservatives, perfumes, corrigents or other additives can also be added into the pharmaceutical preparation.

A third aspect of the present disclosure relates to a use of the compound for preventing and treating a proliferative disease.

The present disclosure provides a use of the compound represented by formula I or the pharmaceutically acceptable salt thereof as described above in the manufacture of a medicament. Specifically, the present disclosure provides the use of the compound or the pharmaceutically acceptable salt thereof in the manufacture of a medicament for preventing or treating proliferative diseases.

The proliferative diseases can be cancer;

For example, cancer, including bladder cancer, brain cancer, breast cancer, colon cancer, rectal cancer, renal cancer, liver cancer, lung cancer, ovarian cancer, pancreatic cancer, adrenal cancer, prostate cancer, stomach cancer, vaginal cancer, cervical cancer, endometrial cancer, central nervous system tumor, melanoma, leukemia, thyroid cancer and skin cancer, etc.;

- lymphatic hematopoietic system tumor, including acute lymphoblastic leukemia, B-cell lymphoma and Burketts lymphoma, etc.;
- marrow hematopoietic system tumor, including acute and chronic myeloid leukemia and promyelocytic leukemia;
- interstitial tumor, including fibrosarcoma and rhabdomyosarcoma;
- other tumors, including melanoma, seminoma, teratoma, neuroblastoma, glioma, etc.

Preferably, lung cancer, colon cancer, central nervous system tumor, melanoma, renal cancer, leukemia, prostate cancer, ovarian cancer or breast cancer; the cell of the lung cancer can be A549 (non-small cell lung cancer) cell; the cell of the colon cancer can be HCT116 (colon cancer) cell; the cell of the central nervous system tumor can be SF295 (central nervous system tumor) cell; the cell of the melanoma can be LOX-IMVI (melanoma) cell; the cell of the renal cancer can be 786-0 (renal cancer) cell; the cell of the leukemia can be K562 (leukemia) cell; the cell of the prostate cancer can be PC-3 (prostate cancer) cell; the cell of the ovarian cancer can be OVCAR-3 (ovarian cancer) cell; the cell of the breast cancer can be HS 578T (breast cancer) cell.

The present disclosure also provides a medicament (or a pharmaceutical composition) comprising the compound represented by formula I, or the tautomer thereof, or the pharmaceutically acceptable salt thereof or the solvate thereof.

The present disclosure also provides a therapeutic medicament (or a pharmaceutical composition) comprising the compound represented by formula I, or the tautomer thereof, or the pharmaceutically acceptable salt thereof or the solvate thereof for preventing and treating proliferative disease.

The present disclosure also provides a use of the compound represented by shown formula I, or the tautomer thereof, or the pharmaceutically acceptable salt thereof or the solvate thereof, or the pharmaceutical composition as described above in the manufacture of a medicament. The medicament can be a medicament for treating and/or preventing proliferative diseases.

The present disclosure also provides a method for treating and/or preventing proliferative disease, which comprises: administering a therapeutically effective amount of the compound represented by formula I, or the tautomer thereof, or the pharmaceutically acceptable salt thereof or the solvate thereof.

The treating and preventing proliferative disease are described above.

To achieve the purpose of medication and to enhance the therapeutic effect, the medicament or the pharmaceutical composition of the present disclosure can be administered by any known method of administration.

The administration dosage of the compound and the pharmaceutical composition of the present disclosure can vary widely according to the nature and severity of the disease to be prevented or treated, the individual situation of the patient or animal, the route of administration and the dosage form. In general, the suitable daily dose range of the compound of the present disclosure is 0.001-150 mg/Kg body weight, preferably 0.1-100 mg/Kg body weight, more preferably 1-60 mg/Kg body weight, most preferably 2-30 mg/Kg body weight. The dose above can be administered in one dose unit or divided into several dose units, which depends on the clinical experience of doctors and the dosage regimen including the use of other treatments.

The compound or the composition of the present disclosure can be administered alone or in combination with other therapeutic or symptomatic medicaments. When the compound of the present disclosure has a cooperative interaction with other therapeutic medicaments, its dose should be adjusted according to the actual situation.

The term "pharmaceutically acceptable" refers to salts, solvents, excipients and the like that are generally non-toxic, safe, and suitable for use in patient. The "patient" is preferably a mammal, more preferably a human being.

The term "pharmaceutically acceptable salt" refers to the salt prepared from the compound of the present disclosure and a relatively non-toxic and pharmaceutically acceptable acid.

The present disclosure claims to protect the "pharmaceutically acceptable salt" of the compound represented by formula I, including the salt formed with an alkali metal such as sodium, potassium, lithium, etc.; the salt formed with an alkaline earth metal such as calcium, magnesium, etc.; the salt formed with other metals such as aluminum, iron, zinc, copper, nickel, cobalt, etc.; the salt formed with an inorganic base such as ammonium; the salt formed with an organic bases such as tert-octylamine, dibenzylamine, morpholine, glucosamine, phenyl glycine alkyl ester, ethylenediamine, N-methylglucosamine, guanidine, diethylamine, triethylamine, dicyclohexylamine, N,N-dibenzylethylenediamine, chloroprocaine, procaine, diethanolamine, N-benzyl-phenylethylamine, piperazine, trimethylamine, tri (hydroxymethyl)aminomethane, etc.; the salt formed with an inorganic acid such as nitric acid, perchloric acid, sulfuric acid, phosphoric acid, hydrofluoric acid, hydrochloric acid, hydrobromic acid, hydroiodic acid, etc.; the salt formed with a sulfonic acid such as methanesulfonic acid, trifluoromethanesulfonic acid, ethanesulfonic acid, benzenesulfonic acid, p-toluenesulfonic acid, etc.; the salt formed with an organic acid such as formic acid, acetic acid, malic acid, fumaric acid, succinic acid, citric acid, tartaric acid, oxalic acid, maleic acid, etc.; the salt formed with an amino acid such as glycine, trimethylglycine, arginine, ornithine, glutamic acid, aspartic acid, etc. The present disclosure is not limited to the pharmaceutically acceptable salt.

"Treatment" means any treatment for diseases in a mammal, which includes (1) preventing the disease, that is, causing clinical disease symptoms not to develop; (2) inhibiting the disease, that is, preventing the development of clinical symptoms; and (3) alleviating the disease, that is, causing the clinical symptoms to resolve.

"Effective amount" refers to a compound, when administered to a patient in need of treatment, the amount of which is sufficient to (i) treat the related disease, (ii) attenuate, ameliorate, or eliminate one or more symptoms of a particular disease or condition, or (iii) delay the onset of one or more symptoms of a particular disease or condition described herein. The amount of the carbonyl heterocyclic compound represented by formula I or the pharmaceutically acceptable salt thereof or the pharmaceutical composition as described above will vary according to factors such as the specific compound, the disease condition and the severity thereof, the characteristics of the patient who needs treatment (such as body weight), etc., but it can still be conventionally determined by those skilled in the art.

The "preventing" in the present disclosure refers to the reduction in the risk of getting or developing a disease or disorder.

The "pharmaceutical composition" in the present disclosure refers to a preparation of one or more compounds of the present disclosure or the salt thereof and a carrier commonly accepted in the art for delivering biologically active compounds to an organism (such as human). The pharmaceutical composition is intended to facilitate drug delivery to the organism.

The term "pharmaceutically acceptable carrier" refers to a substance that is administered in conjunction with the active ingredient and facilitates the administration of the active ingredient, including but not limited to, any flow aid, sweetener, diluent, preservative, dye/colorant, flavor enhancer, surfactant, humectant, dispersant, disintegrant, suspension agent, stabilizer, isotonic agent, solvent or emulsifier approved by the State Food and Drug Administration for use in human or animal (such as domestic animals). For example, including but are not limited to calcium carbonate, calcium phosphate, various sugars and various types of starches, cellulose derivative, gelatin, vegetable oil and polyethylene glycol.

The pharmaceutical composition in the present disclosure can be prepared into solid, semi-solid, liquid or gaseous preparations, such as tablet, pill, capsule, powder, granule, electuary, emulsion, suspension, solution, suppository, injection, inhalation, gel, microsphere and aerosol, etc.

The pharmaceutical composition in the present disclosure can be manufactured by methods well known in the art, such as conventional mixing method, dissolution method, granulation methods, sugar-coated pill making method, grinding method, emulsification method, freeze-drying method, etc.

The route of administration of the compound or the pharmaceutically acceptable salt thereof, or the pharmaceutical composition thereof in the present disclosure, including but not limited to oral, rectal, transmucosal, enteral administration, or topical, transdermal, inhalation, parenteral, sublingual, intravaginal, intranasal, intraocular, intraperitoneal, intramuscular, subcutaneous, intravenous administration. The preferred route of administration is oral administration.

For oral administration, the pharmaceutical composition can be prepared by mixing the active compound with pharmaceutically acceptable carriers known in the art. These carriers enable the compound of the present disclosure to be prepared as tablet, pill, pastille, sugar-coated tablet, capsule, liquid, gel, slurry, suspension, etc. for oral administration to patients. For example, the pharmaceutical composition for oral administration can be obtained as a tablet by combining the active ingredient with one or more solid carriers, if necessary, granulating the resulting mixture, and if necessary, processing the mixture or granules with a small amount of excipients to form a tablet or tablet core. The tablet core can be combined with any coating material suitable for enteric dissolution to be processed into a form of coating preparation that is more favorable for absorption by the organism (such as human).

Unless otherwise indicated, the following definitions used herein shall be applied. For the purposes of the present disclosure, the chemical elements and the CAS version of the periodic table are consistent with the Handbook of Chemistry and Physics, $75^{th}$ edition, 1994. In addition, general principles of organic chemistry can be found in "Organic Chemistry", Thomas Sorrell, University Science Books, Sausalito:1999, and "March's Advanced Organic Chemistry" by Michael B. Smith and Jerry March, John Wiley & Sons, New York: 2007, the entire contents of which are incorporated herein by reference.

In the present specification, the group and substituent thereof can be selected by those skilled in the art to provide a stable structural part and compound. When a substituent is described by a conventional chemical formula written from left to right, the substituent also includes a chemically equivalent substituent obtained by writing the structural formula from right to left.

Some chemical groups defined herein are preceded by simplified symbols to indicate the total number of carbon atoms present in the group. For example, $C_1$-$C_6$ alkyl refers to alkyl having a total of 1, 2, 3, 4, 5 or 6 carbon atoms as defined below. The total number of carbon atoms represented by the simplified symbol does not include the carbon that may exist in the substituent of the group.

In the present disclosure, the number range defined in the substituents such as 0 to 4, 1 to 4, 1 to 3, etc. indicates integers in the range, for example, 1-6 is 1, 2, 3, 4, 5, 6.

In addition to the foregoing, when used in the specification and claim of the present disclosure, unless otherwise specified, the following terms shall have the meanings represented below.

The term "include" is an open-ended expression that includes the content specified in the present disclosure, but does not exclude other aspects of the content.

The term "substituted" refers to the substitution of any one or more hydrogen atom(s) on a specific atom by substituents, including deuterium and hydrogen variables, as long as the valence of the specific atom is normal and the substituted compound is stable.

In general, the term "substituted" means that one or more hydrogen atoms in a given structure are substituted by specific substituents. Further, when the group is substituted by one or more substituents, the substituents are independent of each other, that is, more than one of the substituents may be different from each other or the same. Unless otherwise specified, each substitutable position of the group being substituted can be substituted by a substituent. When more than one position of a given structural formula can be substituted by one or more substituents selected from the specific groups, each position can be substituted by equally or differently substituents.

The term "one or more" or "one or more than two" refers to 1, 2, 3, 4, 5, 6, 7, 8, 9 or more; such as 1, 2, 3, 4 or 5.

The term "include" is an open-ended expression that includes the content specified in the present disclosure, but does not exclude other aspects of the content.

The term "substituted" refers to the substitution of any one or more hydrogen atom(s) on a specific atom by substituents, including deuterium and hydrogen variables, as long as the valence of the specific atom is normal and the substituted compound is stable.

In general, the term "substituted" means that one or more hydrogen atoms in a given structure are substituted by specific substituents. Further, when the group is substituted by one or more substituents, the substituents are independent of each other, that is, more than one of the substituents may be different from each other or the same. Unless otherwise specified, each substitutable position of the group being substituted can be substituted by a substituent. When more than one position of a given structural formula can be substituted by one or more substituents selected from the specific groups, each position can be substituted by equally or differently substituents.

In each part of the present specification, the substituents of the compounds disclosed in the present disclosure are disclosed according to the types or ranges of the groups. In particular, the present disclosure includes each independent sub-combination of the individual members of the type and range of the groups. The term "Cr-Cy alkyl" refers to straight or branched chain saturated hydrocarbon comprising x to y carbon atoms. For example, the term "$C_1$-$C_6$ alkyl" or "$C_{1-6}$ alkyl" refers specifically to independently disclosed methyl, ethyl, $C_3$ alkyl, $C_4$ alkyl, $C_5$ alkyl and $C_6$ alkyl; "$C_{1-4}$ alkyl" refers specifically to independently disclosed methyl, ethyl, $C_3$ alkyl (that is, propyl, including n-propyl and isopropyl), $C_4$ alkyl (that is, butyl, including n-butyl, isobutyl, sec-butyl and tert-butyl).

The term "halogen" is selected from F, Cl, Br or I, especially F, Cl or Br.

The term "alkoxy" refers to the group —O—$R^x$, wherein $R^x$ is the alkyl as defined above.

The terms "part," "structural part," "chemical part," "group" and "chemical group" used herein refer to a specific fragment or functional group in a molecule. The chemical part is usually considered as a chemical entity embedded or attached to a molecule.

When the listed substituents do not indicate which atom they are connected to the compound included but not specifically mentioned in the general formula of chemical structure, the substituent can be bonded to it through any of its atoms. The combination of the substituent and/or variant thereof is only permissible if the combination will produce a stable compound.

When the listed group is not explicitly indicated that it has a substituent, the group only refers to being unsubstituted. For example, when "$C_1$-$C_4$ alkyl" is not preceded by "substituted or unsubstituted", it only refers to "$C_1$-$C_4$ alkyl" itself or "unsubstituted $C_1$-$C_4$ alkyl".

In each part of the present disclosure, linking substituents are described. When the structure clearly requires a linking group, the Markush variables listed for the group should be understood as the linking group. For example, if the structure requires the linking group and the definition of the Markush group for the variables lists "alkyl", it should be understood that the "alkyl" represents the linking alkylidene group.

In some specific structures, when an alkyl group is clearly expressed as a linking group, the alkyl group represents a linking alkylidene group, for example, the $C_1$-$C_6$ alkyl in the group "halo-$C_1$-$C_6$ alkyl" should be understood as $C_1$-$C_6$ alkylidene.

The term "alkylidene" means a saturated divalent hydrocarbon group obtained by removing two hydrogen atoms from a saturated straight or branched chain hydrocarbon group. Examples of the alkylidene group include methylene ($-CH_2-$), ethylene {including $-CH_2CH_2-$ or $-CH(CH_3)-$}, isopropylidene {including $-CH(CH_3)CH_2-$ or $-C(CH_3)_2-$}, etc.

In the present disclosure, as a group or as part of another group (such as in a halogen-substituted alkyl group, etc.), the term "alkyl" refers to a branched and straight chain saturated aliphatic hydrocarbon group comprising a specified number of carbon atoms; for example, a straight or branched saturated hydrocarbon chain comprising 1 to 16 carbon atoms; for example, $C_1$-$C_6$ alkyl. For example, "$C_1$-$C_6$ alkyl" is defined as the group having 1, 2, 3, 4, 5, or 6 carbon atoms in a straight or branched chain structure. Wherein propyl is $C_3$ alkyl (including isomers, such as n-propyl or isopropyl); butyl is $C_4$ alkyl (including isomers, such as n-butyl, sec-butyl, isobutyl or tert-butyl); pentyl is $C_5$ alkyl (including isomers, such as n-pentyl, 1-methyl-butyl, 1-ethyl-propyl, 2-methyl-1-butyl, 3-methyl-1-butyl, isopentyl, tert-pentyl or neopentyl); hexyl is $C_6$ alkyl (including isomers, such as n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl).

The "$C_{1-3}$ alkyl" in the present disclosure refers to straight or branched chain alkyl derived from removing one hydrogen atom of a hydrocarbon containing 1-3 carbon atoms.

In the present disclosure, as a group or as part of another group, the term "alkenyl" means a straight or branched hydrocarbon chain group consisting of only carbon and hydrogen atoms, comprising at least one carbon-carbon double bond and no carbon-carbon triple bond, having, for example, 2 to 14 (preferably 2 to 10, more preferably 2 to 6) carbon atoms, and connecting to the rest of the molecule by a single bond. The one or more carbon-carbon double bond can be internal (such as in 2-butenyl) or terminal (such as in 1-butenyl). Wherein it includes the positioning of "cis" and "trans", or the positioning of "E" and "Z".

In some embodiments, the alkenyl group has 2 to 4 carbon atoms ("$C_{2-4}$ alkenyl or $C_2$-$C_4$ alkenyl"). Preferably, one carbon-carbon double bond exists, and up to two non-aromatic carbon-carbon double bonds can exist. Examples of $C_{2-4}$ alkenyl group include vinyl ($C_2$ 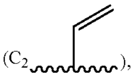), 1-propenyl ($C_3$ 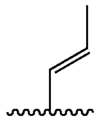 or 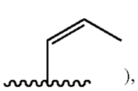), 2-propenyl or isopropenyl ($C_3$ 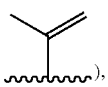), allyl ($C_3$ 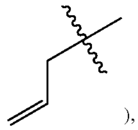), 1-butenyl ($C_4$ 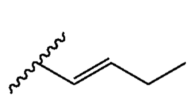 or 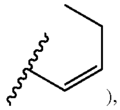), 2-butenyl ($C_4$ 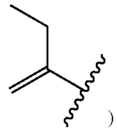)

(crotyl), 2-methylallyl ($C_4$ 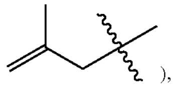), 2-methylprop-1-en-1-yl ($C_4$ 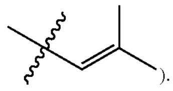).

but-3-en-1-yl ($C_4$ 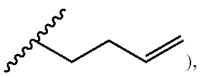), butadienyl {$C_4$; (E)-but-1,3-dien-1-ylbenzene (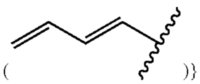 [SMILES: */C=C/C=C])} and isomers (such as cis-trans isomers, isomers or stereoisomers).

The "$C_{2-4}$ alkenyl" in the present disclosure refers to a straight or branched chain alkenyl with 2-4 carbon atoms comprising double bonds.

In this application, as a group or as part of another group, unless otherwise specified, the term "alkynyl" refers to a straight or branched chain hydrocarbon group containing a specified number of carbon atoms and at least one carbon-carbon triple bond. Wherein up to three carbon-carbon triple bonds can exist. For example, a straight or branched chain hydrocarbon group ("$C_2$-$C_{2M}$ alkynyl") having 2 to 20 carbon atoms, one or more carbon-carbon triple bonds and optionally one or more carbon-carbon double bonds. The one or more carbon-carbon triple bond can be internal (such as in the 2-butynyl) or terminal (such as in the 1-butynyl). Thus, "$C_2$-$C_4$ alkynyl" refers to alkynyl with 2-4 carbon atoms. In some embodiments, the alkynyl has 2 to 4 carbon atoms ("$C_2$-$C_4$ alkynyl"), such as ethynyl ($C_2$), prop-1-ynyl (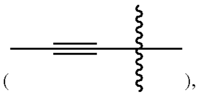), prop-2-ynyl (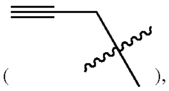), but-1-ynyl (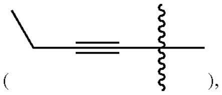), but-2-ynyl (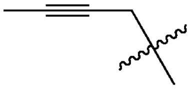), but-3-ynyl (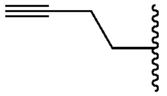)

or 1-methylprop-2-ynyl (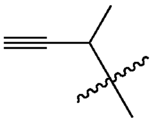).

The "$C_{2-4}$ alkynyl" in the present disclosure refers to a straight or branched chain alkynyl with 2-4 carbon atoms comprising triple bonds.

The "deuterium" in the present disclosure refers to a single deuterium atom, with the symbol $^2H$ or D. Taking hydrogen atom as an example, its natural abundance, for example, is in the form of about 99.985% protium and about 0.015% deuterium; the non-natural abundance of deuterium is about 95% deuterium.

The term "deuterated substance" or "deuterated group" in the present disclosure refers to a compound or group produced when the hydrogen atom in the structure of the compound or the chemical group is partially or completely replaced by its isotope deuterium.

The term "deuterated $C_{1-3}$ alkyl" in the present disclosure refers to a group obtained by partially or completely replacing the hydrogen atom in the structure of "$C_{1-3}$ alkyl" with its isotope deuterium, "$C_{1-3}$ alkyl" is as defined above.

The term "deuterated $C_{1-3}$ alkoxy" in the present disclosure refers to a group obtained by partially or completely replacing the hydrogen atom in the structure of "$C_{1-3}$ alkoxy" with its isotope deuterium, "$C_{1-3}$ alkoxy" is as defined above.

The term "deuterated methyl" in the present disclosure refers to a group obtained by partially or completely replacing the hydrogen atom in the structure of the methyl with its isotope deuterium. $CD_3$ is a group obtained by completely replacing the hydrogen atom in the structure of the methyl with its isotope deuterium (deuterium with non-natural abundance of about 95%).

The term "deuterated methoxy" in the present disclosure refers to a group obtained by partially or completely replacing the hydrogen atom in the structure of the methoxy with its isotope deuterium. $CD_3$-O— is a group obtained by completely replacing the hydrogen atom in the structure of the methyl-O— with its isotope deuterium (deuterium with a non-natural abundance of about 95%).

The term "deuterated ethyl" in the present disclosure refers to a group obtained by partially or completely replacing the hydrogen atom in the structure of the ethyl with its isotope deuterium. $CD_3$-$CD_2$- is a group obtained by completely replacing the hydrogen atom in the structure of the ethyl-O— with its isotope deuterium (deuterium with non-natural abundance of about 95%).

The "aliphatic heterocycle" in the present disclosure refers to a stable 4- to 7-membered monocycle, these heterocycles can be saturated or partially unsaturated, and are composed of carbon atoms and 1 to 7 heteroatoms optionally selected from N, O and S, preferably 4- to 6-membered heterocyclic alkyl or heterocyclic alkenyl. The "aliphatic heterocycle" can be connected to the rest of the molecule via a carbon atom and through a single bond; in the "aliphatic heterocycle" group containing one or more nitrogen atoms, the connection point can be a carbon or nitrogen atom; or, it can be fused with the rest of the molecule; as long as the valency allows. Examples of the heterocyclic alkyl are: pyrrolidinyl, tetrahydrofuranyl, tetrahydropyranyl, tetrahydrothienyl, tetrahydropyridyl, tetrahydropyrrolyl, azetidine, thiazolidyl, zolidinyl, piperidyl, morpholinyl, thiomorpholinyl, piperazinyl, azacycloheptane, diazacycloheptane, oxyazacycloheptane, dioxolanyl, dioxanyl, etc. The preferred heterocyclic group is 1,3-dioxolanyl and 1,4-dioxanyl.

Unless otherwise specified, all technical and scientific terms used herein have the standard meaning in the field to which the claimed subject matter belongs. If there are multiple definitions of a certain term, the definition herein shall prevail.

It should be understood that singular forms such as "a" used in the present disclosure include plural references, unless otherwise specified. In addition, the term "include" is open-ended and not closed, that is, including the content specified in the present disclosure, but does not exclude other aspects.

Unless otherwise specified, the present disclosure uses the conventional methods of mass spectrometry and elemental analysis, and the steps and conditions can be referred to the conventional operating steps and conditions in the art.

Unless otherwise specified, the present disclosure uses standard nomenclature and standard laboratory procedures and techniques of analytical chemistry, organic synthetic chemistry, and optics. In some cases, standard techniques are used for chemical synthesis, chemical analysis, and light-emitting device performance testing.

In addition, it should be noted that, unless otherwise specified, the expression " . . . independently" used in the present disclosure should be broadly understood, which refers to that the described individuals are independent of each other and can be the same or different specific groups independently. In more detail, the expression " . . . independently" can refer to either that the specific options expressed between the same symbols in different groups do not affect each other, or that the specific options expressed between the same symbols in the same groups do not affect each other.

It can be understood by those skilled in the art that, according to the convention used in the art, the "  "

used in the structural formula of the group described in the present disclosure refers to that the corresponding group is linked to other fragments and groups in the compound through the site.

The above preferred conditions can be combined arbitrarily to obtain preferred embodiments of the present disclosure without violating common knowledge in the art.

The reagents and raw materials used in the present disclosure are all commercially available.

The positive progressive effect of the present disclosure is that: the deuterated compound provided in the present disclosure maintains the activity of inhibiting tumor cells and tumor stem cells, and significantly prolongs the degradation function of human liver microsomes on the compound in vitro, such that the half-life period is significantly prolonged, which provides a safer and more reliable candidate for developing new anti-tumor drugs. Specifically, the representative compounds can all achieve: (1) better inhibitory activity against all nine representative tumor cell lines; (2) significantly prolonged half-life and enhanced metabolic stability; (3) inhibition of breast cancer stem cells and ability to self-renewal, indicating that the compound has the ability to kill tumor stem cells; and (4) significantly slower growth rate of tumor volume in all treatment groups compared to the solvent control group.

BRIEF DESCRIPTION OF THE DRAWINGS

FIG. 1 is the inhibition experiment of 7 compounds in Example 44 on the formation of tumor stem cell Sphere at 50 nM concentration.

DETAILED DESCRIPTION OF THE PREFERRED EMBODIMENT

The present disclosure will be further described below with reference to embodiments, but the present disclosure is not therefore limited to the scope of the embodiments. Experimental methods without specific conditions in the following embodiments are selected according to conventional methods and conditions, or according to the commercial specification. Any technology implemented based on the above-mentioned elements of the present disclosure is within the scope of the present disclosure.

Unless otherwise specified, the reagents used in the experiment were purchased from Beijing Ouhe Technology Co., Ltd., Beijing J&K Scientific Co., Ltd., Acros Organics, Alfa Aesar, Sigma-Aldrich and TCI, and were used directly without purification. The solvents used in the experiment were mainly purchased from Beijing Chemical Works and Xilong Chemical Co., Ltd. were used directly without process, except THF and DMF, which were further processed by the solvent purification system of Vacuum atmospheres company. $GF_{254}$ silica gel plates for thin layer chromatography, $GF_{254}$ silica gel thick preparation plates and silica gel powder for column chromatography (60-100 mesh, 160-200 mesh, 200-300 mesh) were purchased from Qingdao Haiyang Chemical Factory.

HPLC-MS analyzer: HPLC analyzer was Agilent 1100 HPLC system, Agilent G1312A pump, Agilent G1314A UV detector, Agilent G1313A autosampler, Agilent G1316A column heater and diverter valve. Chromatographic column was a Kromasil C18 column (4.6 m, 4.6 mm×50 mm), purchased from DIKMA. The mobile phase was acetonitrile containing 0.05% HCOOH and water. Linear gradient elution was 5:95 (v:v) acetonitrile-$H_2O$ to 95:5 (v:v) acetonitrile-$H_2O$ for 5 minutes at a flow rate of 1 mL/min. UV detection wavelength was 254 nm. ThermoFinnigan LCQ-Advantage mass spectrometer, 5% of the eluate was diverted into the mass spectrometer, and positive or negative ion scanning and electron spray ionization (ESI) were adopted. It was mainly used for reaction monitoring and preliminary determination of compound purity.

UPLC-MS analyzer: Acquity UPLC-MS system from Waters Company, including binary solvent manager, sample manager, chromatographic column manager, PDA detector and SQ mass spectrometer detector. The chromatographic column was Acquity UPLC® BEH C18 column (1.7 m, 2.1 mm×50 mm) from Waters Company. The mobile phase was acetonitrile containing 0.05% HCOOH and water. Linear gradient elution was 5:95 (v:v) acetonitrile-$H_2O$ to 95:5 (v:v) acetonitrile-$H_2O$ for 3 minutes at a flow rate of 0.3 mL/min. UV detection wavelength was 254 nm. SQ mass spectrometer adopted positive or negative ion scanning and electron spray ionization (ESI). It was mainly used for reaction monitoring and preliminary determination of compound purity.

HPLC analyzer: Agilent 1260 HPLC system, Agilent G1311C quadruple pump, Agilent G4212B UV detector, Agilent G1367E high-performance autosampler, Agilent G1316A column heater. Chiral analytical column: DAICEL CHIRALPAK AD-H, 250×4.6 mm, 5 μM (manufactured by DAICEL, Japan). The mobile phase was hexane/isopropanol with isocratic elution. UV detection wavelength was 254 nm. It was mainly used for the optical purity analysis of the target compound.

High resolution mass spectrometer: Agilent LC/MSD TOF system. Chromatographic column: Agilent ZORBAX SB-C18 (Rapid resolution, 3.5 m, 2.130 mm). Mobile phase: MeOH:$H_2O$=75:25 (v:v), containing 5 mmol/L of formic acid, isocratic elution. The time was 5 min; the flow rate was 0.40 mL/min. Mass spectrometer detection adopted positive ion scanning and electron spray ionization (ESI). It was mainly used determine the accurate molecular weight of the target compound.

NMR: Varian Mercury 300 MHz, 400 MHz, 500 MHz, 600 MHz and Bruker Avance 400 MHz and the solvent was $CDCl_3$, DMSO-$d_6$, acetone-$d_6$ or methanol-$d_4$.

Melting point apparatus: Yanaco micro melting point apparatus, OptiMelt melting point apparatus, all uncalibrated.

Embodiment 1 (S)-2-chloro-N-[3-[2-(diethylamino)-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy)benzamide (Compound 1)

Preparation of 5-chloro-2,4-dinitrobenzoic acid (Intermediate 42): 3-chlorobenzoic acid (63.9 mmol) was dissolved in 120 mL of concentrated sulfuric acid, and stirred at room temperature, and potassium nitrate (163.2 mmol) was added in batches over 15 min. The reaction mixture was reacted sequentially at 80° C. for 30 min, 110° C. for 2 h and 120° C. for 2 h. The reaction mixture was poured into 660 g of ice water and filtered, and the resulting white solid was recrystallized with a mixture of ethanol and water to obtain 8.08 g of pale yellow crystal, 51.3% yield. $^{1}H$ NMR (400 MHz, DMSO-$d_6$) δ 14.21 (brs, 1H), 8.85 (s, 1H), 8.28 (s, 1H). $^{13}C$ NMR (100 MHz, DMSO-$d_6$) δ 163.78, 147.95, 145.70, 132.86, 132.06, 130.52, 122.05.

Preparation of 5-(3,5-dimethylphenoxy)-2,4-dinitrobenzoic acid (Intermediate 43): Intermediate 42 (20.0 mmol), 3,5-dimethylphenol (21.2 mmol) and sodium bicarbonate (42.4 mmol) were mixed in 20 mL of water, and the reaction mixture was refluxed and reacted for 2 h. The reaction mixture was monitored by HPLC-MS, diluted with 30 mL of water, and its pH was adjusted to acidity with hydrochloric acid, then it was filtered and dried to obtain 5.50 g of off-white solid, 82.7% yield. $^{1}H$ NMR (400 MHz, DMSO-$d_6$) δ 8.76 (s, 1H), 7.14 (s, 1H), 6.99 (s, 1H), 6.89 (s, 2H), 2.30 (s, 6H). $^{13}C$ NMR (100 MHz, DMSO-$d_6$) δ 164.56, 153.58, 153.56, 140.60, 140.38, 139.33, 135.32, 127.78, 122.66, 118.76, 117.64, 20.78.

Preparation of (S)-2-[5-(3,5-dimethylphenoxy)-2,4-dinitrobenzamido]butanedioic acid dimethyl ester (Intermediate 44): Intermediate 43 (10.0 mmol) was dissolved in 10 mL of DCM, and 50 μL of DMF and oxalyl chloride (30.0 mmol) were added sequentially, and the reaction mixture was refluxed and reacted for 1 h. The reaction solution was concentrated and the residue was dissolved by DCM, which was added dropwise to a mixture of L-aspartic acid dimethyl ester hydrochloride (10.1 mmol), triethylamine (22.0 mmol) and 20 mL of DCM, and the reaction mixture was reacted at room temperature for 15 min. The reaction mixture was diluted with about 100 mL of DCM, washed with 1 M dilute hydrochloric acid, saturated sodium bicarbonate solution and water in turn, and the organic phase was separated, and concentrated to obtain 4.23 g of reddish brown oil, 89.0% yield. $^{1}H$ NMR (400 MHz, DMSO-$d_6$) δ 9.31 (d, J=7.9 Hz, 1H), 8.84 (s, 1H), 7.00 (s, 1H), 6.97 (s, 1H), 6.90 (s, 2H), 4.74 (dd, J=13.7, 7.1 Hz, 1H), 3.61 (s, 3H), 3.55 (s, 3H), 2.88 (dd, J=16.5, 5.7 Hz, 1H), 2.80 (dd, J=16.5, 7.3 Hz, 1H), 2.30 (s, 6H).

Preparation of (S)-2-[8-amino-7-(3,5-dimethylphenoxy)-2,5-dioxo-2,3,4,5-tetrahydro-1H-benzo[e][1,4]diazepin-3-yl]acetic acid methyl ester (Intermediate 45): Intermediate 44 (5.0 mmol) was dissolved in 80 mL of glacial acetic acid, 6.0 g of iron powder was added and the reaction mixture was reacted at 90° C. for 5 h. The reaction mixture was diluted with DCM, filtered, and the filtrate was concentrated, and eluted with petroleum ether/ethyl acetate through silica gel column chromatography to obtain 1.25 g of light yellow solid, 65.0% yield. $^{1}H$ NMR (300 MHz, DMSO-$d_6$) δ 10.23 (s, 1H), 8.16 (d, J=5.0 Hz, 1H), 7.00 (s, 1H), 6.74 (s, 1H), 6.59 (s, 2H), 6.42 (s, 1H), 5.75 (s, 2H), 4.04 (dt, J=8.8, 5.5 Hz, 1H), 3.58 (s, 3H), 2.85 (dd, J=17.0, 8.8 Hz, 1H), 2.68 (dd, J=17.0, 5.6 Hz, 1H), 2.23 (s, 6H).

Preparation of (S)-2-[8-amino-7-(3,5-dimethylphenoxy)-2,5-dioxo-2,3,4,5-tetrahydro-1H-benzo[e][1,4]diazepin-3-yl]]-N,N-diethylacetamide (Intermediate 46): Intermediate 45 (2.0 mmol) and lithium hydroxide (6.0 mmol) were mixed, 20 mL of water and 20 mL of THF were added and the reaction mixture was reacted at room temperature for 30 min. The THF was concentrated under vacuum, and the pH of the mixture was adjusted to acidity with 1 M hydrochloric acid, and the resulting precipitation was filtered and dried. The resulting white solid was mixed with DIC (4.0 mmol) and HOSu (4.0 mmol) in 20 mL of THF, and the reaction mixture was reacted at room temperature for 12 h. Diethylamine (6.0 mmol) was added and the reaction was continued for 1 h. The reaction mixture was eluted with DCM/ethyl acetate through silica gel column chromatography to obtain 508 mg of light yellow solid, 59.8% yield. $^{1}H$ NMR (400 MHz, DMSO-$d_6$) δ 10.11 (d, J=2.1 Hz, 1H), 8.09 (s, 1H), 7.01 (d, J=3.5 Hz, 1H), 6.74 (s, 1H), 6.60 (s, 2H), 6.43 (d, J=2.9 Hz, 1H), 5.72 (s, 2H), 4.14 (dd, J=5.4, 2.7 Hz, 1H), 3.32-3.16 (m, 4H), 2.96 (dd, J=16.1, 8.6 Hz, 1H), 2.55 (dd, J=16.4, 4.8 Hz, 1H), 2.24 (s, 6H), 1.16 (t, J=7.0 Hz, 3H), 0.98 (t, J=7.0 Hz, 3H). $^{13}C$ NMR (100 MHz, DMSO-$d_6$) δ 170.79, 168.09, 167.54, 157.04, 144.26, 139.27, 139.16, 134.30, 124.62, 120.39, 115.29, 113.73, 105.53, 49.14, 41.37, 31.35, 20.96, 13.94, 13.06.

Preparation of 2-chloro-3,4,5-tris(trideuteromethoxy)benzoic acid (Intermediate 47): gallic acid (23.51 mmol) and potassium carbonate (188.10 mmol) were dissolved in 20 mL of DMF, and deuterated iodomethane (117.56 mmol) was added and the reaction mixture was reacted at 35° C.

overnight. The reaction mixture was evaporated, dissolved with DCM, washed three times with water, separated to obtain the organic phase, dried and concentrated to obtain 5.34 g of crude product, 95.4% yield. The above intermediate (3.0 mmol) and NCS (3.6 mmol) were dissolved in 5 mL of DMF and the reaction mixture was reacted at room temperature overnight. The reaction solution was evaporated, and eluted with petroleum ether/ethyl acetate through silica gel column chromatography to obtain 292 mg of crude product, 53.2% yield. The above intermediate (1.07 mmol) and lithium hydroxide (5.37 mmol) were dissolved in 8 mL of THF and 4 mL of water, and the reaction mixture was reacted at room temperature overnight. The THF was concentrated under vacuum, the resulting mixture was diluted with water, and its pH was adjusted to acidity with 1 M hydrochloric acid, and the resulting precipitation was filtered and dried to obtain 260 mg of white solid, 94.9% yield. $^{1}$H NMR (400 MHz, DMSO-$d_6$) δ 13.30 (s, 1H), 7.19 (s, 1H). $^{13}$C NMR (100 MHz, DMSO-$d_6$) δ 166.38, 151.59, 149.74, 145.14, 126.75, 118.39, 109.41.

Title compound (1) Intermediate 47 (0.5 mmol) was dissolved in 5 mL of DCM, and L of DMF and oxalyl chloride (1.5 mmol) were added in turn. The reaction mixture was reacted at 40° C. for 1 h. The reaction solution was concentrated and recrystallized with 50 mL of petroleum ether. The resulting white solid was mixed with Intermediate 46 (0.2 mmol) and pyridine (0.6 mmol) in 2 mL of THF, and the reaction mixture was refluxed and reacted for 1 h. The reaction mixture was eluted with DCM/MeOH through silica gel column chromatography to obtain 113 mg of yellow solid, 85.5% yield. $^{1}$H NMR (400 MHz, DMSO-$d_6$) δ 10.38 (s, 1H), 10.23 (s, 1H), 8.52 (d, J=5.4 Hz, 1H), 8.00 (s, 1H), 7.15 (s, 1H), 6.83 (s, 1H), 6.81 (s, 1H), 6.68 (s, 2H), 4.18 (dt, J=8.9, 5.2 Hz, 1H), 3.32-3.17 (m, 4H), 2.98 (dd, J=16.2, 8.6 Hz, 1H), 2.60 (dd, J=16.1, 5.0 Hz, 1H), 2.25 (s, 6H), 1.17 (t, J=7.0 Hz, 3H), 0.99 (t, J=7.0 Hz, 3H). $^{13}$C NMR (100 MHz, DMSO-$d_6$) δ 170.79, 167.90, 166.79, 164.93, 156.20, 151.90, 149.32, 144.27, 143.86, 139.37, 132.73, 132.66, 131.58, 125.42, 122.93, 119.15, 116.35, 116.25, 115.53, 107.92, 49.01, 41.36, 31.24, 20.88, 13.91, 13.05.

Embodiment 2 (S)-2-chloro-N-[3-[2-(diethylamino)-2-oxoethyl]-7-(3,5-dimethylphenoxy)-2,5-dioxo-2,3,4,5-tetrahydro-1H-benzo[e][1,4]diazepin-8-yl]-3,5-dimethoxy-4-(trideuteromethoxy)benzamide (Compound 2)

Preparation of 2-chloro-3,5-dimethoxy-4-(trideuteromethoxy)benzoic acid (Intermediate 48): syringic acid (2.52 mmol) and potassium carbonate (10.10 mmol) were dissolved in 5 mL of DMF, and deuterated iodomethane (5.05 mmol) was added and the reaction mixture was reacted at 35° C. overnight. It was detected that a small amount of substrate had not reacted completely, and the reaction was continued for 9 h with the addition of deuterated iodomethane (5.05 mmol), and the reaction was completed. The reaction solution was concentrated, dissolved with DCM, washed three times with water, separated to obtain the organic phase, dried and concentrated to obtain 544 mg of intermediate product, 93.0% yield. The above intermediate (2.34 mmol) and NCS (2.81 mmol) were dissolved in 5 mL of DMF and the reaction mixture was reacted at room temperature overnight. The reaction mixture was eluted with DCM through silica gel column chromatography to obtain 300 mg of intermediate product, 48.2% yield. The above intermediate (1.13 mmol) and lithium hydroxide (5.64 mmol) were dissolved in 8 mL of THF and 4 mL of water, and the reaction mixture was reacted at room temperature for 4 h. The THF was concentrated under vacuum, the resulting mixture was diluted with water, and its pH was adjusted to acidity with 1 M hydrochloric acid, and the resulting precipitation was filtered and dried to obtain 273 mg of white solid, 97.5% yield. $^{1}$H NMR (400 MHz, DMSO-$d_6$) δ 13.28 (s, 1H), 7.20 (s, 1H), 3.84 (s, 3H), 3.80 (s, 3H). $^{13}$C NMR (100 MHz, DMSO-$d_6$) δ 166.54, 151.73, 149.93, 145.36, 126.81, 118.74, 109.64, 61.01, 56.22.

According to the synthesis method of the compound 1 in Embodiment 1, intermediate 46 (0.2 mmol) and intermediate 48 (0.5 mmol) were used to prepare the title compound (2). $^{1}$H NMR (400 MHz, DMSO-$d_6$) δ 10.38 (s, 1H), 10.23 (s, 1H), 8.53 (d, J=5.3 Hz, 1H), 8.00 (s, 1H), 7.16 (s, 1H), 6.84 (s, 1H), 6.81 (s, 1H), 6.68 (s, 2H), 4.18 (dt, J=8.5, 5.3 Hz, 1H), 3.81 (s, 3H), 3.77 (s, 3H), 3.30-3.19 (m, 4H), 2.98 (dd, J=16.3, 8.4 Hz, 1H), 2.60 (dd, J=16.3, 4.8 Hz, 1H), 2.25 (s, 6H), 1.17 (t, J=6.9 Hz, 3H), 0.99 (t, J=7.0 Hz, 3H). $^{13}$C NMR (100 MHz, DMSO-$d_6$) δ 170.79, 167.91, 166.80, 164.93, 156.21, 151.91, 149.34, 144.28, 143.90, 139.38, 132.74, 132.68, 131.59, 125.42, 122.94, 119.17, 116.35, 116.31, 115.54, 107.98, 61.01, 56.22, 49.02, 41.37, 31.25, 20.88, 13.92, 13.06.

Embodiment 3 (S)-2-chloro-N-[3-[2-(diethylamino)-2-oxoethyl]-7-(3,5-dimethylphenoxy)-2,5-dioxo-2,3,4,5-tetrahydro-1H-benzo[e][1,4]diazepin-8-yl]-3,5-dimethoxy-4-(trideuteromethyl)benzamide (Compound 3)

Preparation of 2-chloro-3,5-dimethoxy-4-(trideuteromethyl)benzoic acid (Intermediate 49): potassium tert-butoxide (4.38 mmol) dissolved in 10 mL of anhydrous THE and stirred, and a solution of 3,5-dimethylbenzoic acid (1.10 mmol) in 10 mL of anhydrous THF was added under argon at −78° C. Butyllithium (4.38 mmol, 2.5 M in hexanes) was added, and the reaction mixture was reacted at −78° C. for 40 min. Deuterated iodomethane (2.20 mmol) was added and the reaction was continued at −78° C. for 1 h. The reaction mixture was heated to room temperature, quenched with 6 mL of saturated ammonium chloride solution, washed twice with 10 mL of ether, and separated to obtain the aqueous phases, the pH of the aqueous phase was adjusted to acidity with 2 M hydrochloric acid, and a white precipitate was precipitated, extracted twice with ether and separated the organic phase, then it was dried and concentrated under vacuum to obtain 202 mg of an intermediate through reversed-phase column chromatography, 61.59% yield. According to the synthesis method of the intermediate 47 in Embodiment 1, the above product was chlorinated to obtain intermediate 49.

According to the synthesis method of the compound 1 in Embodiment 1, intermediate 46 (0.2 mmol) and intermediate 49 (0.5 mmol) were used to prepare the title compound (3). $^{1}$H NMR (400 MHz, DMSO-$d_6$) δ 10.39 (s, 1H), 10.22 (s, 1H), 8.52 (d, J=5.5 Hz, 1H), 7.99 (s, 1H), 7.17 (s, 1H), 6.81 (s, 1H), 6.75 (s, 1H), 6.68 (s, 2H), 4.19 (dt, J=9.0, 5.3 Hz, 1H), 3.75 (s, 3H), 3.72 (s, 3H), 3.30-3.19 (m, 4H), 2.98 (dd, J=16.3, 8.6 Hz, 1H), 2.60 (dd, J=16.2, 4.9 Hz, 1H), 2.25 (s, 6H), 1.17 (t, J=7.0 Hz, 3H), 0.99 (t, J=7.0 Hz, 3H). $^{13}$C NMR (100 MHz, DMSO-$d_6$) δ 170.79, 167.91, 166.79, 165.17, 156.49, 156.21, 154.23, 144.28, 139.36, 134.76, 132.74, 132.69, 125.38, 122.98, 122.26, 119.25, 116.27, 115.94, 115.66, 106.56, 60.26, 55.95, 49.01, 41.36, 31.24, 20.87, 13.91, 13.05.

Embodiment 4 (S)-2-bromo-N-[3-[2-(diethylamino)-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy)benzamide (Compound 4)

Preparation of 2-bromo-3,4,5-tris(trideuteromethoxy) benzoic acid (Intermediate 50): according to the synthesis method of the intermediate 47 in Embodiment 1, the corresponding reagents and NBS (3.6 mmol) were used to prepare it. $^1$H NMR (400 MHz, DMSO-$d_6$) δ 13.33 (s, 1H), 7.17 (s, 1H). $^{13}$C NMR (100 MHz, DMSO-$d_6$) δ 167.12, 152.29, 150.64, 144.67, 129.47, 109.58, 107.02.

According to the synthesis method of the compound 1 in Embodiment 1, intermediate 46 (0.2 mmol) and intermediate 50 (0.5 mmol) were used to prepare the title compound (4). $^1$H NMR (400 MHz, DMSO-$d_6$) δ 10.39 (s, 1H), 10.22 (s, 1H), 8.52 (d, J=4.9 Hz, 1H), 8.02 (s, 1H), 7.16 (s, 1H), 6.82 (s, 2H), 6.68 (s, 2H), 4.18 (m, 1H), 3.32-3.13 (m, 4H), 2.99 (dd, J=16.1, 8.5 Hz, 1H), 2.59 (dd, J=16.1, 4.2 Hz, 1H), 2.25 (s, 6H), 1.17 (t, J=6.7 Hz, 3H), 0.99 (t, J=6.8 Hz, 3H). $^{13}$C NMR (100 MHz, DMSO-$d_6$) δ 171.23, 168.35, 167.25, 166.37, 156.66, 152.97, 150.70, 144.74, 144.00, 139.80, 134.38, 133.24, 133.08, 125.85, 123.36, 119.56, 116.86, 115.97, 108.69, 106.10, 49.45, 41.81, 31.68, 21.33, 14.36, 13.50.

Embodiment 5 (S)-2-bromo-N-[3-[2-[bis(pentadeuteroethyl)amino]-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy) benzamide (Compound 5)

Preparation of (S)-2-[8-amino-7-(3,5-dimethylphenoxy)-2,5-dioxo-2,3,4,5-tetrahydro-1H-benzo[e][1,4]diazepin-3-yl]]-N,N-bis(pentadeuteroethyl)acetamide (Intermediate 51): according to the synthesis method of the intermediate 46 in Embodiment 1, intermediate 45 (2.0 mmol) and deuterated diethylamine (6.0 mmol) were used to prepare it. $^1$H NMR (400 MHz, DMSO-$d_6$) δ 10.10 (s, 1H), 8.09 (d, J=4.8 Hz, 1H), 7.00 (s, 1H), 6.74 (s, 1H), 6.60 (s, 2H), 6.42 (s, 1H), 5.72 (s, 2H), 4.19-4.08 (m, 1H), 2.95 (dd, J=16.2, 8.7 Hz, 1H), 2.58-2.52 (m, 1H), 2.24 (s, 6H). $^{13}$C NMR (100 MHz, DMSO-$d_6$) δ 170.80, 168.04, 167.53, 157.04, 144.26, 139.25, 139.14, 134.29, 124.60, 120.38, 115.29, 113.70, 105.49, 49.12, 31.31, 20.95.

According to the synthesis method of the compound 1 in Embodiment 1, intermediate 51 (0.2 mmol) and intermediate 50 (0.5 mmol) were used to prepare the title compound 5. $^1$H NMR (400 MHz, DMSO-$d_6$) δ 10.38 (s, 1H), 10.21 (s, 1H), 8.52 (d, J=4.3 Hz, 1H), 8.02 (s, 1H), 7.16 (s, 1H), 6.82 (s, 2H), 6.68 (s, 2H), 4.20-4.15 (m, 1H), 2.98 (dd, J=16.0, 8.6 Hz, 1H), 2.59 (dd, J=16.1, 3.8 Hz, 1H), 2.25 (s, 6H). $^{13}$C NMR (100 MHz, DMSO-$d_6$) δ 170.74, 167.86, 166.76, 165.86, 156.19, 152.49, 150.23, 144.26, 143.54, 139.31, 133.89, 132.73, 132.61, 125.36, 122.88, 119.09, 116.36, 115.50, 108.24, 105.61, 48.97, 31.17, 20.84.

Embodiment 6 (S)-2-chloro-N-[3-[2-[bis(pentadeuteroethyl)amino]-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy) benzamide (Compound 6)

According to the synthesis method of the compound 1 in Embodiment 1, intermediate 51 (0.2 mmol) and intermediate 47 (0.5 mmol) were used to prepare the title compound (6). $^1$H NMR (400 MHz, $CDCl_3$) δ 9.17 (s, 1H), 8.48 (s, 1H), 8.14 (s, 1H), 7.41 (s, 1H), 7.23 (s, 1H), 7.11 (d, J=4.9 Hz, 1H), 6.80 (s, 1H), 6.66 (s, 2H), 4.51 (dd, J=11.7, 5.7 Hz, 1H), 3.07 (dd, J=15.7, 7.4 Hz, 1H), 2.69 (dd, J=15.6, 4.8 Hz, 1H), 2.29 (s, 6H). $^{13}$C NMR (100 MHz, $CDCl_3$) δ 171.33, 168.45, 168.22, 164.15, 155.94, 152.53, 150.09, 145.97, 143.43, 140.18, 133.44, 132.52, 128.98, 126.39, 121.26, 119.10, 117.65, 116.70, 112.54, 109.64, 49.86, 31.57, 21.40.

Embodiment 7 (S)-2-bromo-N-[3-[2-[bis(pentadeuteroethyl)amino]-2-oxoethyl]-7-(3,5-dimethylphenoxy)-2,5-dioxo-2,3,4,5-tetrahydro-1H-benzo[e][1,4]diazepin-8-yl]-3,4,5-trimethoxybenzamide (Compound 7)

Preparation of 2-bromo-3,4,5-trimethoxybenzoic acid (Intermediate 52): 3,4,5-trimethoxybenzoic acid (10.0 mmol) was dissolved in 100 mL of chloroform, and bromine water (20.0 mmol) was added and the reaction mixture was refluxed and reacted for 5 h. The reaction solution was washed with saturated sodium thiosulfate solution and water in turn, the organic phase was separated and evaporated, and recrystallized with water and ethanol to obtain 2.74 g of white solid, 94.2% yield. $^1$H NMR (400 MHz, DMSO-$d_6$) δ 13.31 (brs, 1H), 7.17 (s, 1H), 3.83 (s, 3H), 3.82 (s, 3H), 3.78 (s, 3H).

According to the synthesis method of the compound 1 in Embodiment 1, intermediate 51 (0.2 mmol) and intermediate 52 (0.5 mmol) were used to prepare the title compound (7). $^1$H NMR (400 MHz, DMSO-$d_6$) δ 10.37 (s, 1H), 10.21 (s, 1H), 8.51 (d, J=5.3 Hz, 1H), 8.01 (s, 1H), 7.15 (s, 1H), 6.82 (s, 1H), 6.81 (s, 1H), 6.68 (s, 2H), 4.18 (dt, J=8.4, 5.3 Hz, 1H), 3.80 (s, 3H), 3.79 (s, 3H), 3.77 (s, 3H), 2.98 (dd, J=16.3, 8.6 Hz, 1H), 2.59 (dd, J=16.3, 4.9 Hz, 2H), 2.25 (s, 6H). $^{13}$C NMR (100 MHz, DMSO-$d_6$) δ 170.77, 167.88, 166.79, 165.88, 156.20, 152.52, 150.28, 144.27, 143.60, 139.34, 133.94, 132.75, 132.63, 125.38, 122.91, 119.12, 116.37, 115.53, 108.30, 105.68, 60.86, 60.74, 56.22, 49.00, 31.19, 20.86.

Embodiment 8 (S)-2-chloro-N-[3-[2-[bis(pentadeuteroethyl)amino]-2-oxoethyl]-7-(3,5-dimethylphenoxy)-2,5-dioxo-2,3,4,5-tetrahydro-1H-benzo[e][1,4]diazepin-8-yl]-3,4,5-trimethoxybenzamide (Compound 8)

Preparation of 2-chloro-3,4,5-trimethoxybenzoic acid (Intermediate 53): 3,4,5-trimethoxybenzoic acid (10.0 mmol) was dissolved in 50 mL of chloroform and 25 mL of glacial acetic acid, and NCS (10.0 mmol) was added and the reaction mixture was refluxed and reacted for 5 h. The reaction solution was concentrated, and recrystallized with water and ethanol to obtain 1.80 g of white solid, 73.1% yield. $^1$H NMR (400 MHz, DMSO-$d_6$) δ 13.31 (s, 1H), 7.20 (s, 1H), 3.84 (s, 3H), 3.83 (s, 3H), 3.80 (s, 3H). $^{13}$C NMR (100 MHz, DMSO-$d_6$) δ 166.32, 151.58, 149.74, 145.13, 126.79, 118.36, 109.42, 60.91, 60.79, 56.15.

According to the synthesis method of the compound 1 in Embodiment 1, intermediate 51 (0.2 mmol) and intermediate 53 (0.5 mmol) were used to prepare the title compound (8). $^1$H NMR (400 MHz, DMSO-$d_6$) δ 10.38 (s, 1H), 10.23 (s, 1H), 8.52 (d, J=5.4 Hz, 1H), 8.00 (s, 1H), 7.16 (s, 1H), 6.84 (s, 1H), 6.81 (s, 1H), 6.68 (s, 2H), 4.18 (dt, J=8.9, 5.2 Hz, 1H), 3.81 (s, 3H), 3.80 (s, 3H), 3.77 (s, 3H), 2.97 (dd, J=16.2, 8.5 Hz, 1H), 2.59 (dd, J=16.3, 5.0 Hz, 1H), 2.25 (s, 6H). $^{13}$C NMR (100 MHz, DMSO-$d_6$) δ 170.82, 167.92, 166.83, 164.95, 156.23, 151.94, 149.38, 144.31, 143.93, 139.41, 132.75, 132.68, 131.64, 125.44, 122.97, 119.20, 116.36, 116.32, 115.58, 107.99, 61.04, 60.82, 56.24, 49.03, 31.23, 20.90.

Embodiment 9 (S)-2-[8-(2-chloro-3,4,5-trimethoxybenzamido)-7-(3,5-dimethylphenoxy)-2,5-dioxo-2,3,4,5-tetrahydro-1H-benzo[e][1,4]diazepin-3-yl]acetic acid trideuteromethyl ester (Compound 9)

Preparation of (S)-2-[8-amino-7-(3,5-dimethylphenoxy)-2,5-dioxo-2,3,4,5-tetrahydro-1H-benzo[e][1,4]diazepin-3-yl]acetic acid trideuteromethyl ester (Intermediate 54): according to the synthesis method of the intermediate 46 in Embodiment 1, intermediate 45 (2.0 mmol) and deuterated methanol (6.0 mmol) were used to prepare it. $^{1}$H NMR (300 MHz, DMSO-$d_6$) δ 10.21 (s, 1H), 8.15 (d, J=5.0 Hz, 1H), 7.00 (s, 1H), 6.72 (s, 1H), 6.58 (s, 2H), 6.41 (s, 1H), 5.74 (s, 2H), 4.02 (dt, J=8.8, 5.5 Hz, 1H), 2.83 (dd, J=17.0, 8.8 Hz, 1H), 2.67 (dd, J=17.0, 5.5 Hz, 1H), 2.22 (s, 6H).

According to the synthesis method of the compound 1 in Embodiment 1, intermediate 54 (0.2 mmol) and intermediate 53 (0.5 mmol) were used to prepare the title compound (9). $^{1}$H NMR (400 MHz, DMSO-$d_6$) δ 10.52 (s, 1H), 10.25 (s, 1H), 8.59 (d, J=4.8 Hz, 1H), 8.03 (s, 1H), 7.16 (s, 1H), 6.84 (s, 1H), 6.82 (s, 1H), 6.68 (s, 2H), 4.12 (dt, J=8.1, 5.4 Hz, 1H), 3.81 (s, 3H), 3.80 (s, 3H), 3.77 (s, 3H), 2.88 (dd, J=16.9, 8.8 Hz, 1H), 2.73 (dd, J=17.2, 5.4 Hz, 1H), 2.25 (s, 6H). $^{13}$C NMR (100 MHz, DMSO-$d_6$) δ 170.58, 170.45, 166.73, 164.97, 156.18, 151.94, 149.37, 144.37, 143.93, 139.40, 132.87, 132.45, 131.61, 125.47, 122.68, 119.23, 116.39, 116.30, 115.50, 108.00, 61.03, 60.79, 56.23, 48.60, 32.49, 20.87.

Embodiment 10 (S)-2-chloro-N-[3-[2-(4,4-difluoropiperidin-1-yl)-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy)benzamide (Compound 10)

Preparation of (S)-8-amino-3-[2-(4,4-difluoropiperidin-1-yl)-2-oxoethyl]-7-(3,5-methylphenoxy)-3,4-dihydro-1H-benzo[e][1,4]diazepin-2,5-dione (Intermediate 55): according to the synthesis method of the intermediate 46 in Embodiment 1, intermediate 45 (2.0 mmol) and 4.4-difluoropiperidine (4.0 mmol) were used to prepare it.

According to the synthesis method of the compound 1 in Embodiment 1, intermediate 55 (0.2 mmol) and intermediate 47 (0.5 mmol) were used to prepare the title compound (10). $^{1}$H NMR (400 MHz, DMSO-$d_6$) δ 10.43 (s, 1H), 10.22 (s, 1H), 8.51 (d, J=5.1 Hz, 1H), 8.02 (s, 1H), 7.17 (s, 1H), 6.84 (s, 1H), 6.82 (s, 1H), 6.68 (s, 2H), 4.18 (dd, J=12.5, 5.9 Hz, 1H), 3.67-3.42 (m, 4H), 3.02 (dd, J=16.3, 7.7 Hz, 1H), 2.70 (dd, J=16.5, 5.6 Hz, 1H), 2.25 (s, 6H), 2.09 (brs, 2H), 1.89 (brs, 2H). $^{13}$C NMR (100 MHz, DMSO-$d_6$) δ 170.78, 167.80, 166.78, 164.95, 156.17, 151.90, 149.31, 144.32, 143.86, 139.38, 132.76, 132.58, 131.57, 125.45, 122.80, 119.10, 116.39, 116.23, 115.51, 107.92, 49.07, 41.87, 38.23, 31.01, 20.87.

Embodiment 11 (S)-2-bromo-N-[3-[2-[bis(pentadeuteroethyl)amino]-2-oxoethyl]-7-(3,5-dimethylphenoxy)-4-methyl-2,5-dioxo-2,3,4,5-tetrahydro-1H-benzo[e][1,4]diazepin-8-yl]-3,4,5-trimethoxybenzamide (Compound 11)

Preparation of (S)-2-[5-(3,5-dimethylphenoxy)-N-methyl-2,4-dinitrobenzamido]butanedioic acid dimethyl ester (Intermediate 56): Intermediate 44 (5.0 mmol) was dissolved in 10 mL of DMF, potassium carbonate (12.5 mmol) and methyl iodide (25.0 mmol) were added and the reaction mixture was reacted at 30° C. for 24 h. The reaction mixture was filtered, concentrated under vacuum to remove DMF, eluted with petroleum ether/ethyl acetate through silica gel column chromatography to obtain 1.99 g of light yellow solid, 81.3% yield. $^{1}$H NMR (400 MHz, DMSO-$d_6$) δ 8.94 (s, 1H), 7.01 (s, 1H), 6.93 (s, 2H), 6.83 (s, 1H), 5.03 (t, J=7.1 Hz, 1H), 3.58 (s, 3H), 3.53 (s, 3H), 3.05 (dd, J=16.5, 6.6 Hz, 1H), 2.95 (dd, J=16.7, 7.5 Hz, 1H), 2.78 (s, 3H), 2.30 (s, 6H). $^{13}$C NMR (100 MHz, DMSO-$d_6$) δ 170.50, 169.27, 165.08, 154.90, 153.45, 140.41, 139.09, 137.93, 137.16, 127.78, 123.86, 117.50, 116.86, 55.02, 52.23, 51.50, 35.36, 32.60, 20.72.

Preparation of(S)-2-[8-amino-7-(3,5-dimethylphenoxy)-4-methyl-2,5-dioxo-2,3,4,5-tetrahydro-1H-benzo[e][1,4]diazepin-3-yl]acetic acid methyl ester (Intermediate 57): according to the synthesis method of the intermediate 45 in Embodiment 1, intermediate 56 were used to prepare it. $^{1}$H NMR (400 MHz, DMSO-$d_6$) δ 10.32 (s, 1H), 7.02 (s, 1H), 6.74 (s, 1H), 6.60 (s, 2H), 6.44 (s, 1H), 5.75 (brs, 2H), 4.41-4.32 (m, 1H), 3.60 (s, 3H), 3.10 (dd, J=19.2, 6.0 Hz, 1H), 2.97 (dd, J=15.8, 0.8 Hz, 1H), 2.84 (s, 3H), 2.24 (s, 6H). $^{13}$C NMR (100 MHz, DMSO-$d_6$) δ 170.69, 169.09, 167.12, 156.94, 144.22, 139.31, 139.12, 134.07, 124.60, 120.67, 115.25, 114.06, 105.04, 52.03, 51.74, 30.92, 29.02, 20.94.

Preparation of (S)-2-[8-amino-7-(3,5-dimethylphenoxy)-4-methyl-2,5-dioxo-2,3,4,5-tetrahydro-1H-benzo[e][1,4]diazepin-3-yl]-N,N-bis(pentadeuteroethyl)acetamide (Intermediate 58): according to the synthesis method of the intermediate 46 in Embodiment 1, intermediate 57 (2.0 mmol) and deuterated diethylamine (4.0 mmol) were used to prepare it. $^{1}$H NMR (400 MHz, DMSO-$d_6$) δ 10.15 (s, 1H), 7.01 (s, 1H), 6.74 (s, 1H), 6.60 (s, 2H), 6.42 (s, 1H), 5.71 (s, 2H), 4.44 (dd, J=9.9, 4.1 Hz, 1H), 3.40 (d, J=6.7 Hz, 1H), 2.87 (s, 3H), 2.81 (dd, J=16.3, 3.7 Hz, 1H), 2.24 (s, 6H).

According to the synthesis method of the compound 1 in Embodiment 1, intermediate 58 (0.2 mmol) and intermediate 52 (0.5 mmol) were used to prepare the title compound (11). $^{1}$H NMR (400 MHz, DMSO-$d_6$) δ 10.44 (s, 1H), 10.22 (s, 1H), 8.02 (s, 1H), 7.16 (s, 1H), 6.82 (s, 1H), 6.81 (s, 1H), 6.68 (s, 2H), 4.46 (dd, J=9.3, 2.3 Hz, 1H), 3.79 (s, 3H), 3.79 (s, 3H), 3.77 (s, 3H), 3.17 (dd, J=15.1, 10.6 Hz, 1H), 2.92 (s, 3H), 2.85 (dd, J=17.1, 1.9 Hz, 1H), 2.25 (s, 6H). $^{13}$C NMR (100 MHz, DMSO-$d_6$) δ 169.43, 167.66, 166.44, 165.90, 156.14, 152.53, 150.28, 144.16, 143.59, 139.33, 133.97, 132.63, 132.55, 125.37, 123.50, 119.30, 116.35, 115.11, 108.30, 105.66, 60.86, 60.74, 56.22, 52.40, 29.69, 29.49, 20.85.

Embodiment 12 (S)-2-chloro-N-[3-[2-[bis(pentadeuteroethyl)amino]-2-oxoethyl]-7-(3,5-dimethylphenoxy)-4-methyl-2,5-dioxo-2,3,4,5-tetrahydro-1H-benzo[e][1,4]diazepin-8-yl]-3,4,5-trimethoxybenzamide (Compound 12)

According to the synthesis method of the compound 1 in Embodiment 1, intermediate 58 (0.2 mmol) and intermediate 53 (0.5 mmol) were used to prepare the title compound (12). $^{1}$H NMR (400 MHz, DMSO-$d_6$) δ 10.44 (s, 1H), 10.22 (s, 1H), 8.01 (s, 1H), 7.16 (s, 1H), 6.84 (s, 1H), 6.81 (s, 1H), 6.68 (s, 2H), 4.46 (dd, J=9.6, 3.2 Hz, 1H), 3.81 (s, 3H), 3.80 (s, 3H), 3.77 (s, 3H), 3.17 (dd, J=15.6, 10.2 Hz, 1H), 2.92 (s, 3H), 2.85 (dd, J=16.2, 3.0 Hz, 1H), 2.25 (s, 6H). $^{13}$C NMR (100 MHz, DMSO-$d_6$) δ 169.48, 167.69, 166.48, 164.97, 156.16, 151.94, 149.37, 144.20, 143.92, 139.39, 132.68, 132.54, 131.65, 125.43, 123.57, 119.39, 116.33, 116.30, 115.17, 107.99, 61.03, 60.81, 56.23, 52.44, 29.72, 29.53, 20.89.

Embodiment 13 (S)-2-bromo-N-[3-[2-[bis(pentadeuteroethyl)amino]-2-oxoethyl]-7-(3,5-dimethylphenoxy)-4-methyl-2,5-dioxo-2,3,4,5-tetrahydro-1H-benzo[e][1,4]diazepin-8-yl]-3,4,5-tris(trideuteromethoxy)benzamide (Compound 13)

According to the synthesis method of the compound 1 in Embodiment 1, intermediate 58 (0.2 mmol) and intermediate 50 (0.5 mmol) were used to prepare the title compound (13). $^{1}$H NMR (400 MHz, DMSO-$d_6$) δ 10.45 (s, 1H), 10.21 (s, 1H), 8.04 (s, 1H), 7.17 (s, 1H), 6.82 (s, 2H), 6.69 (s, 2H), 4.48 (brs, 1H), 3.17 (dd, J=14.3, 10.2 Hz, 1H), 2.92 (s, 3H), 2.86 (d, J=15.6 Hz, 1H), 2.25 (s, 6H). $^{13}$C NMR (100 MHz, DMSO-$d_6$) δ 169.90, 168.13, 166.90, 166.38, 156.62, 152.99, 150.72, 144.63, 144.02, 139.79, 134.40, 133.10, 133.02, 125.84, 123.97, 119.77, 116.84, 115.56, 108.72, 106.09, 52.87, 30.15, 29.96, 21.32.

Embodiment 14 (S)-2-bromo-N-[3-[2-[bis(trideuteromethyl)amino]-2-oxoethyl]-7-(3,5-dimethylphenoxy)-4-methyl-2,5-dioxo-2,3,4,5-tetrahydro-1H-benzo[e][1,4]diazepin-8-yl]-3,4,5-tris(trideuteromethoxy)benzamide (Compound 14)

Preparation of (S)-2-[8-amino-7-(3,5-dimethylphenoxy)-4-methyl-2,5-dioxo-2,3,4,5-tetrahydro-1H-benzo[e][1,4]diazepin-3-yl]-N,N-bis(trideuteromethyl)acetamide (Intermediate 59): according to the synthesis method of the intermediate 46 in Embodiment 1, intermediate 57 (2.0 mmol) and deuterated dimethylamine (4.0 mmol) were used to prepare it.

According to the synthesis method of the compound 1 in Embodiment 1, intermediate 59 (0.2 mmol) and intermediate 50 (0.5 mmol) were used to prepare the title compound (14). $^{1}$H NMR (400 MHz, DMSO-$d_6$) δ 10.46 (s, 1H), 10.21 (s, 1H), 8.04 (s, 1H), 7.17 (s, 1H), 6.82 (s, 1H), 6.81 (s, 1H), 6.68 (s, 2H), 4.43 (dd, J=10.0, 3.7 Hz, 1H), 3.18 (dd, J=16.0, 10.2 Hz, 1H), 2.93 (s, 3H), 2.86 (dd, J=16.0, 3.2 Hz, 1H), 2.25 (s, 6H). $^{13}$C NMR (100 MHz, DMSO-$d_6$) δ 169.85, 169.15, 166.91, 166.38, 156.64, 152.99, 150.72, 144.61, 144.03, 139.79, 134.38, 133.10, 125.82, 123.95, 119.84, 116.80, 115.57, 108.74, 106.09, 52.91, 30.36, 29.97, 21.32.

Embodiment 15 (S)-2-bromo-N-[3-[2-[bis(trideuteromethyl)amino]-2-oxoethyl]-7-(3,5-dimethylphenoxy)-4-methyl-2,5-dioxo-2,3,4,5-tetrahydro-1H-benzo[e][1,4]diazepin-8-yl]-3,4,5-trimethoxybenzamide (Compound 15)

According to the synthesis method of the compound 1 in Embodiment 1, intermediate 59 (0.2 mmol) and intermediate 52 (0.5 mmol) were used to prepare the title compound (15). $^{1}$H NMR (400 MHz, DMSO-$d_6$) δ 10.46 (s, 1H), 10.21 (s, 1H), 8.04 (s, 1H), 7.17 (s, 1H), 6.83 (s, 1H), 6.81 (s, 1H), 6.68 (s, 2H), 4.43 (dd, J=10.0, 3.7 Hz, 1H), 3.80 (s, 3H), 3.79 (s, 3H), 3.77 (s, 3H), 3.18 (dd, J=16.0, 10.2 Hz, 1H), 2.93 (s, 3H), 2.86 (dd, J=15.9, 3.2 Hz, 1H), 2.25 (s, 6H). $^{13}$C NMR (100 MHz, DMSO-$d_6$) δ 169.85, 169.15, 166.91, 166.37, 156.64, 153.00, 150.75, 144.60, 144.07, 139.79, 134.43, 133.11, 125.82, 123.95, 119.84, 116.80, 115.57, 108.79, 106.13, 61.33, 61.21, 56.70, 52.91, 30.35, 29.97, 21.32.

Embodiment 16 (S)-2-bromo-N-[3-[2-(dimethylamino)-2-oxoethyl]-7-(3,5-dimethylphenoxy)-4-methyl-2,5-dioxo-2,3,4,5-tetrahydro-1H-benzo[e][1,4]diazepin-8-yl]-3,4,5-tris(trideuteromethoxy)benzamide (Compound 16)

Preparation of (S)-2-[8-amino-7-(3,5-dimethylphenoxy)-4-methyl-2,5-dioxo-2,3,4,5-tetrahydro-1H-benzo[e][1,4]diazepin-3-yl]-N,N-dimethylacetamide (Intermediate 60): according to the synthesis method of the intermediate 46 in Embodiment 1, 57 (2.0 mmol) and dimethylamine (4.0 mmol) were used to prepare it.

According to the synthesis method of the compound 1 in Embodiment 1, intermediate 60 (0.2 mmol) and intermediate 50 (0.5 mmol) were used to prepare the title compound (16). $^{1}$H NMR (400 MHz, DMSO-$d_6$) δ 10.46 (s, 1H), 10.21 (s, 1H), 8.04 (s, 1H), 7.17 (s, 1H), 6.83 (s, 1H), 6.81 (s, 1H), 6.68 (s, 2H), 4.43 (d, J=6.7 Hz, 1H), 3.19 (dd, J=14.6, 10.9 Hz, 1H), 3.06 (s, 3H), 2.93 (s, 3H), 2.87 (d, J=16.4 Hz, 1H), 2.79 (s, 3H), 2.25 (s, 6H). $^{13}$C NMR (100 MHz, DMSO-$d_6$) δ 169.84, 169.13, 166.90, 166.38, 156.64, 152.98, 150.71, 144.60, 144.02, 139.78, 134.38, 133.10, 125.82, 123.94, 119.83, 116.80, 115.56, 108.73, 106.09, 52.91, 36.95, 35.17, 30.37, 29.97, 21.32.

Embodiment 17 (S)-2-chloro-N-[3-[2-(4,4-difluoropiperidin-1-yl)-2-oxoethyl]-7-(3,5-dimethylphenoxy)-4-methyl-2,5-dioxo-2,3,4,5-tetrahydro-1H-benzo[e][1,4]diazepin-8-yl]-3,4,5-tris(trideuteromethoxy)benzamide (Compound 17)

Preparation of (S)-8-amino-3-[2-(4,4-difluoropiperidin-1-yl)-2-oxoethyl]-7-(3,5-methylphenoxy)-4-methyl-3,4-dihydro-1H-benzo[e][1,4]diazepin-2.5-dione (Intermediate 61): according to the synthesis method of the intermediate 46 in Embodiment 1, 48 (2.0 mmol) and 4.4-difluoropiperidine (4.0 mmol) were used to prepare it.

According to the synthesis method of the compound 1 in Embodiment 1, intermediate 61 (0.2 mmol) and intermediate 47 (0.5 mmol) were used to prepare the title compound (17). $^{1}$H NMR (400 MHz, DMSO-$d_6$) δ 10.48 (s, 1H), 10.22 (s, 1H), 8.02 (s, 1H), 7.17 (s, 1H), 6.84 (s, 1H), 6.81 (s, 1H), 6.68 (s, 2H), 4.44 (dd, J=9.7, 3.1 Hz, 1H), 3.79-3.38 (m, 4H), 3.31-3.25 (m, 1H), 2.97 (s, 1H), 2.94 (s, 3H), 2.25 (s, 6H), 2.06 (brs, 2H), 1.87 (brs, 2H). $^{13}$C NMR (100 MHz, DMSO-$d_6$) δ 169.42, 167.81, 166.44, 164.98, 156.16, 151.91, 149.32, 144.19, 143.85, 139.36, 132.63, 132.58, 131.59, 125.41, 123.49, 119.38, 116.31, 116.22, 115.13, 107.91, 52.48, 41.68, 38.24, 29.63, 20.87.

Embodiment 18 (S)-2-bromo-N-[3-[2-(diethylamino)-2-oxoethyl]-7-(3,5-dimethylphenoxy)-4-trideuteromethyl-2,5-dioxo-2,3,4,5-tetrahydro-1H-benzo[e][1,4]diazepin-8-yl]-3,4,5-trimethoxybenzamide (Compound 18)

Preparation of (S)-2-[5-(3,5-dimethylphenoxy)-N-trideuteromethyl-2,4-dinitrobenzamido]dimethyl succinate (Intermediate 60): according to the synthesis method of the intermediate 56 in Embodiment 11, intermediate 44 (5.0 mmol) and deuterated iodomethane (025.0 mmol) were used to prepare it.

Preparation of (S)-2-[8-amino-7-(3,5-dimethylphenoxy)-4-trideuteromethyl-2,5-dioxo-2,3,4,5-tetrahydro-1H-benzo[e][1,4]diazepin-3-yl]acetic acid methyl ester (Intermediate 63): according to the synthesis method of the intermediate 45 in Embodiment 1, intermediate 62 was used to prepare it.

$^{1}$H NMR (400 MHz, DMSO-$d_6$) δ 10.33 (s, 1H), 7.01 (s, 1H), 6.74 (s, 1H), 6.60 (s, 2H), 6.43 (s, 1H), 5.76 (brs, 2H), 4.36 (dd, J=9.4, 5.1 Hz, 1H), 3.59 (s, 3H), 3.09 (dd, J=16.1, 9.6 Hz, 1H), 2.97 (dd, J=15.7, 3.1 Hz, 1H), 2.24 (s, 6H). $^{13}$C NMR (100 MHz, DMSO-$d_6$) δ 170.70, 169.13, 167.22, 156.97, 144.24, 139.33, 139.15, 134.07, 124.63, 120.70, 115.26, 114.10, 105.08, 52.00, 51.76, 30.91, 20.95.

Preparation of (S)-2-[8-amino-7-(3,5-dimethylphenoxy)-4-methyl-2,5-dioxo-2,3,4,5-tetrahydro-1H-benzo[e][1,4]diazepin-3-yl]-N,N-diethylacetamide (Intermediate 64): according to the synthesis method of the intermediate 46 in Embodiment 1, intermediate 63 (2.0 mmol) and diethylamine (4.0 mmol) were used to prepare it.

According to the synthesis method of the compound 1 in Embodiment 1, intermediate 64 (0.2 mmol) and intermediate 52 (0.5 mmol) were used to prepare the title compound (18). $^{1}$H NMR (400 MHz, DMSO-$d_6$) δ 10.44 (s, 1H), 10.21 (s, 1H), 8.03 (s, 1H), 7.16 (s, 1H), 6.82 (s, 1H), 6.81 (s, 1H), 6.68 (s, 2H), 4.46 (dd, J=9.6, 3.6 Hz, 1H), 3.80 (s, 3H), 3.79 (s, 3H), 3.77 (s, 3H), 3.49-3.36 (m, 2H), 3.28-3.15 (m, 3H), 2.85 (d, J=15.8 Hz, 1H), 2.25 (s, 6H), 1.17 (t, J=6.4 Hz, 3H), 0.97 (t, J=6.8 Hz, 3H). $^{13}$C NMR (100 MHz, DMSO-$d_6$) δ 169.44, 167.67, 166.45, 165.89, 156.13, 152.52, 150.27, 144.16, 143.58, 139.31, 133.96, 132.62, 132.54, 125.36, 123.50, 119.30, 116.35, 115.12, 108.29, 105.65, 60.85, 60.73, 56.22, 52.36, 41.17, 29.70, 20.84, 13.94, 12.96.

Embodiment 19 (S)-2-chloro-N-[3-[2-[bis(pentadeuteroethyl)amino]-2-oxoethyl]-7-(3,5-dimethylphenoxy)-4-(trideuteromethyl)-2,5-dioxo-2,3,4,5-tetrahydro-1H-benzo[e][1,4]diazepin-8-yl]-3,4,5-trimethoxybenzamide (Compound 19)

Preparation of (S)-2-[8-amino-7-(3,5-dimethylphenoxy)-4-(trideuteromethyl)-2,5-dioxo-2,3,4,5-tetrahydro-1H-benzo[e][1,4]diazepin-3-yl]-N,N-bis(pentadeuteroethyl)acetamide (Intermediate 65): according to the synthesis method of the intermediate 46 in Embodiment 1, intermediate 63 (2.0 mmol) and deuterated diethylamine (4.0 mmol) were used to prepare it.

According to the synthesis method of the compound 1 in Embodiment 1, intermediate 65 (0.2 mmol) and intermediate 53 (0.5 mmol) were used to prepare the title compound (19). $^{1}$H NMR (400 MHz, DMSO-$d_6$) δ 10.44 (s, 1H), 10.22 (s, 1H), 8.01 (s, 1H), 7.16 (s, 1H), 6.84 (s, 1H), 6.81 (s, 1H), 6.68 (s, 2H), 4.51-4.41 (m, 1H), 3.81 (s, 3H), 3.80 (s, 3H), 3.77 (s, 3H), 3.16 (dd, J=15.1, 10.2 Hz, 1H), 2.85 (dd, J=15.0, 1.4 Hz, 1H), 2.25 (s, 6H). $^{13}$C NMR (100 MHz, DMSO-$d_6$) δ 169.48, 167.68, 166.47, 164.96, 156.15, 151.92, 149.36, 144.17, 143.89, 139.37, 132.68, 132.55, 131.67, 125.41, 123.54, 119.36, 116.33, 116.29, 115.13, 107.97, 61.02, 60.79, 56.21, 52.39, 29.70, 20.87.

Embodiment 20 (S)-2-bromo-N-[3-[2-(dimethylamino)-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy)benzamide (Compound 20)

Preparation of (S)-2-[8-amino-7-(3,5-dimethylphenoxy)-2,5-dioxo-2,3,4,5-tetrahydro-1H-benzo[e][1,4]diazepin-3-yl]-N,N-dimethylacetamide (Intermediate 66): according to the synthesis method of the intermediate 46 in Embodiment 1, intermediate 45 (2.0 mmol) and dimethylamine (4.0 mmol) were used to prepare it.

According to the synthesis method of the compound 1 in Embodiment 1, intermediate 66 (0.2 mmol) and intermediate 50 (0.5 mmol) were used to prepare the title compound (20). $^{1}$H NMR (400 MHz, DMSO-$d_6$) δ 10.40 (s, 1H), 10.21 (s, 1H), 8.51 (d, J=5.2 Hz, 1H), 8.02 (s, 1H), 7.16 (s, 1H), 6.82 (s, 1H), 6.81 (s, 1H), 6.68 (s, 2H), 4.15 (dt, J=8.0, 5.3 Hz, 1H), 3.00 (s, 3H), 2.95 (dd, J=16.8, 8.6 Hz, 1H), 2.81 (s, 3H), 2.62 (dd, J=16.4, 5.0 Hz, 1H), 2.25 (s, 6H). $^{13}$C NMR (100 MHz, DMSO-$d_6$) δ 170.71, 168.84, 166.74, 165.87, 156.17, 152.49, 150.23, 144.28, 143.54, 139.32, 133.87, 132.74, 132.59, 125.38, 122.84, 119.07, 116.39, 115.50, 108.25, 105.61, 48.99, 36.49, 34.73, 31.36, 20.84.

Embodiment 21 (S)-2-bromo-N-[3-[2-[bis(trideuteromethyl)amino]-2-oxoethyl]-7-(3,5-dimethylphenoxy)-2,5-dioxo-2,3,4,5-tetrahydro-1H-benzo[e][1,4]diazepin-8-yl]-3,4,5-tris(trideuteromethoxy)benzamide (Compound 21)

Preparation of (S)-2-[8-amino-7-(3,5-dimethylphenoxy)-2,5-dioxo-2,3,4,5-tetrahydro-1H-benzo[e][1,4]diazepin-3-yl]-N,N-bis(trideuteromethyl)acetamide (Intermediate 67): according to the synthesis method of the intermediate 46 in Embodiment 1, intermediate 45 (2.0 mmol) and deuterated dimethylamine (4.0 mmol) were used to prepare it.

According to the synthesis method of the compound 1 in Embodiment 1, intermediate 67 (0.2 mmol) and intermediate 50 (0.5 mmol) were used to prepare the title compound (21). $^{1}$H NMR (400 MHz, DMSO-$d_6$) δ 10.41 (s, 1H), 10.20 (s, 1H), 8.51 (d, J=5.3 Hz, 1H), 8.03 (s, 1H), 7.17 (s, 1H), 6.83 (s, 1H), 6.81 (s, 1H), 6.68 (s, 2H), 4.16 (dt, J=8.2, 5.4 Hz, 1H), 2.94 (dd, J=16.5, 8.3 Hz, 1H), 2.61 (dd, J=16.5, 5.2 Hz, 1H), 2.25 (s, 6H). $^{13}$C NMR (100 MHz, DMSO-$d_6$) δ 171.21, 169.35, 167.24, 166.35, 156.66, 152.99, 150.72, 144.76, 144.05, 139.81, 134.35, 133.25, 133.09, 125.86, 123.32, 119.58, 116.86, 115.98, 108.75, 106.11, 49.49, 31.83, 21.33.

Embodiment 22 (S)-2-bromo-N-[3-[2-[bis(trideuteromethyl)amino]-2-oxoethyl]-7-(3,5-dimethylphenoxy)-2,5-dioxo-2,3,4,5-tetrahydro-1H-benzo[e][1,4]diazepin-8-yl]-3,4,5-trimethoxybenzamide (Compound 22)

According to the synthesis method of the compound 1 in Embodiment 1, intermediate 67 (0.2 mmol) and intermediate 52 (0.5 mmol) were used to prepare the title compound (22). $^{1}$H NMR (400 MHz, DMSO-$d_6$) δ 10.40 (s, 1H), 10.21 (s, 1H), 8.51 (d, J=5.3 Hz, 1H), 8.02 (s, 1H), 7.16 (s, 1H), 6.83 (s, 1H), 6.81 (s, 1H), 6.68 (s, 2H), 4.15 (dt, J=8.3, 5.4 Hz, 1H), 3.80 (s, 3H), 3.79 (s, 3H), 3.77 (s, 3H), 2.94 (dd, J=16.5, 8.3 Hz, 1H), 2.61 (dd, J=16.5, 5.2 Hz, 1H), 2.25 (s, 6H). $^{13}$C NMR (100 MHz, DMSO-$d_6$) δ 171.21, 169.35, 167.24, 166.34, 156.66, 152.99, 150.75, 144.77, 144.08, 139.81, 134.40, 133.23, 133.08, 125.86, 123.33, 119.57, 116.87, 116.00, 108.80, 106.14, 61.33, 61.21, 56.70, 49.48, 31.82, 21.33.

Embodiment 23 (S)-2-chloro-N-[3-[2-(diethylamino)-2-oxoethyl]-7-[3,5-bis(trideuteromethyl)phenoxy]-2,5-dioxo-2,3,4,5-tetrahydro-1H-benzo[e][1,4]diazepin-8-yl]-3,4,5-trimethoxybenzamide (Compound 23)

Preparation of 3,5-bis(trideuteromethyl)phenol (Intermediate 68): 3,5-dimethylphenol (32.79 mmol) and potassium carbonate (65.57 mmol) were dissolved in 30 mL of acetone, and dimethyl sulfate (65.58 mmol) was added and the reaction mixture was reacted at 60° C. for 2 h. The reaction solution was concentrated under vacuum, dissolved with DCM, washed with water, separated to obtain the organic phase, dried, concentrated, and eluted with petroleum ether/ethyl acetate through silica gel column chromatography to obtain 3.07 g of intermediate product, 84.1% yield. The above intermediate (14.71 mmol) and potassium tert-butoxide (63.24 mmol) were mixed in 12 mL of DMSO-$d_6$, and the reaction mixture was reacted at 100° C. for 3 h. The reaction mixture was poured into 20 mL of heavy water, extracted with ether and concentrated to obtain yellow oil. The above oil and potassium tert-butoxide (28.79 mmol) were mixed in 8 mL of DMSO-$d_6$, and the reaction mixture was reacted at 100° C. for 2 h. The reaction mixture was poured into 20 mL of heavy water, extracted with ether, dried, concentrated, and eluted with petroleum ether through silica gel column chromatography to obtain 1.57 g of intermediate product, with a yield of 75.5% and a deuteration rate of 97.2%, in which some hydrogens exchanged on the benzene ring. The above intermediate (10.56 mmol) was dissolved in 30 mL of DCM and a solution of boron tribromide in 10 mL of DCM (21.13 mmol) was added dropwise at 0° C. and the reaction mixture was reacted at room temperature for 2 h. The reaction mixture was quenched with 8 mL of heavy water, and separated to obtain the organic phase, dried, concentrated, and eluted with petroleum ether/ethyl acetate through silica gel column chromatography to obtain 1.0 g of intermediate, 71.9% yield. The above intermediate (7.0 mmol) and sodium hydroxide (7.0 mmol) were dissolved in 20 mL of water and the reaction mixture was reacted at 100° C. overnight. Its PH was adjusted to acidity with 1 M hydrochloric acid, and the resulting mixture was extracted with DCM and dried to obtain 698 mg of the target compound, 77.6% yield. The deuteration rate of the target compound is about 98%. Confirmed by $^1$H NMR, the hydrogen on the benzene ring was not replaced by $^1$H NMR.

Preparation of (S)-2-[8-amino-7-[3,5-bis(trideuteromethyl)phenoxy]-2,5-dioxo-2,3,4,5-tetrahydro-1H-benzo[e][1,4]diazepin-3-yl]acetic acid methyl ester (Intermediate 69): according to the synthesis method of the intermediate 45 in Embodiment 1, intermediate 68 was used to prepare it. $^1$H NMR (400 MHz, DMSO-$d_6$) δ 10.24 (s, 1H), 8.17 (d, J=4.9 Hz, 1H), 7.00 (s, 1H), 6.75 (s, 1H), 6.60 (s, 2H), 6.42 (s, 1H), 5.77 (s, 2H), 4.10-4.00 (m, 1H), 3.58 (s, 3H), 2.85 (dd, J=16.9, 8.9 Hz, 1H), 2.69 (dd, J=17.0, 5.5 Hz, 1H). $^{13}$C NMR (100 MHz, DMSO-$d_6$) δ 170.69, 170.41, 167.42, 156.98, 144.37, 139.40, 139.05, 134.05, 124.66, 120.36, 115.36, 113.42, 105.46, 51.54, 48.73, 32.59.

According to the synthesis method of the compound 1 in Embodiment 1, intermediate 69 (0.2 mmol), 2-chloro-3,4,5-trimethoxybenzoic acid (0.5 mmol) and diethylamine (0.4 mmol) were used to prepare the title compound (23) by three steps. $^1$H NMR (400 MHz, DMSO-$d_6$) δ 10.38 (s, 1H), 10.23 (s, 1H), 8.52 (d, J=5.2 Hz, 1H), 8.00 (s, 1H), 7.16 (s, 1H), 6.84 (s, 1H), 6.81 (s, 1H), 6.68 (s, 2H), 4.18 (dt, J=8.9, 5.1 Hz, 1H), 3.81 (s, 3H), 3.80 (s, 3H), 3.77 (s, 3H), 3.32-3.17 (m, 4H), 2.98 (dd, J=16.3, 8.5 Hz, 1H), 2.60 (dd, J=16.4, 4.8 Hz, 1H), 1.17 (t, J=6.9 Hz, 3H), 0.99 (t, J=7.0 Hz, 3H). $^{13}$C NMR (100 MHz, DMSO-$d_6$) δ 170.79, 167.92, 166.80, 164.92, 156.20, 151.92, 149.36, 144.29, 143.91, 139.27, 132.72, 132.66, 131.63, 125.43, 122.94, 119.16, 116.37, 116.30, 115.54, 107.98, 61.02, 60.79, 56.22, 49.01, 41.36, 31.25, 13.91, 13.05.

Embodiment 24 (S)-2-chloro-N-[3-[2-(diethylamino)-2-oxoethyl]-7-(3,5-dimethyl-2,4,6-trideuterophenoxy)-2,5-dioxo-2,3,4,5-tetrahydro-1H-benzo[e][1,4]diazepin-8-yl]-3,4,5-trimethoxybenzamide (Compound 24)

Preparation of 3,5-dimethyl-2,4,6-trideuterophenol (Intermediate 70): 3,5-dimethylphenol (10.0 mmol) was dissolved in 100 mmol of heavy water, and 200 μL of sodium deuteroxide (40.0% in $D_2O$) was added and the reaction mixture was reacted at 100° C. for 22 h. A solution of 600 μL of concentrated sulfuric acid in 1.4 mL of heavy water was added, the resulting mixture was extracted with DCM and evaporated, and the above process was repeated 5 times to obtain crude product. The crude product was eluted with petroleum ether/ethyl acetate through silica gel column chromatography to obtain 1.2 g of the target compound, with a yield of 82.8% and a deuteration rate of 97.0%. $^1$H NMR (400 MHz, DMSO-$d_6$) δ 9.07 (s, 1H), 2.15 (s, 6H).

Preparation of (S)-2-[8-amino-7-(3,5-dimethyl-2,4,6-trideuterophenoxy)-2,5-dioxo-2,3,4,5-tetrahydro-1H-benzo[e][1,4]diazepin-3-yl]methyl acetate (Intermediate 71): according to the synthesis method of the intermediate 45 in Embodiment 1, intermediate 70 (2.12 mmol) was used to prepare it. $^1$H NMR (400 MHz, DMSO-$d_6$) δ 10.23 (s, 1H), 8.16 (d, J=4.6 Hz, 1H), 7.01 (s, 1H), 6.43 (s, 1H), 5.75 (s, 2H), 4.05 (dt, J=10.1, 5.1 Hz, 1H), 3.59 (s, 3H), 2.86 (dd, J=16.9, 8.8 Hz, 1H), 2.69 (dd, J=16.9, 5.5 Hz, 1H), 2.24 (s, 6H). $^{13}$C NMR (100 MHz, DMSO-$d_6$) δ 170.68, 170.40, 167.40, 156.87, 144.35, 139.40, 138.95, 134.04, 120.34, 113.41, 105.45, 51.52, 48.72, 32.58, 20.82.

According to the synthesis method of the compound 1 in Embodiment 1, intermediate 71 (0.2 mmol), 2-chloro-3,4,5-trimethoxybenzoic acid (0.5 mmol) and diethylamine (0.4 mmol) were used to prepare the title compound (24) by three steps. $^1$H NMR (400 MHz, DMSO-$d_6$) δ 10.38 (s, 1H), 10.23 (s, 1H), 8.52 (d, J=5.4 Hz, 1H), 8.00 (s, 1H), 7.16 (s, 1H), 6.84 (s, 1H), 4.18 (dt, J=8.9, 5.3 Hz, 1H), 3.81 (s, 3H), 3.80 (s, 3H), 3.77 (s, 3H), 3.30-3.19 (m, 4H), 2.98 (dd, J=16.3, 8.5 Hz, 1H), 2.60 (dd, J=16.2, 4.9 Hz, 1H), 2.25 (s, 6H), 1.17 (t, J=7.0 Hz, 3H), 0.99 (t, J=7.0 Hz, 3H). $^{13}$C NMR (100 MHz, DMSO-$d_6$) δ 170.77, 167.89, 166.77, 164.90, 156.09, 151.90, 149.34, 144.27, 143.88, 139.16, 132.70, 132.64, 131.62, 122.93, 119.12, 116.28, 115.51, 107.96, 61.00, 60.77, 56.20, 48.99, 41.35, 31.23, 20.74, 13.90, 13.04.

Embodiment 25 (S)-2-chloro-N-[3-[2-(diethylamino)-2-oxoethyl]-7-[3,5-bis(trideuteromethyl)-2,4,6-trideuterophenoxy]-2,5-dioxo-2,3,4,5-tetrahydro-1H-benzo[e][1,4]diazepin-8-yl]-3,4,5-trimethoxybenzamide (Compound 25)

Preparation of 3,5-bis(trideuteromethyl))-2,4,6-trideuterophenol (Intermediate 72): 3,5-dimethylphenol (32.79 mmol) and potassium carbonate (65.57 mmol) were dissolved in 30 mL of acetone, and dimethyl sulfate (65.58 mmol) was added and the reaction mixture was reacted at 60° C. for 2 h. The reaction solution was evaporated, dissolved with DCM, washed with water, and separated to obtain the organic phase, dried, concentrated, and eluted with petroleum ether/ethyl acetate through silica gel column chromatography to obtain 3.07 g of intermediate product, 84.1% yield. The above intermediate (14.71 mmol) and potassium tert-butoxide (63.24 mmol) were mixed in 12 mL of DMSO-$d_6$ and the reaction mixture was reacted at 100° C. for 3 h. The reaction mixture was poured into 20 mL of heavy water, extracted with ether and concentrated to obtain yellow oil. The above oil and potassium tert-butoxide (28.79 mmol) were mixed in 8 mL of DMSO-$d_6$ and the reaction mixture was reacted at 100° C. for 2 h. The reaction mixture was poured into 20 mL of heavy water, extracted with ether, dried, concentrated, and eluted with petroleum ether through silica gel column chromatography to obtain 1.57 g of intermediate product, with a yield of 75.5% and a deuteration rate of 97.2%, in which some hydrogens exchanged on the benzene ring. The above intermediate (10.56 mmol) was dissolved in 30 mL of DCM, and a solution of boron tribromide in 10 mL of DCM (21.13 mmol) was added dropwise at 0° C. and the reaction mixture was reacted at room temperature for 2 h. The reaction mixture was quenched with 8 mL of heavy water, and separated to obtain the organic phase, dried, concentrated and eluted with petroleum ether/ethyl acetate through silica gel column chromatography to obtain 1.0 g of intermediate, 71.9% yield. The above intermediate (7.3 mmol) was dissolved in 73.05 mmol of heavy water, and 161 μL of sodium deuteroxide (40% in $D_2O$) was added and the reaction mixture was reacted at 100° C. for 22 h. A solution of 426 μL of concentrated sulfuric acid in 1.1 mL of heavy water was added, the resulting mixture was extracted with DCM and evaporated, and the above process was repeated 7 times to obtain crude product. The crude product was eluted with petroleum ether/ethyl acetate through silica gel column chromatography to obtain 640 mg of the target compound, with a yield of 67.0% and a deuteration rate of 97.3%. $^1H$ NMR (400 MHz, DMSO-$d_6$) δ 9.07 (s, 1H).

Preparation of (S)-2-[8-amino-7-[3,5-bis(trideuteromethyl)-2,4,6-trideuterophenoxy]-2,5-dioxo-2,3,4,5-tetrahydro-1H-benzo[e][1,4]diazepin-3-yl]methyl acetate (Intermediate 73): according to the synthesis method of the intermediate 45 in Embodiment 1, intermediate 72 (2.12 mmol) was used to prepare it. $^1H$ NMR (400 MHz, DMSO-$d_6$) δ 10.23 (s, 1H), 8.16 (d, J=4.6 Hz, 1H), 7.01 (s, 1H), 6.43 (s, 1H), 5.75 (s, 2H), 4.11-3.98 (m, 1H), 3.59 (s, 3H), 2.86 (dd, J=16.9, 8.9 Hz, 1H), 2.69 (dd, J=16.9, 5.3 Hz, 1H). $^{13}C$ NMR (100 MHz, DMSO-$d_6$) δ 170.67, 170.39, 167.40, 156.86, 144.34, 139.41, 138.84, 134.03, 120.32, 113.41, 105.44, 51.52, 48.72, 32.57.

According to the synthesis method of the compound 1 in Embodiment 1, intermediate 73 (0.2 mmol), 2-chloro-3,4,5-trimethoxybenzoic acid (0.5 mmol) and diethylamine (0.4 mmol) were used to prepare the title compound (25) by three steps. $^1H$ NMR (400 MHz, DMSO-$d_6$) δ 10.38 (s, 1H), 10.22 (s, 1H), 8.51 (d, J=5.4 Hz, 1H), 8.00 (s, 1H), 7.16 (s, 1H), 6.84 (s, 1H), 4.18 (dt, J=8.6, 5.2 Hz, 1H), 3.81 (s, 3H), 3.80 (s, 3H), 3.77 (s, 3H), 3.36-3.18 (m, 4H), 2.98 (dd, J=16.3, 8.6 Hz, 1H), 2.60 (dd, J=16.3, 4.9 Hz, 1H), 1.17 (t, J=7.0 Hz, 3H), 0.99 (t, J=7.0 Hz, 3H). $^{13}C$ NMR (100 MHz, DMSO-$d_6$) δ 170.76, 167.89, 166.76, 164.90, 156.08, 151.89, 149.33, 144.29, 143.88, 139.05, 132.68, 132.63, 131.62, 122.92, 119.10, 116.27, 115.51, 107.96, 60.99, 60.77, 56.20, 48.99, 41.34, 31.22, 13.90, 13.04.

Embodiment 26 (S)-dimethyl-(4-8-(2-bromo-3,4,5-tris(trideuteromethoxy)benzoyl)-7-(3,5-dimethylphenoxy)-2,5-dioxo-2,3,4,5-tetrahydro-1H-benzo[e][1,4]diazepin-3-yl)-2-methyl-3-oxobutyl-2-yl)dimethyl phosphate (Compound 26)

The title compound (26) was prepared according to the following route:

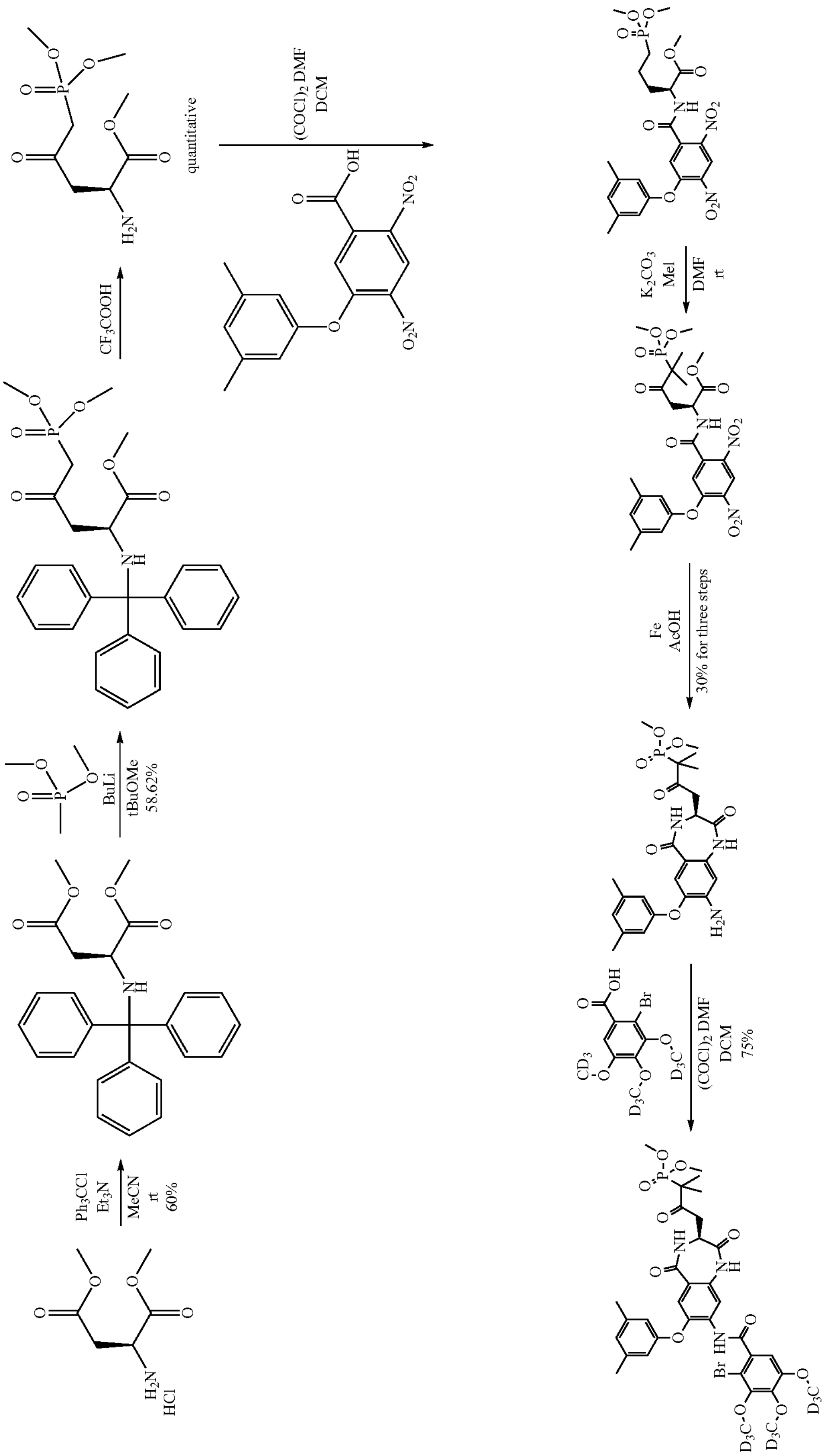
Ph3CCl
Et3N
MeCN
rt
60%
BuLi
tBuOMe
58.62%
CF3COOH
quantitative
(COCl)2 DMF
DCM
K2CO3
MeI
DMF
rt
Fe
AcOH
30% for three steps
(COCl)2 DMF
DCM
75%

The title compound (26) Mp 141-143° C. $^{1}H$ NMR (400 MHz, DMSO-$d_6$) δ 10.45 (s, 1H), 10.24 (s, 1H), 8.52 (d, J=5.0 Hz, 1H), 8.03 (s, 1H), 7.16 (s, 1H), 6.82 (s, 2H), 6.68 (s, 2H), 4.13 (dd, J=11.7, 5.6 Hz, 1H), 3.70 (s, 3H), 3.67 (s, 3H), 3.42 (dd, J=18.5, 8.4 Hz, 1H), 2.97 (dd, J=18.4, 4.3 Hz, 1H), 2.25 (s, 6H), 1.39 (d, J=16.9 Hz, 3H), 1.34 (d, J=16.8 Hz, 3H).

Embodiment 27 (S)-2-bromo-N-[7-(3,5-dimethylphenoxy)-3-[2-(4-methylpiperazin-1-yl)-2-oxoethyl]-2,5-dioxo-2,3,4,5-tetrahydro-1H-benzo[e][1,4]diazepin-8-yl]-3,4,5-tris(trideuteromethyl) benzamide hydrochloride (Compound 27)

Preparation of (S)-2-(8-(2-bromo-3,4,5-tris(trideuteromethoxy)benzamido)-7-(3,5-dimethylphenoxy)-2,5-dioxo-2,3,4,5-tetrahydro-1H-benzo[e][1,4]diazepin-3-yl]acetic acid (Intermediate 74): according to the method in Embodiment 1, intermediate 45 (2.0 mmol), intermediate 50 (5.0 mmol) and lithium hydroxide (5.0 mmol) were used to prepare it by two steps.

According to the method in Embodiment 1, intermediate 74 (1.0 mmol), N-methylpiperazine (2.0 mmol) and concentrated hydrochloric acid were used to prepare the title compound (27) by two steps. $^{1}H$ NMR (400 MHz, DMSO-$d_6$) δ 11.07 (s, 1H), 10.46 (s, 1H), 10.24 (s, 1H), 8.52 (d, J=4.4 Hz, 1H), 8.03 (s, 1H), 7.16 (s, 1H), 6.81 (s, 2H), 6.67 (s, 2H), 4.33-4.43 (m, 1H), 4.15-4.23 (m, 1H), 3.60-3.67 (m, 2H), 3.55-3.32 (m, 5H), 2.97-3.02 (m, 2H), 2.76 (s, 3H), 2.25 (s, 6H).

Embodiment 28 (S)-2-bromo-N-[7-(3,5-dimethylphenoxy)-4-methyl-3-[2-(4-methylpiperazin-1-yl)-2-oxoethyl]-2,5-dioxo-2,3,4,5-tetrahydro-1H-benzo [e][1,4]diazepin-8-yl]-3,4,5-tris(trideuteromethyl) benzamide (Compound 28)

Preparation of (S)-2-(8-(2-bromo-3,4,5-tris(trideuteromethoxy)benzamido)-7-(3,5-dimethylphenoxy)-4-methyl-2,5-dioxo-2,3,4,5-tetrahydro-1H-benzo[e][1,4]diazepin-3-yl]acetic acid (Intermediate 75): according to the method in Embodiment 1, intermediate 57 (2.0 mmol), intermediate 50 (2.0 mmol) and lithium hydroxide (2.0 mmol) were used to prepare it by two steps.

According to the method in Embodiment 1, intermediate 75 (0.2 mmol) and N-methylpiperazine (0.4 mmol) were used to prepare the title compound (28). $^{1}H$ NMR (400 MHz, DMSO-$d_6$) δ 10.46 (s, 1H), 10.21 (s, 1H), 8.03 (s, 1H), 7.16 (s, 1H), 6.82 (s, 2H), 6.68 (s, 2H), 4.44 (dd, J=10.2, 2.8 Hz, 1H), 3.56 (s, 2H), 3.39-3.45 (m, 2H), 3.22 (dd, J=17.1, 10.8 Hz, 1H), 2.93 (s, 3H), 2.87 (s, 1H), 2.41 (s, 1H), 2.27-2.37 (m, 3H), 2.25 (s, 6H), 2.22 (s, 3H).

Embodiment 29 (S)-2-bromo-N-[7-(3,5-dimethylphenoxy)-3-[2-(4-methylpiperazin-1-yl)-2-oxoethyl]-2,5-dioxo-2,3,4,5-tetrahydro-1H-benzo[e][1,4]diazepin-8-yl]-3,4,5-tris(trideuteromethoxy) benzamide (Compound 29)

According to the method in Embodiment 1, intermediate 74 (0.2 mmol) and N-methylpiperazine (0.4 mmol) were used to prepare the title compound (29). $^{1}H$ NMR (400 MHz, DMSO-$d_6$) δ 10.40 (s, 1H), 10.21 (s, 1H), 8.51 (d, J=4.5 Hz, 1H), 8.02 (s, 1H), 7.15 (s, 1H), 6.81 (s, 2H), 6.68 (s, 2H), 4.16 (dd, J=12.6, 6.1 Hz, 1H), 3.36-3.52 (m, 4H), 2.95 (dd, J=16.6, 7.9 Hz, 1H), 2.62 (dd, J=16.4, 5.1 Hz, 1H), 2.28-2.40 (m, 4H), 2.25 (s, 6H), 2.20 (s, 3H).

Embodiment 30 (S)-2-bromo-N-[7-(3,5-dimethylphenoxy)-3-[2-(methoxymethylamino)-2-oxoethyl]-2,5-dioxo-2,3,4,5-tetrahydro-1H-benzo[e][1,4]diazepin-8-yl]-3,4,5-tris(trideuteromethoxy) benzamide (Compound 30)

According to the method in Embodiment 1, intermediate 74 (0.2 mmol) and methoxymethylamine (0.4 mmol) were used to prepare the title compound (30). $^{1}H$ NMR (400 MHz, DMSO-$d_6$) δ 10.43 (s, 1H), 10.21 (s, 1H), 8.57 (d, J=5.0 Hz, 1H), 8.02 (s, 1H), 7.16 (s, 1H), 6.82 (s, 2H), 6.68 (s, 2H), 4.13 (dd, J=12.7, 5.1 Hz, 1H), 3.73 (s, 3H), 3.19-3.12 (m, 1H), 3.08 (s, 3H), 2.70 (dd, J=17.1, 4.6 Hz, 1H), 2.25 (s, 6H).

Embodiment 31 (S)-2-bromo-N-[7-(3,5-dimethylphenoxy)-3-[2-(hydroxymethylamino)-2-oxoethyl]-2,5-dioxo-2,3,4,5-tetrahydro-1H-benzo[e][1,4]diazepin-8-yl]-3,4,5-tris(trideuteromethoxy) benzamide (Compound 31)

According to the method in Embodiment 1, intermediate 74 (0.2 mmol) and hydroxymethylamine (0.4 mmol) were used to prepare the title compound (31). $^{1}H$ NMR (400 MHz, DMSO-$d_6$) δ 10.40 (s, 1H), 10.22 (s, 1H), 9.96 (s, 1H), 8.58 (d, J=4.9 Hz, 1H), 8.02 (s, 1H), 7.16 (s, 1H), 6.82 (s, 2H), 6.68 (s, 2H), 4.17-4.04 (m, 1H), 3.18 (dd, J=16.8, 9.5 Hz, 1H), 3.07 (s, 3H), 2.62 (dd, J=17.0, 4.1 Hz, 1H), 2.25 (s, 6H).

Embodiment 32 (S)-2-bromo-N-[7-(3,5-dimethylphenoxy)-3-[2-(methoxymethylamino)-2-oxoethyl]-4-methyl-2,5-dioxo-2,3,4,5-tetrahydro-1H-benzo[e][1,4]diazepin-8-yl]-3,4,5-tris (trideuteromethoxy)benzamide (Compound 32)

According to the method in Embodiment 1, intermediate 75 (0.2 mmol) and methoxymethylamine (0.4 mmol) were used to prepare the title compound (32). $^{1}H$ NMR (400 MHz, DMSO-$d_6$) δ 10.53 (s, 1H), 10.24 (s, 1H), 8.04 (s, 1H), 7.17 (s, 1H), 6.83 (s, 2H), 6.68 (s, 2H), 4.42 (dd, J=8.8, 4.8 Hz, 1H), 3.76 (s, 3H), 3.28-3.20 (m, 1H), 3.08 (s, 3H), 3.00 (d, J=15.8 Hz, 1H), 2.92 (s, 3H), 2.25 (s, 6H).

Embodiment 33 (S)-2-bromo-N-[7-(3,5-dimethylphenoxy)-3-[2-(hydroxymethylamino)-2-oxoethyl]-4-methyl-2,5-dioxo-2,3,4,5-tetrahydro-1H-benzo[e][1,4]diazepin-8-yl]-3,4,5-tris (trideuteromethoxy)benzamide (Compound 33)

According to the method in Embodiment 1, intermediate 75 (0.2 mmol) and hydroxymethylamine (0.4 mmol) were used to prepare the title compound (33). $^{1}H$ NMR (400 MHz, DMSO-$d_6$) δ 10.49 (s, 1H), 10.23 (s, 1H), 10.07 (s, 1H), 8.03 (s, 1H), 7.16 (s, 1H), 6.82 (s, 2H), 6.68 (s, 2H), 4.41 (dd, J=8.6, 3.4 Hz, 1H), 3.21 (dd, J=16.5, 9.3 Hz, 1H), 3.07 (s, 3H), 2.94 (d, J=2.7 Hz, 1H), 2.89 (s, 3H), 2.25 (s, 6H).

Embodiment 34 (S)-2-chloro-N-[7-(3,5-dimethylphenoxy)-3-[2-(deuteromethoxydeuteromethylamino)-2-oxoethyl]-4-methyl-2,5-dioxo-2,3,4,5-tetrahydro-1H-benzo[e][1,4]diazepin-8-yl]-3,4,5-tris (trideuteromethoxy)benzamide (Compound 34)

Preparation of deuteromethoxy deuteromethylamine hydrochloride (Intermediate 76): according to the method shown in the FIGURE, benzyl chloroformate (10.0 mmol) was used to prepare it by three steps.

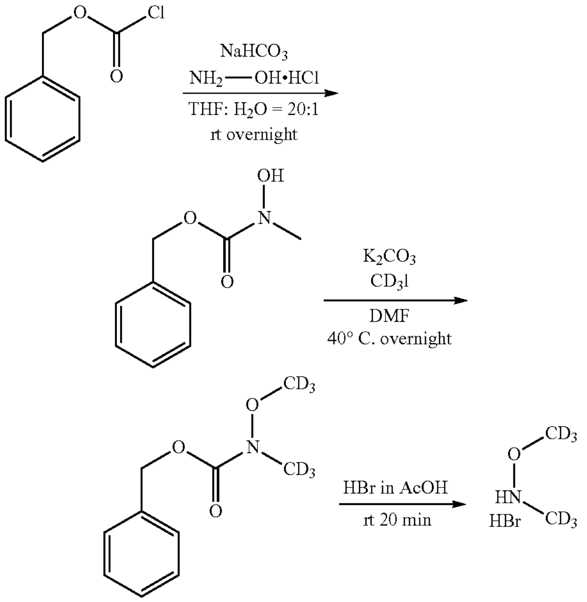

According to the method in Embodiment 1, intermediate 75 (0.2 mmol) and 76 (0.4 mmol) were used to prepare the title compound (34). $^1$H NMR (400 MHz, DMSO-$d_6$) δ 10.52 (s, 1H), 10.21 (s, 1H), 8.04 (s, 1H), 7.17 (s, 1H), 6.83 (s, 1H), 6.81 (s, 1H), 6.68 (s, 2H), 4.43 (dd, J=9.2, 5.1 Hz, 1H), 3.25 (d, J=8.1 Hz, 1H), 2.99 (d, J=15.8 Hz, 1H), 2.92 (s, 3H), 2.25 (s, 6H).

Embodiment 35 (S)-2-chloro-N-[7-(3,5-dimethylphenoxy)-3-[2-(methoxymethylamino)-2-oxoethyl]-2,5-dioxo-2,3,4,5-tetrahydro-1H-benzo[e][1,4]diazepin-8-yl]-3,4,5-tris(trideuteromethoxy) benzamide (Compound 35)

Preparation of (S)-2-(8-(2-chloro-3,4,5-tris(trideuteromethoxy)benzamido)-7-(3,5-dimethylphenoxy)-2,5-dioxo-2,3,4,5-tetrahydro-1H-benzo[e][1,4]diazepin-3-yl]acetic acid (Intermediate 77): according to the method in Embodiment 1, intermediate 45 (2.0 mmol), intermediate 47 (5.0 mmol) and lithium hydroxide (4.0 mmol) were used to prepare it by two steps.

According to the method in Embodiment 1, intermediate 77 (0.5 mmol) and methoxymethylamine (1.0 mmol) were used to prepare the title compound (35). $^1$H NMR (400 MHz, DMSO-$d_6$) δ 10.44 (s, 1H), 10.23 (s, 1H), 8.58 (d, J=5.0 Hz, 1H), 8.02 (s, 1H), 7.17 (s, 1H), 6.84 (s, 1H), 6.81 (s, 1H), 6.68 (s, 2H), 4.13 (dd, J=12.7, 5.5 Hz, 1H), 3.73 (s, 3H), 3.15 (d, J=6.4 Hz, 1H), 3.08 (s, 3H), 2.71 (dd, J=16.8, 4.1 Hz, 1H), 2.25 (s, 6H).

Embodiment 36 (S)-2-chloro-N-[7-(3,5-dimethylphenoxy)-3-[2-(methoxymethylamino)-2-oxoethyl]-4-methyl-2,5-dioxo-2,3,4,5-tetrahydro-1H-benzo[e][1,4]diazepin-8-yl]-3,4,5-tris (trideuteromethoxy)benzamide (Compound 36)

Preparation of (S)-2-(8-(2-chloro-3,4,5-tris(trideuteromethoxy)benzamido)-7-(3,5-dimethylphenoxy)-4-methyl-2,5-dioxo-2,3,4,5-tetrahydro-1H-benzo[e][1,4]diazepin-3-yl]acetic acid (Intermediate 78): according to the method in Embodiment 1, intermediate 57 (2.0 mmol), intermediate 47 (5.0 mmol) and lithium hydroxide (4.0 mmol) were used to prepare it by two steps.

According to the method in Embodiment 1, intermediate 78 (0.5 mmol) and methoxymethylamine (1.0 mmol) were used to prepare the title compound (36). $^1$H NMR (400 MHz, DMSO-$d_6$) δ 10.53 (s, 1H), 10.23 (s, 1H), 8.02 (s, 1H), 7.17 (s, 1H), 6.84 (s, 1H), 6.81 (s, 1H), 6.68 (s, 2H), 4.42 (dd, J=8.7, 5.0 Hz, 1H), 3.75 (s, 3H), 3.24 (d, J=11.4 Hz, 1H), 3.08 (s, 3H), 3.00 (d, J=16.9 Hz, 1H), 2.92 (s, 3H), 2.25 (s, 7H).

Embodiment 37 (S)-2-bromo-N-[7-(3,5-dimethylphenoxy)-3-[2-(deuteromethoxydeuteromethylamino)-2-oxoethyl]-2,5-dioxo-2,3,4,5-tetrahydro-1H-benzo[e][1,4]diazepin-8-yl]-3,4,5-tris (trideuteromethoxy)benzamide (Compound 37)

According to the method in Embodiment 1, intermediate 74 (0.5 mmol) and intermediate 76 (1.0 mmol) were used to prepare the title compound (37). $^1$H NMR (400 MHz, DMSO-$d_6$) δ 10.44 (s, 1H), 10.23 (s, 1H), 8.58 (d, J=5.0 Hz, 1H), 8.02 (s, 1H), 7.16 (s, 1H), 6.82 (s, 2H), 6.68 (s, 2H), 4.12 (dd, J=12.9, 5.3 Hz, 1H), 3.13 (dd, J=17.0, 8.3 Hz, 1H), 2.70 (dd, J=17.1, 4.6 Hz, 1H), 2.25 (s, 6H).

Embodiment 38 (S)-2-chloro-N-[7-(3,5-dimethylphenoxy)-3-[2-(deuteromethoxydeuteromethylamino)-2-oxoethyl]-2,5-dioxo-2,3,4,5-tetrahydro-1H-benzo[e][1,4]diazepin-8-yl]-3,4,5-tris (trideuteromethoxy)benzamide (Compound 38)

According to the method in Embodiment 1, intermediate 77 (0.5 mmol) and intermediate 76 (1.0 mmol) were used to prepare the title compound (38). $^1$H NMR (400 MHz, DMSO-$d_6$) δ 10.44 (s, 1H), 10.23 (s, 1H), 8.58 (d, J=4.7 Hz, 1H), 8.01 (s, 1H), 7.16 (s, 1H), 6.84 (s, 1H), 6.81 (s, 1H), 6.68 (s, 2H), 4.13 (dd, J=12.5, 5.5 Hz, 1H), 3.13 (dd, J=17.4, 6.7 Hz, 1H), 2.70 (dd, J=17.1, 4.9 Hz, 1H), 2.25 (s, 6H).

Embodiment 39 (S)-2-chloro-N-[7-(3,5-dimethylphenoxy)-3-[2-(deuteromethoxydeuteromethylamino)-2-oxoethyl]-4-methyl-2,5-dioxo-2,3,4,5-tetrahydro-1H-benzo[e][1,4]diazepin-8-yl]-3,4,5-tris (trideuteromethoxy)benzamide (Compound 39)

According to the method in Embodiment 1, intermediate 78 (0.5 mmol) and intermediate 76 (1.0 mmol) were used to prepare the title compound (39). $^1$H NMR (400 MHz, DMSO-$d_6$) δ 10.53 (s, 1H), 10.24 (s, 1H), 8.02 (s, 1H), 7.17 (s, 1H), 6.84 (s, 1H), 6.81 (s, 1H), 6.68 (s, 2H), 4.42 (dd, J=9.4, 5.0 Hz, 1H), 3.26 (dd, J=12.7, 10.5 Hz, 1H), 2.99 (dd, J=16.7, 1.7 Hz, 1H), 2.92 (s, 3H), 2.25 (s, 6H).

Embodiment 40 (S)-2-bromo-N-[7-(3,5-dimethylphenoxy)-3-[2-(deuteromethoxymethylamino)-2-oxoethyl]-2,5-dioxo-2,3,4,5-tetrahydro-1H-benzo[e][1,4]diazepin-8-yl]-3,4,5-tris(trideuteromethoxy) benzamide (Compound 40)

According to the method in Embodiment 1, intermediate 74 (0.5 mmol) and deuteromethoxymethylamine hydrobromide (1.0 mmol) were used to prepare the title compound (40). $^1$H NMR (400 MHz, DMSO-$d_6$) δ 10.45 (s, 1H), 10.25 (s, 1H), 8.59 (d, J=5.3 Hz, 1H), 8.03 (s, 1H), 7.16 (s, 1H), 6.83 (s, 1H), 6.82 (s, 1H), 6.69 (s, 2H), 4.13 (dt, J=8.5, 5.4

Hz, 1H), 3.17 (dd, J=16.8, 9.5 Hz, 1H), 3.08 (s, 3H), 2.71 (dd, J=17.2, 5.1 Hz, 1H), 2.26 (s, 6H).

Embodiment 41 (S)-2-bromo-N-[7-(3,5-dimethylphenoxy)-3-[2-(methoxydeuteromethylamino)-2-oxoethyl]-2,5-dioxo-2,3,4,5-tetrahydro-1H-benzo[e][1,4]diazepin-8-yl]-3,4,5-tris(trideuteromethyl)benzamide (Compound 41)

According to the method in Embodiment 1, intermediate 74 (0.5 mmol) and methoxydeuteromethylamine hydrobromide (1.0 mmol) were used to prepare the title compound (41). $^{1}$H NMR (400 MHz, DMSO-$d_6$) δ 10.45 (s, 1H), 10.25 (s, 1H), 8.59 (d, J=4.8 Hz, 1H), 8.03 (s, 1H), 7.16 (s, 1H), 6.82 (s, 1H), 6.82 (s, 1H), 6.69 (s, 2H), 4.22-4.05 (m, 1H), 3.73 (s, 3H), 3.14 (dd, J=16.8, 9.5 Hz, 1H), 2.70 (dd, J=17.0, 4.1 Hz, 1H), 2.26 (s, 6H).

Embodiment 42 Anti-Tumor Activity In Vitro of the Deuterated 1,4-Benzodiazepine-2,5-Dione Compound in the Present Disclosure In this embodiment, the method of National Cancer Institute (NCI) was used to evaluate the anti-tumor activity of the embodiment compounds in the present disclosure. Nine representative cell lines were selected for activity evaluation, including A549 (non-small cell lung cancer), HCT116 (colon cancer), SF295 (central nervous system tumor), LOX-IMVI (melanoma), 786-0 (renal cancer), K562 (leukemia), PC-3 (prostate cancer), OVCAR-3 (ovarian cancer) and HS 578T (breast cancer).

The specific method was as follows: 60 tumor cell lines of 9 kinds of human cancers were used to evaluate the inhibitory activity of the compound in vitro. A test group, a parallel control group and a vehicle control group were set up. The parallel control group was fixed immediately before the compound was added; the cells in the test group were fixed after being treated with the compound for 48 hours; the vehicle control group was fixed after an equal volume of complete medium was added for 48 hours. Sulforhodamine B (SRB) was used to stain, and the OD value was measured at a wavelength of 515 nm. The specific calculation method was as follows: the OD value of the parallel control group was recorded as Tz, the OD value of the vehicle control group was recorded as C, and the OD value of the test group was recorded as (Ti). If Ti≥Tz, it means that the cells still grow after the drug was added, and the growth rate %=[(Ti−Tz)/(C−Tz)]×100; if Ti<Tz, it means that the cells are killed after the drug was added, and the growth rate %=[(Ti−Tz)/Tz]×100. Three parameters were used to evaluate the anti-tumor activity of compounds in this method: 50% growth inhibitory concentration ($GI_{50}$): i.e. the compound concentration at [(Ti−Tz)/(C−Tz)]×100=50; complete growth inhibitory concentration (TGI): the compound concentration at Ti=Tz; the drug concentration required to kill 50% of the cells ($LC_{50}$): i.e. the compound concentration at [(Ti−Tz)/Tz]×100=−50.

The evaluation results showed that most of the compounds of the embodiments in the present disclosure had significant activity of inhibiting the growth of tumor cells.

The inhibitory activities of the embodiment compounds on nine representative tumor cell lines were listed in detail in Table 1. Wherein, the $GI_{50}$ value means "50% growth inhibition rate", that is, the concentration of the compound to be tested when it can inhibit 5000 of cell growth; "ND" means not detected.

TABLE 1

| | $GI_{50}$ (nM) | | | | | | | | |
|---|---|---|---|---|---|---|---|---|---|
| No. | A549 | 786-0 | HCT116 | K562 | PC-3 | LOX-IMVI | SF295 | OVCAR-3 | HS578T |
| 1 | 15.0 | 8.1 | 5.4 | <5.0 | 5.5 | <5.0 | 12.3 | 5.5 | 31.6 |
| 2 | 13.1 | 11.8 | <5.0 | <5.0 | 5.5 | <5.0 | 7.9 | 6.1 | 30.8 |
| 3 | <5.0 | 110.1 | 11.2 | 8.4 | 43.9 | 18.4 | 53.2 | 28.6 | 91.9 |
| 4 | <5.0 | 11.9 | <5.0 | <5.0 | <5.0 | <5.0 | 6.0 | <5.0 | ND |
| 5 | <5.0 | 26.1 | <5.0 | <5.0 | <5.0 | <5.0 | 17.4 | <5.0 | <5.0 |
| 6 | 11.7 | 16.9 | <5.0 | <5.0 | 10.3 | <5.0 | 13.1 | 11.9 | 20.5 |
| 7 | <5.0 | 6.5 | <5.0 | ND | <5.0 | <5.0 | <5.0 | <5.0 | 8.2 |
| 8 | 15.3 | 13.9 | <5.0 | <5.0 | 9.7 | <5.0 | 10.3 | 5.0 | 13.3 |
| 9 | 23.0 | 44.8 | 14.8 | 17.0 | 13.1 | 13.9 | 15.2 | 8.6 | 40.5 |
| 10 | 35.4 | 37.0 | 34.7 | <5.0 | <5.0 | <5.0 | 10.7 | <5.0 | 6.4 |
| 11 | <5.0 | 10.4 | 15.7 | <5.0 | <5.0 | <5.0 | 10.9 | <5.0 | <5.0 |
| 12 | <5.0 | 9.9 | <5.0 | <5.0 | 5.4 | <5.0 | 10.8 | 12.6 | 13.3 |
| 13 | <5.0 | 11.5 | <5.0 | <5.0 | <5.0 | <5.0 | 7.5 | <5.0 | <5.0 |
| 14 | <5.0 | 5.0 | <5.0 | <5.0 | <5.0 | <5.0 | <5.0 | <5.0 | ND |
| 15 | <5.0 | 6.2 | ND | <5.0 | <5.0 | <5.0 | <5.0 | <5.0 | ND |
| 16 | <5.0 | 11.2 | <5.0 | <5.0 | <5.0 | <5.0 | 7.6 | <5.0 | <5.0 |
| 17 | 15.8 | 10.0 | 44.9 | <5.0 | <5.0 | <5.0 | 8.0 | 8.4 | 5.6 |
| 18 | <5.0 | <5.0 | <5.0 | <5.0 | <5.0 | <5.0 | <5.0 | <5.0 | 15.4 |
| 19 | 5.9 | 19.7 | 5.0 | <5.0 | <5.0 | <5.0 | 11.8 | 6.2 | 80.7 |
| 20 | <5.0 | 26.5 | <5.0 | <5.0 | <5.0 | <5.0 | 19.9 | <5.0 | <5.0 |
| 21 | 6.1 | 12.9 | <5.0 | <5.0 | <5.0 | <5.0 | 11.3 | <5.0 | ND |
| 22 | <5.0 | 12.6 | 7.1 | <5.0 | <5.0 | <5.0 | 10.0 | <5.0 | ND |
| 23 | 11.6 | 67.5 | <5.0 | <5.0 | 6.1 | <5.0 | 10.5 | 6.6 | 24.9 |
| 24 | 207.4 | 276.5 | 123.0 | 25.5 | 39.5 | 65.8 | 135.0 | 87.6 | 188.0 |
| 25 | 19.1 | 15.8 | <5.0 | <5.0 | 5.0 | <5.0 | 14.2 | 8.3 | 30.3 |
| 26 | 13 | 57.4 | 14.2 | <5.0 | <5.0 | 6.2 | 42.7 | 6.0 | 10.0 |
| 27 | ND | ND | ND | ND | ND | ND | ND | ND | ND |
| 28 | <5.0 | 66.0 | <5.0 | <5.0 | <5.0 | <5.0 | 18.0 | <5.0 | <5.0 |
| 29 | 11.8 | 244 | 12.0 | 4.2 | <5.0 | <5.0 | 93.8 | <5.0 | <5.0 |
| 30 | 4.9 | 8.6 | 7.8 | 1.6 | <5.0 | <5.0 | 11.6 | <5.0 | <5.0 |
| 31 | <5.0 | 28.1 | 17.0 | <5.0 | <5.0 | <5.0 | 58.0 | <5.0 | 8.6 |
| 32 | <5.0 | <5.0 | <5.0 | <5.0 | <5.0 | <5.0 | 5.0 | <5.0 | <5.0 |
| 33 | <5.0 | 27.0 | 8.0 | <5.0 | <5.0 | <5.0 | 29.0 | <5.0 | 7.9 |
| 34 | <5.0 | <5.0 | <5.0 | <5.0 | <5.0 | <5.0 | <5.0 | <5.0 | <5.0 |

TABLE 1-continued

| | GI$_{50}$ (nM) | | | | | | | | |
|---|---|---|---|---|---|---|---|---|---|
| No. | A549 | 786-0 | HCT116 | K562 | PC-3 | LOX-IMVI | SF295 | OVCAR-3 | HS578T |
| 35 | <5.0 | 21.1 | 9.8 | <5.0 | <5.0 | 5.6 | 29.0 | <5.0 | 16.0 |
| 36 | <5.0 | 11.9 | <5.0 | <5.0 | <5.0 | <5.0 | 10.0 | <5.0 | 8.5 |
| 37 | <5.0 | 8.6 | <5.0 | <5.0 | <5.0 | <5.0 | 12.0 | <5.0 | <5.0 |
| 38 | <5.0 | 23.0 | 13.0 | <5.0 | <5.0 | 5.2 | 27.0 | <5.0 | 21.0 |
| 39 | <5.0 | 9.0 | 7.0 | <5.0 | <5.0 | <5.0 | 12.0 | <5.0 | 6.0 |
| 40 | <5.0 | <5.0 | <5.0 | <5.0 | <5.0 | <5.0 | <5.0 | <5.0 | <5.0 |
| 41 | <5.0 | <5.0 | <5.0 | <5.0 | <5.0 | <5.0 | <5.0 | <5.0 | <5.0 |

As can be seen above, the anti-tumor activity in vitro was significantly reduced when only the H on the benzene ring in the general compound was deuterated; whereas the compound of the present disclosure maintained the activity of inhibiting tumor cells and tumor stem cells.

Embodiment 43 Liver Microsomes Stability of the Deuterated 1,4-Benzodiazepine-2,5-Dione Compound in the Present Disclosure The compound to be tested with final concentration of 1 μM was incubated with 1 mg/mL of human liver microsomes and 1 mM of NADPH, and a group without NADPH was set as a negative control. The reaction mixture was quenched with methanol at five time points of 0, 5, 15, 30 and 60 min, respectively, then centrifuged at 2500 rpm for 20 min to precipitate proteins, and the resulting supernatant was analyzed by LC-MS/MS. The data was analyzed and the k value and half-life $T_{1/2}$ was calculated, $T_{1/2}$(min)=0.693/k.

The half-life $T_{1/2}$ and clearance Clint of the target compounds in liver microsomes in vitro are listed in Table 2. Wherein, compounds a, b and c are active compounds disclosed in patent No. ZL201610154581.3. By comparison, it is found that the half-life of the deuterated compounds disclosed in the present disclosure is significantly prolonged and the metabolic stability is significantly enhanced compared with previous compounds, such as compounds 1 (42 min), 3 (38 min), 6 (73 min), 7 (49.9 min), 8 (50.6 min), 9 (117 min), 10 (68 min), 13 (46.8 min), 16 (56.9 min), 19 (32.9 min), 20 (330 min), etc.

TABLE 2 a

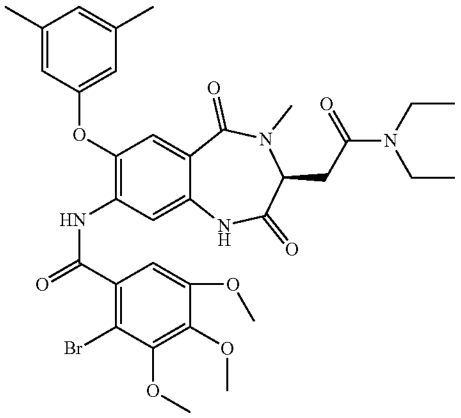 [SMILES: CCN(CC)C(=O)C[C@H]1C(=O)Nc2cc(NC(=O)c3cc(OC)c(OC)c(OC)c3Br)c(Oc3cc(C)cc(C)c3)cc2C(=O)N1C]

b

TABLE 2-continued

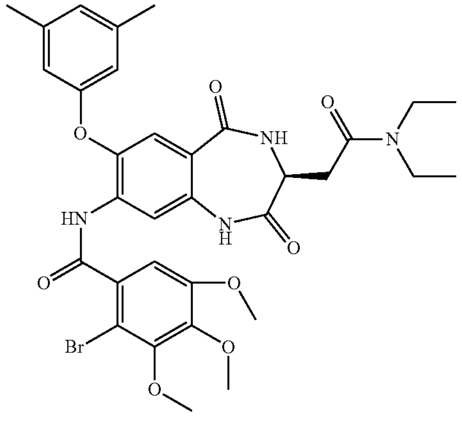 [SMILES: CCN(CC)C(=O)C[C@@H]1NC(=O)c2cc(Oc3cc(C)cc(C)c3)c(NC(=O)c3cc(OC)c(OC)c(OC)c3Br)cc2NC1=O]

c

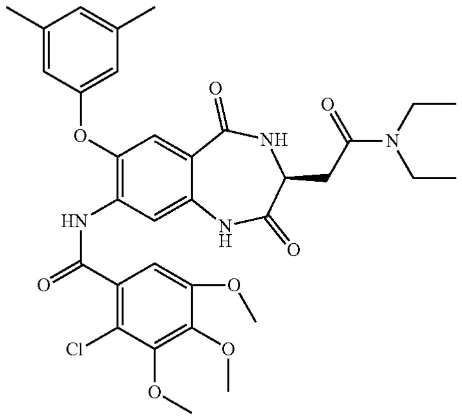

| No. | T½ of HLM (min) | CLint (μL/min/mg protein) |
|---|---|---|
| a | 11.0 | 63.1 |
| b | 26.3 | 26.4 |
| c | 26.2 | 26.5 |
| 1 | 42.0 | 16.5 |
| 2 | 21.7 | 32.0 |
| 3 | 38.3 | 18.1 |
| 4 | 33.8 | 20.5 |
| 5 | **217** | **3.20** |
| 6 | 73.0 | 9.50 |
| 7 | 49.9 | 13.9 |
| 8 | 50.6 | 13.7 |
| 9 | 117 | 5.90 |
| 10 | 68.0 | 10.2 |
| 11 | 24.6 | 28.2 |
| 12 | 22.6 | 30.7 |
| 13 | 46.8 | 14.8 |
| 14 | 61.3 | 11.3 |
| 15 | 64.2 | 10.8 |

TABLE 2-continued

| | | |
|---|---|---|
| 16 | **59.8** | **11.6** |
| 17 | 20.1 | 34.5 |
| 18 | 10.6 | 65.1 |
| 19 | 32.9 | 21.1 |
| 20 | **330** | **2.10** |
| 22 | 151 | 4.6 |
| 23 | 25.8 | 26.9 |
| 24 | 24.4 | 28.4 |
| 25 | 23.3 | 29.8 |
| 26 | 217 | 3.2 |
| 27 | 48.1 | 14.4 |
| 28 | 41.8 | 16.8 |
| 29 | 128 | 5.4 |
| 30 | 161 | 4.30 |
| 31 | 43.3 | 16.0 |
| 32 | 24.7 | 28.1 |
| 33 | 55.9 | 12.4 |
| 34 | 72.2 | 9.6 |
| 35 | 59.2 | 11.7 |
| 36 | 102 | 6.80 |
| 37 | 90.0 | 7.70 |
| 38 | 96.3 | 7.20 |
| 39 | 50.6 | 13.7 |
| 40 | 77.0 | 9.00 |
| 41 | 91.2 | 7.60 |

From the above effects, the following structure-activity relationship can be preliminarily obtained: (1) for the moiety

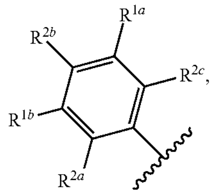

deuteration modifications do not contribute significantly to the metabolic stability of the molecule, and when only $R^{2a}$, $R^{2b}$ and $R^{2c}$ are deuterium, it may reduce the anti-cancer activity of the molecule; (2) for the moiety

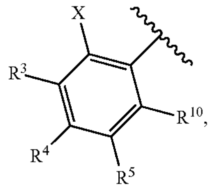

when $R^3$, $R^4$ and $R^5$ are deuterated methoxy groups, it can enhance the metabolic stability of the molecule; the effect of halogen atoms in X on the metabolism of the molecule is Br>Cl; (3) for the moiety

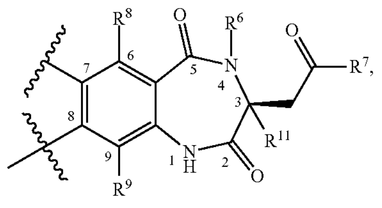

when $R^6$ in N-4 position is H, $R^7$ is a deuterium modified group, it enhances the metabolic stability of the compound; $R^6$ in N-4 position is a deuterium modified group, such as deuterated methyl, and the deuterium modified group of $R^6$ and $R^7$ does not significantly contribute to the metabolic stability of the molecule, but when $R^7$ is dimethylamino, the metabolic stability of the compound is better.

Embodiment 44 Metabolic Stability In Vivo of the Deuterated 1,4-Benzodiazepine-2,5-Dione Compound in the Present Disclosure 1. Test Drug The intravenous injection group of the embodiment compound was prepared with the mixed solvent of DMA: PEG400:30% SBECD=5:25:70 to form a 0.2 mg/mL of solution, and administered intravenously at 1 mg/kg of weight; and the oral preparation group was prepared with 0.5% MC to form a 1 mg/mL of solution, and administered by oral gavage at 10 mg/kg weight.

2. Test Animal:

Male BALB/c nude mice, 4-5 weeks old, purchased from Shanghai SLAC.

3. Experiment Method:

3.1 Instruments:

Liquid chromatography system: Shimadzu liquid chromatography system Shimadzu LC-30AD MS/MS system: Applied Biosystems API5500

Data collection: Analyst Software 1.5.2

3.2 Chromatographic Conditions

Chromatographic Column

Analytical column: Kinetex 2.6u C18 100 A column (3.0 mm×30 mm)

Mobile phase: A: 10 mM $NH_4OAc$ (0.1% FA); B: Acetonitrile with 0.1% A

Flow rate: 1.0 mL/min

TABLE 3

| Gradient: | | | |
|---|---|---|---|
| Time (min) | Flow Rate (mL/min) | A (%) | B (%) |
| 0.40 | 1.0 | 95 | 5 |
| 1.50 | 1.0 | 5 | 95 |
| 2.00 | 1.0 | 5 | 95 |
| 2.00 | 1.0 | 95 | 5 |
| 2.50 | 1.0 | 95 | 5 |

Injection volume: 10.0 μL

Column temperature: RT

Mass Spectrometry Conditions

Ion source was an electron spray ionization (ESI source) with negative ion detection; spray voltage source was 5500 V; ion source gas 1 ($N_2$) was 50 psi; ion source gas 2 ($N_2$) was 50 psi; air curtain gas ($N_2$) was 30 psi. Scanning mode was multiple reaction monitoring (MRM); scanning time was 80 ms; collision gas pressure was 10 psi;

3.3 Pretreatment of Plasma Sample

Grouping experiment, with three animals in each group, starting from now on, administration was started according to the weight of the animals. Blood was collected according to 5 min, 15 min, 30 min, 1 h, 2 h, 4 h, 8 h and 24 h after administration.

Compound Measurement

To 25.0 μL of plasma, 25.0 μL of internal standard solution (Tolbutamide (250 ng/mL) in acetonitrile), 25.0 μL of acetonitrile and 100 μL of acetonitrile were added, and the mixture was vortexed for 1 min, and centrifuged for 5 min (14000 rpm). 120 μL of the resulting supernatant was added with 80.0 μL of water (containing 1% formic acid) and mixed well, then analyzed by LC/MS/MS.

TABLE 4 a

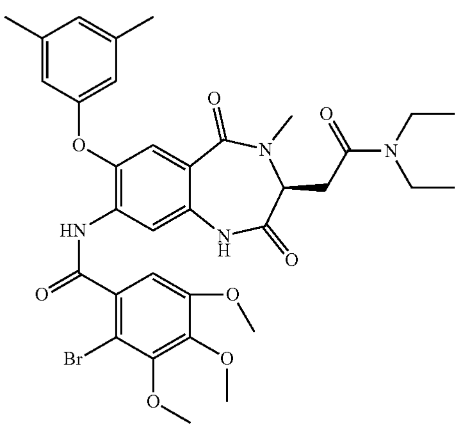 [SMILES: CCN(CC)C(=O)C[C@H]1C(=O)Nc2cc(NC(=O)c3cc(OC)c(OC)c(OC)c3Br)c(Oc3cc(C)cc(C)c3)cc2C(=O)N1C]

b

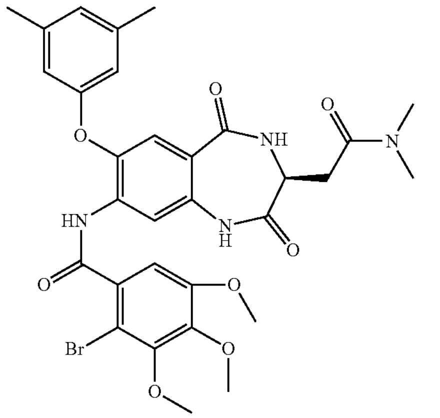

| Compd. | T½ of HLM (in vitro) (min) | T½ of (IV in nude mice) (h) |
|---|---|---|
| a | 11.0 | 0.531 |
| d | 100 | 0.777 |
| 1 | 42.0 | 0.885 |
| 5 | 217 | 1.52 |
| 6 | 73.0 | 1.31 |
| 8 | 50.6 | 0.634 |
| 12 | 22.6 | 0.566 |
| 16 | 59.8 | 0.585 |
| 20 | 330 | 0.800 |

As can be seen from the above, comparing compound 13 with comparative compound a, comparing compound 5, 7 with comparative compound b, comparing compound 6, 8 with comparative compound c, and comparing compound 20, 22 with comparative compound d, a series of embodiment compounds disclosed in the present disclosure can effectively prolong the metabolic stability of liver microsomes in vitro of the active compounds disclosed in the patent NO. ZL201610154581.3; and the in vivo DMPK experiment results show that the in vivo half-life of the disclosed compound can also be enhanced.

Embodiment 45 the Embodiment Compound has the Ability of Killing Breast Cancer Stem Cells and Inhibiting Self-Renewal Thereof A series of embodiment compounds disclosed in the present disclosure can not only effectively inhibit the growth of tumor cells, but also inhibit the proliferation of tumor stem cells in vitro and in vivo as proved by experiments, which is expected to be developed into a bifunctional drug that inhibits both tumor cells and tumor stem cells.

Tumor stem cells can form spheres under appropriate in vitro culture conditions, while tumor cells do not have this ability, according to which tumor stem cells can be isolated under in vitro conditions and used to evaluate the effect of drugs on their proliferation and differentiation. The inhibitory effects of embodiment compounds 5, 7, 11, 13, 14, 20 and 21 on the formation of breast cancer cell line SUM159 sphere are described as follows.

Cultivation of Sphere:

The breast cancer cell line SUM159 sphere was cultured with serum-free medium in an ultra-low adsorption plate, the basal medium was DMEM/F12 (without phenol red), and B27 (without vitamin A) (1×), EGF (20 ng/ml), bFGF (20 ng/ml) and insulin (insulin, 5 ug/ml) were added.

Drug Treatment Experiment of Sphere;

An equal number (4000) of SUM159 cells per well were inoculated into an ultra-low adsorption 24 plate, and the sphere was photographed after 5 days of culture, replaced with fresh medium, and treated with drugs at certain concentrations, respectively. Compounds 5, 7, 11, 13, 14, 20 and 21 were evaluated in this experiment at 50 nM, respectively. The effect of the drug on the sphere phenotype could be observed after about 3 days of drug treatment. The sphere was photographed again after 5 days of drug treatment, and then the sphere was passaged. The sphere was photographed again after 7 days of passage.

The differences of the photographs taken in three different stages were counted and compared, and the killing effect of the tested compounds on SUM159 sphere was evaluated through the differences of sphere formation after passage, thus reflecting the inhibitory effects of different compounds on breast cancer stem cells.

Experimental Results and Discussion:

After treatment with the test compounds 5, 7, 11, 13, 14, 20 and 21. The formation of the sphere was significantly reduced after cell passage. The specific shape of sphere was listed in FIG. 1.

The experimental results showed that the compounds 5, 7, 11, 13, 14, 20 and 21 all had a strong killing effect on SUM159 sphere, indicated it lose the ability of self-renewal.

In addition, the above experiments confirmed that the tested embodiment compounds 5, 7, 11, 13, 14, 20 and 21 all can inhibit breast cancer stem cells and their ability of self-renewal, showing that such compounds have the effect of killing tumor stem cells.

Embodiment 46 the Inhibition Effect of Embodiment Compounds on Growth of Xenograft Tumor of Human Cancer in Nude Mice 1. Test Drug The embodiment compound was prepared as a 40× stock solution of DMSO and diluted to the administered concentration with saline containing 2.5% Tween 80 (Tween 80) used before;

2. Test Animal and Tumor Line:

Male BALB/c nude mice, 4-5 weeks old, were purchased from Beijing Vital River Laboratory Animal Technology Co., Ltd, with a license No. SCXK(Beijing)2012-0001, and the mice were bred in the SPF-class laboratory animal center of Tsinghua University. The tumor lines used in the experiment were: xenograft of human lung cancer NCI-H522 in nude mice, xenograft of human colon cancer HCT-116 in nude mice.

3. Experiment Method:

Tumor-bearing animals with good tumor growth and overall condition were selected and sacrificed by cervical dislocation. The tumors were removed under aseptic condition, cut into tumors with 2-3 mm diameter by a scalpel, and inoculated subcutaneously behind the armpit of nude mice by trocar. The tumors grew naturally and were randomly grouped after the tumor volume grew to 105 $mm^3$, and the administration date of grouping was set as D0 (Day 0).

Grouping experiment, with 7-9 animals in each group, starting from now on, administration was started according to the weight of the animals. During the administration process, the long, short diameter of the tumors and weight of animals were measured every 2-3 days, and the tumor size was calculated by the formula: (½)×long diameter×(short diameter)$^2$, and the experiment was ended on the 27$^{th}$ day (D27) after grouping. At the end of the experiment, the animals were sacrificed by cervical dislocation, the tumors were peeled off and weighed, and the inhibitory rates of the drugs on tumor growth were calculated. Tumor volume (TV) and relative tumor volume (RTV) were calculated. T test was used to compare the statistical significance of the differences in tumor weight, tumor volume and RTV of the animals in each group.

Calculation formulas are as follows:

average tumor weight in the vehicle control group−average tumor weight in the treatment group Tumor inhibition rate (%)=(average tumor weight in the vehicle control group−average tumor weight in the treatment group)÷(average tumor weight in the vehicle control)×100.

Tumor volume (TV)=(length×width$^2$)/2.

Relative tumor volume (RTV)=Vt/Vo (wherein, Vo is the TV measured at the time of grouping and administration, and Vt is the TV at each subsequent measurement).

The evaluation index of anti-tumor activity is the relative tumor proliferation rate T/C (%):

$$T/C(\%) = \frac{\text{The treatment group } (T)\ RTV}{\text{The vehicle control group } (C)\ RTV} \times 100.$$

Efficacy evaluation criteria: T/C (%)>40 is invalid;

T/C (%)≤40, and P<0.05 is effective after statistical processing.

4. Experiment Results and Discussion:

The compound 5 in the present disclosure was used to evaluate the tumor inhibition ability in vivo on the xenograft of NCI-H522 lung cancer in mice. As can be seen from the results in Table 5, the in vivo anti-tumor ability of the compound 5 was significantly enhanced compared with the active compound disclosed in the patent NO. ZL201610154581.3, when the high-dose group was administered at a concentration of 50 mg/kg, the relative tumor inhibition rate T/C (%) value of the compound was 14.2, and the tumor inhibition rate reached 90.02%.

TABLE 5

Evaluation of anti-tumor activity on xenograft of NCI-H522 in nude mice

| Group | Treatment | No. of mice (initial/final) | Tumor weight inhibition (%) | T/C (%) | P-Value |
|---|---|---|---|---|---|
| Control | iv., q4d × 6 | 7/7 | — | — | — |
| 5 (50 mg/kg) | iv., q4d × 6 | 6/7 | 90.02 | 14.2 | <0.01 |
| 5 (25 mg/kg) | iv., q4d × 6 | 7/7 | 84.20 | 21.2 | <0.01 |
| 5 (12.5 mg/kg) | iv., q4d × 6 | 7/7 | 72.03 | 31.7 | <0.01 |

The embodiment compounds 5, 16 and 20 disclosed in the present disclosure were experimentally confirmed to inhibit the growth of xenograft of human intestinal cancer HCT-116 in nude mice, indicating that such compounds are expected to be developed as tumor-inhibiting drugs.

TABLE 6

Inhibition effect of the embodiment compounds on HCT116 tumor growth (mean ± SD)

| Groups | Treatment method | Number (start/end) | Tumor weight inhibition rate (%) | Relative tumor proliferation rate (%) | P value |
|---|---|---|---|---|---|
| Control group | Intravenous injection every other day × 9 | 9/9 | — | — | — |
| Embodiment compound 16 (16 mg/kg) | Intravenous injection every other day × 9 | 9/8 | 63.4 | 38 | <0.001 |
| Embodiment compound 5 (20 mg/kg) | Intravenous injection every other day × 3 | 9/9 | 69.6 | 34 | <0.001 |
| Embodiment compound 20 (20 mg/kg) | Intravenous injection every other day × 9 | 9/9 | 75.4 | 30 | <0.001 |

As can be seen from the tumor growth curve and Table 5, the growth rate of the tumor volume of mice in each treatment group of the embodiment compounds was significantly slower than that of the vehicle control group. At the end of the experiment, the T/C values of embodiment compounds 5, 16 and 20 were 34%, 38%, and 30%, respectively, and the tumor inhibition rates were 69.6%, 63.4%, and 75.4%, respectively. It has statistical significance ($p<0.001$). In this experiment, the embodiment compounds can be evaluated as effective.

Although the specific embodiments of the present disclosure have been described above, those skilled in the art should understand that these are only examples, various changes or modifications can be made to these embodiments without departing from the principle and essence of the present disclosure. Therefore, the protection scope of the present disclosure is defined by the appended claims.

What is claimed is:

1. A compound represented by formula I or a pharmaceutically acceptable salt thereof,

I

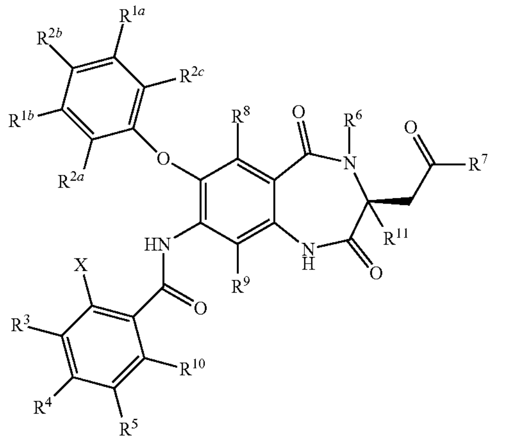

wherein, X is hydrogen, fluorine, chlorine, bromine or iodine;

$R^{1a}$ and $R^{1b}$ are independently hydrogen, deuterium, $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl, $C_{2-4}$ alkenyl, $C_{2-4}$ alkynyl or deuterated $C_{1-3}$ alkyl;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently $C_{1-3}$ alkyl, deuterated $C_{1-3}$ alkyl or deuterated $C_{1-3}$ alkyl-O—; $R^{15}$ and $R^{16}$ are independently H, $C_{1-3}$ alkyl or deuterated $C_{1-3}$ alkyl;

$R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—;

or, $R^{13}$ and $R^{14}$ together with the attached nitrogen atom form: a 4- to 6-membered aliphatic heterocycle or a 4- to 6-membered aliphatic heterocycle substituted by one or more $R^{19}$; the 4- to 6-membered aliphatic heterocycle in the 4- to 6-membered aliphatic heterocycle and the 4- to 6-membered aliphatic heterocycle substituted by one or more $R^{19}$ contains 0-2 heteroatoms selected from N, O or S, besides the 1 N attached to the shown carbonyl;

$R^{19}$ is halogen, O═, $C_{1-3}$ alkyl or deuterated $C_{1-3}$ alkyl;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group.

2. The compound represented by formula I or the pharmaceutically acceptable salt thereof according to claim 1, wherein, the compound satisfies any one of the following conditions:

(1) X is chlorine or bromine;

(2) $R^{1a}$ and $R^{1b}$ are the same;

(3) $R^{1a}$ and $R^{1b}$ are independently $C_{1-3}$ alkyl or deuterated $C_{1-3}$ alkyl;

(4) $R^{2a}$, $R^{2b}$ and $R^{2c}$ are the same;

(5) $R^{2a}$, $R^{2b}$ and $R^{2c}$ are independently hydrogen;

(6) any two or three of $R^3$, $R^4$ and $R^5$ are the same;

(7) $R^3$, $R^4$ and $R^5$ are independently $C_{1-3}$ alkyl-O—, deuterated $C_{1-3}$ alkyl or deuterated $C_{1-3}$ alkyl-O—;

(8) $R^6$ is H, $C_{1-3}$ alkyl, $C_{2-4}$ alkynyl or deuterated $C_{1-3}$ alkyl;

(9) when $R^7$ is —$OR^{12}$, $R^{12}$ is $C_{1-3}$ alkyl or deuterated $C_{1-3}$ alkyl;

(10) when $R^7$ is —$NR^{13}R^{14}$, $R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—;

(11) when $R^7$ is —$NR^{13}R^{14}$, $R^{13}$ and $R^{14}$ together with the attached nitrogen atom form: a 4- to 6-membered aliphatic heterocycle or a 4- to 6-membered aliphatic heterocycle substituted by one or more $R^{19}$, $R^{19}$ is independently halogen, O═, $C_{1-3}$ alkyl or deuterated $C_{1-3}$ alkyl;

(12) when $R^7$ is —$C(R^{15}R^{16})$—P(═O)($OR^{17}OR^{18}$), $R^{15}$ and $R^{16}$ are independently $C_{1-3}$ alkyl;

(13) when $R^7$ is —$C(R^{15}R^{16})$—P(═O)($OR^{17}OR^{18}$), $R^{15}$ and $R^{16}$ are the same;

(14) when $R^7$ is —$C(R^{15}R^{16})$—P(═O)($OR^{17}OR^{18}$), $R^{17}$ and $R^{18}$ are the same;

(15) when $R^7$ is —$C(R^{15}R^{16})$—P(═O)($OR^{17}OR^{18}$), $R^{17}$ and $R^{18}$ are independently $C_{1-3}$ alkyl;

(16) $R^8$ is hydrogen;

(17) $R^9$ is hydrogen;

(18) $R^{10}$ is hydrogen;

(19) $R^{11}$ is hydrogen;

(20) $R^6$ is hydrogen, $R^7$ is —$OR^{12}$, —$C(R^{15}R^{16})$—P(═O)($OR^{17}OR^{18}$), —$NR^{13}R^{14}$; and (21) at least one of $R^{1a}$, $R^{1b}$, $R^3$, $R^4$, $R^5$, $R^6$ and $R^7$ is deuterium or a deuterated group.

3. The compound represented by formula I or the pharmaceutically acceptable salt thereof according to claim 1, wherein, the compound satisfies any one of the following conditions:

(1) X is bromine;

(2) $R^{1a}$ and $R^{1b}$ are independently $C_{1-3}$ alkyl;

(3) $R^3$, $R^4$ and $R^5$ are the same:

(4) $R^3$, $R^4$ and $R^5$ are independently $C_{1-3}$ alkyl-O— or deuterated $C_{1-3}$ alkyl-O—;

(5) $R^6$ is H, $C_{1-3}$ alkyl or deuterated $C_{1-3}$ alkyl;

(6) $R^{12}$ is deuterated $C_{1-3}$ alkyl;

(7) when $R^7$ is —$NR^{13}R^{14}$, $R^{13}$ is OH, $C_{1-3}$ alkyl, deuterated $C_{1-3}$ alkyl, $C_{1-3}$ alkyl-O— or deuterated $C_{1-3}$ alkyl-O—; $R^{14}$ is $C_{1-3}$ alkyl or deuterated $C_{1-3}$ alkyl;

(8) when $R^7$ is —$NR^{13}R^{14}$, $R^{13}$ and $R^{14}$ together with the attached nitrogen atom form: a 4- to 6-membered aliphatic heterocycle or a 4- to 6-membered aliphatic heterocycle substituted by one or more $R^{19}$, the 4- to 6-membered aliphatic heterocycle in the 4- to 6-membered aliphatic heterocycle and the 4- to 6-membered aliphatic heterocycle substituted by one or more $R^{19}$ contains 0-1 heteroatoms optionally selected from N, O or S, besides the 1 N attached to the shown carbonyl:

(9) when $R^7$ is —$C(R^{15}R^{16})$—$P({=}O)(OR^{17}OR^{18})$, $R^{15}$ and $R^{16}$ are independently methyl;

(10) when $R^7$ is —$C(R^{15}R^{16})$—$P({=}O)(OR^{17}OR^{18})$, $R^{17}$ and $R^{18}$ are independently methyl;

(11) $R^{19}$ is independently halogen, O═ or $C_{1-3}$ alkyl;

(12) at least one of $R^3$, $R^4$, $R^5$, $R^6$ and $R^7$ is deuterium or a deuterated group;

(13) when $R^{1a}$ and Rib are independently $C_{1-3}$ alkyl or deuterated $C_{1-3}$ alkyl, the $C_{1-3}$ alkyl in the $C_{1-3}$ alkyl and the deuterated $C_{1-3}$ alkyl is methyl, ethyl, n-propyl or isopropyl;

(14) when $R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—, the $C_{1-3}$ alkyl in the $C_{1-3}$ alkyl, $C_{1-3}$ alkyl-O—, deuterated $C_{1-3}$ alkyl and deuterated $C_{1-3}$ alkyl-O— is methyl, ethyl, n-propyl or isopropyl;

(15) when Re is $C_{1-3}$ alkyl or deuterated $C_{1-3}$ alkyl, the $C_{1-3}$ alkyl in the $C_{1-3}$ alkyl and the deuterated $C_{1-3}$ alkyl is methyl, ethyl, n-propyl or isopropyl;

(16) when $R^6$ is $C_{2-4}$ alkenyl, the $C_{2-4}$ alkenyl is vinyl, 1-propenyl,

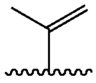 or 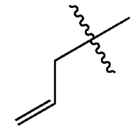 ;

(17) when $R^6$ is $C_{2-4}$ alkynyl, the $C_{2-4}$ alkynyl is ethynyl or

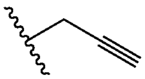 ;

(18) when $R^{12}$, $R^{17}$ and $R^{18}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl is methyl, ethyl, n-propyl or isopropyl;

(19) when $R^{15}$ and $R^{16}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl are methyl, ethyl, n-propyl or isopropyl;

(20) when $R^{13}$ and $R^{14}$ are independently $C_{1-3}$ alkyl, deuterated $C_{1-3}$ alkyl, $C_{1-3}$ alkyl-O— or deuterated $C_{1-3}$ alkyl-O—, the $C_{1-3}$ alkyl in the $C_{1-3}$ alkyl, deuterated $C_{1-3}$ alkyl, $C_{1-3}$ alkyl-O— or deuterated $C_{1-3}$ alkyl-O— is methyl, ethyl, n-propyl or isopropyl;

(21) when $R^{13}$ and $R^{14}$ together with the attached nitrogen atom form: a 4- to 6-membered aliphatic heterocycle or a 4-6-membered aliphatic heterocycle substituted by one or more $R^{19}$, the 4- to 6-membered aliphatic heterocycle in the 4- to 6-membered aliphatic heterocycle and the 4- to 6-membered aliphatic heterocycle substituted by one or more $R^{19}$ is 4- to 6-membered aliphatic heterocycle, wherein containing 0-1 heteroatoms selected from N, O or S, besides the 1 N attached to the shown carbonyl;

(22) when $R^{19}$ is halogen, the halogen is fluorine, chlorine, bromine or iodine; and

(23) when $R^{19}$ is $C_{1-3}$ alkyl or deuterated $C_{1-3}$ alkyl, the $C_{1-3}$ alkyl in the $C_{1-3}$ alkyl and the deuterated $C_{1-3}$ alkyl is methyl, ethyl, n-propyl or isopropyl.

4. The compound represented by formula I or the pharmaceutically acceptable salt thereof according to claim 1, wherein, the compound satisfies any one of the following conditions:

(1) $R^{1a}$ and $R^{1b}$ are independently methyl or CD;

(2) $R^3$, $R^4$ and $R^5$ are independently methyl-O—, $CD_3$, —$CD_2$-$CD_3$ or $CD_3$-O—;

(3) $R^6$ is H, methyl or $CD_3$;

(4) $R^{12}$ is $CD_3$;

(5) $R^{13}$ is OH, methyl, ethyl, $CD_3$, —$CD_2$-$CD_3$ or $CD_3$-O—, and $R^{14}$ is $CD_3$ or —$CD_2$-$CD_3$; or, $R^{13}$ and $R^{14}$ together with the attached nitrogen atom form:

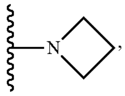, 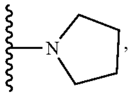, 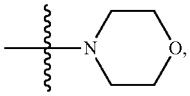,

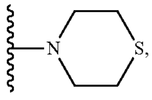, 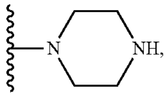, 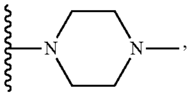,

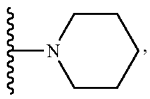, 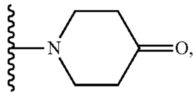,

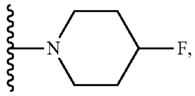, 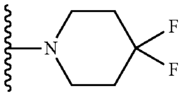 or

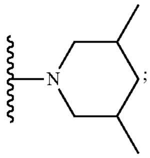;

(7) —$C(R^{15}R^{16})$—$P({=}O)(OR^{17}OR^{18})$ is —$C(Me)_2P({=}O)(OMe)_2$ or —$CH_2$—$P({=}O)(OMe)_2$;

(8) $R^{19}$ is F, O═ or methyl; and (9) one or two of $R^3$, $R^4$ and $R^5$; $R^6$; and $R^7$ are deuterium or a deuterated group.

5. The compound represented by formula I or the pharmaceutically acceptable salt thereof according to claim 1, wherein, the compound satisfies any one of the following conditions:

(1)

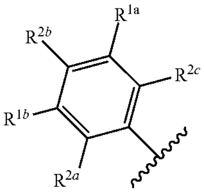 is 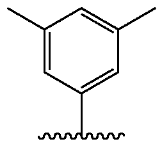,

-continued
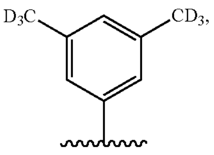 or 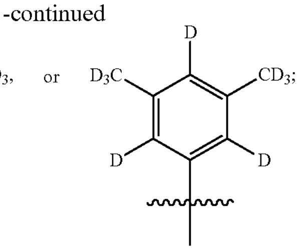
(2)
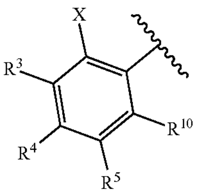 is 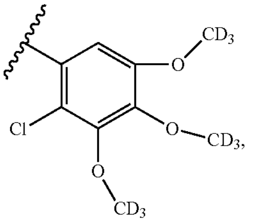
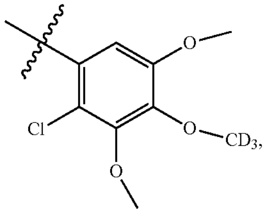 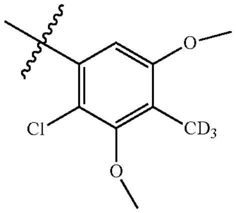 ,
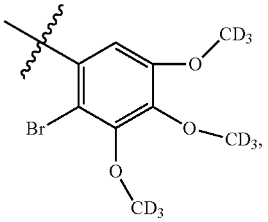 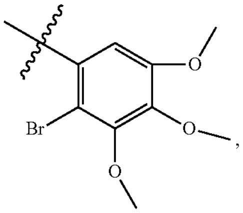 or
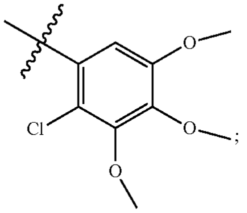 and
(3)
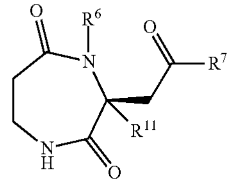 is 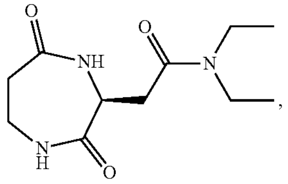
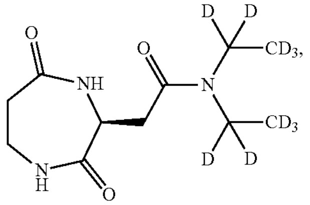 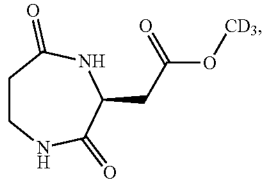
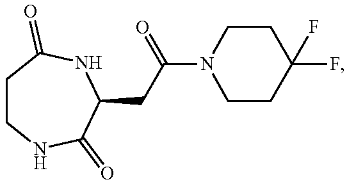
-continued
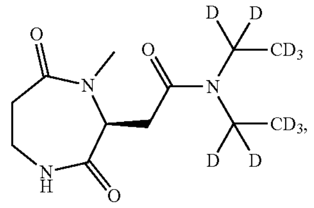 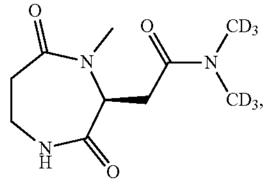
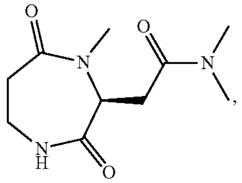
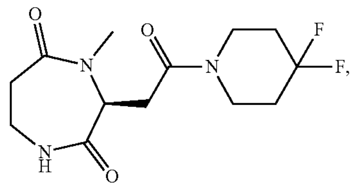
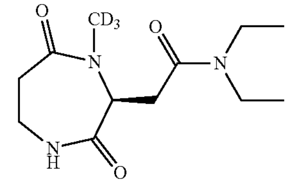 ,
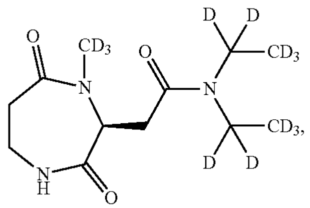 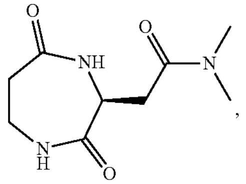
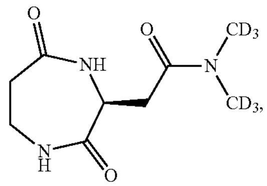
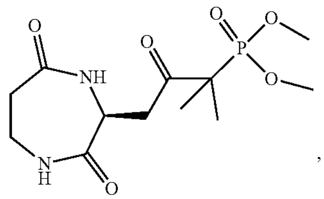 ,
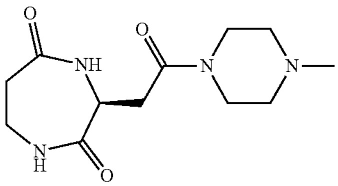 ,
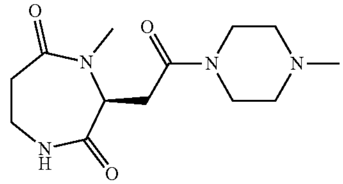 , -continued

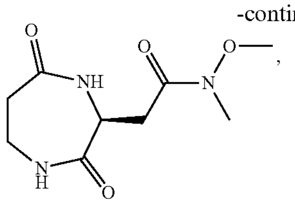,

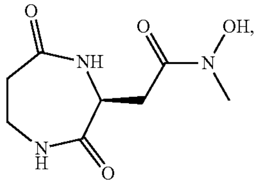

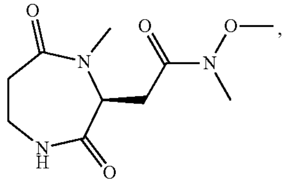,

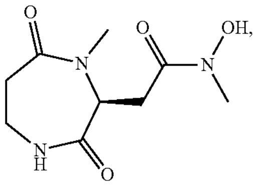

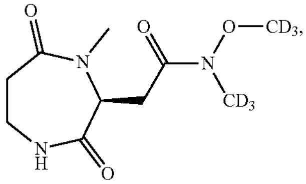,

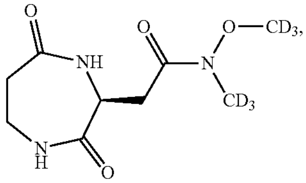,

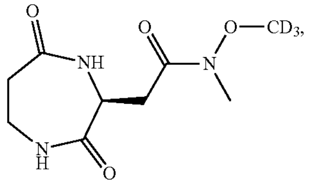 or

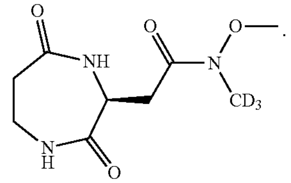.

6. The compound represented by formula I or the pharmaceutically acceptable salt thereof according to claim 1, wherein, the compound represented by formula I is of the following Scheme 1, Scheme 2, Scheme 4, Scheme 4, Scheme 5, or Scheme 6;

Scheme 1, wherein, X is chlorine or bromine;

$R^{1a}$ and $R^{1b}$ are independently $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl or deuterated $C_{1-3}$ alkyl;

$R^7$ is —$OR^{12}$, —$NR^{13}R^{14}$ or —$C(R^{15}R^{16})$—P(═O)($OR^{17}OR^{18}$);

$R^{12}$ is deuterated $C_{1-3}$ alkyl;

$R^{15}$ and $R^{16}$ are independently $C_{1-3}$ alkyl;

$R^{17}$ and $R^{18}$ are independently $C_{1-3}$ alkyl;

$R^{13}$ is OH, $C_{1-3}$ alkyl, deuterated $C_{1-3}$ alkyl, $C_{1-3}$ alkyl-O— or deuterated $C_{1-3}$ alkyl-O—;

$R^{14}$ is $C_{1-3}$ alkyl or deuterated $C_{1-3}$ alkyl;

or, $R^{13}$ and $R^{14}$ together with the attached nitrogen atom form: a 4- to 6-membered aliphatic heterocycle or a 4- to 6-membered aliphatic heterocycle substituted by one or more $R^{19}$;

$R^{19}$ is halogen, O═, $C_{1-3}$ alkyl or deuterated $C_{1-3}$ alkyl;

$R^8$, $R^9$, $R^{10}$ and $R^{11}$ are hydrogen;

wherein, at least one of $R^{1a}$, $R^{1b}$, $R^3$, $R^4$, $R^5$, $R^6$ and $R^7$ is deuterium or a deuterated group;

Scheme 2, wherein, X is chlorine or bromine;

$R^{1a}$ and $R^{1b}$ are independently $C_{1-3}$ alkyl; and $R^{1a}$ and $R^{1b}$ are the same;

$R^{2a}$, $R^{2b}$ and $R^{2c}$ are independently hydrogen; and $R^{2a}$, $R^{2b}$ and $R^{2c}$ are the same;

$R^3$, $R^4$ and $R^5$ are independently $C_{1-3}$ alkyl-O— or deuterated $C_{1-3}$ alkyl-O—; and $R^3$, $R^4$ and $R^5$ are the same;

$R^6$ is H; $R^7$ is —$OR^{12}$, —$NR^{13}R^{14}$, or —$C(R^{15}R^{16})$—P(═O)($OR^{17}OR^{18}$); wherein $R^{12}$ is independently deuterated $C_{1-3}$ alkyl; $R^{15}$ and $R^{16}$ are independently $C_{1-3}$ alkyl; $R^{17}$ and $R^{18}$ are independently $C_{1-3}$ alkyl; $R^{13}$ is methyl, deuterated $C_{1-3}$ alkyl, $C_{1-3}$ alkyl-O— or deuterated $C_{1-3}$ alkyl-O—; $R^{14}$ is methyl or deuterated $C_{1-3}$ alkyl; or, $R^{13}$ and $R^{14}$ together with the attached nitrogen atom form: a 4- to 6-membered aliphatic heterocycle or a 4- to 6-membered aliphatic heterocycle substituted by one or more $R^{19}$; $R^{15}$, $R^{16}$, $R^{17}$ and $R^{18}$ are independently $C_{1-3}$ alkyl; $R^{19}$ is halogen;

or, $R^6$ is $C_{1-3}$ alkyl; $R^7$ is —$NR^{13}R^{14}$, $R^{13}$ is OH, $C_{1-3}$ alkyl, deuterated $C_{1-3}$ alkyl or deuterated $C_{1-3}$ alkyl-O—; $R^{14}$ is $C_{1-3}$ alkyl or deuterated $C_{1-3}$ alkyl;

$R^8$, $R^9$, $R^{10}$ and $R^{11}$ are hydrogen;

wherein, at least one of $R^3$, $R^4$, $R^5$, $R^6$ and $R^7$ is deuterium or a deuterated group;

Scheme 3,

X is hydrogen, fluorine, chlorine, bromine or iodine;

$R^{1a}$ and $R^{1b}$ are independently $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl, $C_{2-4}$ alkynyl or deuterated $C_{1-3}$ alkyl;

$R^7$ is —$OR^{12}$, —$NR^{13}R^{14}$ or —$C(R^{15}R^{16})$—P(═O)($OR^{17}OR^{18}$), wherein $R^{12}$, $R^{17}$ and $R^{18}$ are independently $C_{1-3}$ alkyl or deuterated $C_{1-3}$ alkyl; $R^{15}$ and $R^{16}$ are independently H, $C_{1-3}$ alkyl or deuterated $C_{1-3}$ alkyl;

$R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—; or, $R^{13}$ and $R^{14}$ together with the attached nitrogen atom form: a 4- to 6-membered aliphatic heterocycle or a 4- to 6-membered aliphatic heterocycle substituted by one or more $R^{19}$; $R^{19}$ is halogen, O═, $C_{1-3}$ alkyl or deuterated $C_{1-3}$ alkyl;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group;

Scheme 4,

X is hydrogen, fluorine, chlorine, bromine or iodine;

$R^{1a}$ and $R^{1b}$ are independently $C_{1-3}$ alkyl or deuterated $C_{1-3}$ alkyl;

$R^{2a}$, $R^{2b}$ and $R^{2c}$ are independently hydrogen or deuterium;

$R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—;

$R^6$ is H, $C_{1-3}$ alkyl,

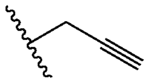 [SMILES: *CC#C]

or deuterated $C_{1-3}$ alkyl;

$R^7$ is —$OR^{12}$, —$NR^{13}R^{14}$ or —$C(R^{15}R^{16})$—$P(=O)(OR^{17}OR^{18})$, wherein $R^{12}$, $R^{17}$ and $R^{18}$ are independently $C_{1-3}$ alkyl or deuterated $C_{1-3}$ alkyl; $R^{15}$ and $R^{16}$ are independently H, $C_{1-3}$ alkyl or deuterated $C_{1-3}$ alkyl;

$R^{13}$ and $R^{14}$ are independently OH, $C_{1-3}$ alkyl, deuterated $C_{1-3}$ alkyl, $C_{1-3}$ alkyl-O— or deuterated $C_{1-3}$ alkyl-O—; or, $R^{13}$ and $R^{14}$ together with the attached nitrogen atom form: a 4- to 6-membered aliphatic heterocycle or a 4- to 6-membered aliphatic heterocycle substituted by one or more $R^{19}$;

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group;

Scheme 5,

X is fluorine, chlorine or bromine;

$R^{1a}$ and $R^{1b}$ are independently methyl or deuterated methyl;

$R^{2a}$, $R^{2b}$ and $R^{2c}$ are independently hydrogen or deuterium;

$R^3$, $R^4$ and $R^5$ are independently methyl, methyl-O—, $CD_3$ or $CD_3$-O—;

$R^6$ is H, methyl,

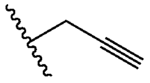 [SMILES: *CC#C]

or $CD_3$;

$R^7$ is —$OR^{12}$, —$NR^{13}R^{14}$ or —$C(R^{15}R^{16})$—$P(=O)(OR^{17}OR^{18})$, wherein $R^{12}$, $R^{17}$ and $R^{18}$ are independently methyl, ethyl, $CD_3$ or —$CD_2$-$CD_3$;

$R^{15}$ and $R^{16}$ are independently methyl, ethyl, $CD_3$ or —$CD_2$-$CD_3$;

$R^{13}$ and $R^{14}$ are independently OH, methyl, ethyl, $CD_3$, —$CD_2$-$CD_3$ or $CD_3$-O—, or, $R^{13}$ and $R^{14}$ together with the attached nitrogen atom form:

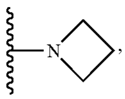,
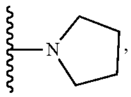,
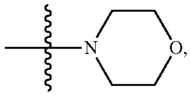

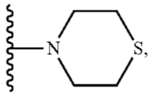
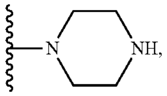
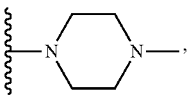

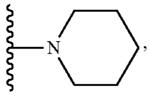,
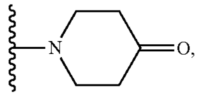

-continued

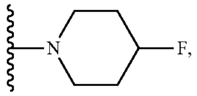
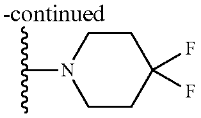 or

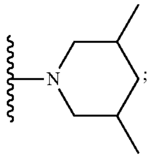

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$, $R^7$, $R^8$, $R^9$, $R^{10}$ and $R^{11}$ is deuterium or a deuterated group; or Scheme 6, X is chlorine or bromine;

$R^{1a}$ and $R^{1b}$ are independently methyl or $CD_3$;

$R^{2a}$, $R^{2b}$ and $R^{2c}$ are independently hydrogen or deuterium;

$R^3$, $R^4$ and $R^5$ are independently methyl, methyl-O—, $CD_3$ or $CD_3$-O—;

$R^6$ is H, methyl, or $CD_3$;

$R^7$ is —$OR^{12}$, —$NR^{13}R^{14}$ or —$C(R^{15}R^{16})$—$P(=O)(OR^{17}OR^{18})$, wherein $R^{12}$, $R^{17}$ and $R^{18}$ are independently methyl, ethyl, $CD_3$ or —$CD_2$-$CD_3$;

$R^{15}$ and $R^{16}$ are independently methyl;

$R^{13}$ and $R^{14}$ are independently methyl, ethyl, methyl-O—, $CD_3$, —$CD_2$-$CD_3$ or $CD_3$-O—;

or, $R^{13}$ and $R^{14}$ together with the attached nitrogen atom form:

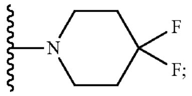 [SMILES: *N1CCC(F)(F)CC1]

$R^8$, $R^9$, $R^{10}$ and $R^{11}$ are independently hydrogen or deuterium;

wherein, at least one of $R^{1a}$, $R^{1b}$, $R^3$, $R^4$, $R^5$, $R^6$ and $R^7$ is deuterium or a deuterated group.

7. The compound represented by formula I or the pharmaceutically acceptable salt thereof according to claim 1, wherein, the compound represented by formula I or the pharmaceutically acceptable salt thereof is selected from the following compounds, Compound 1

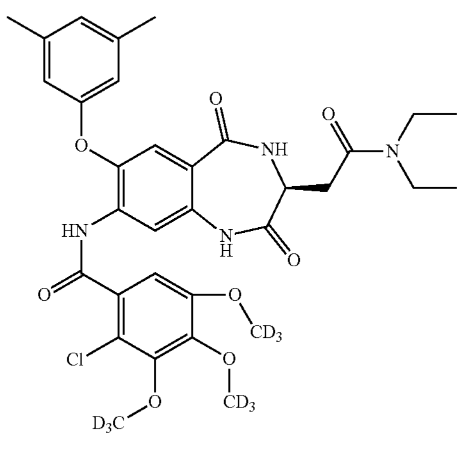

-continued
Compound 2
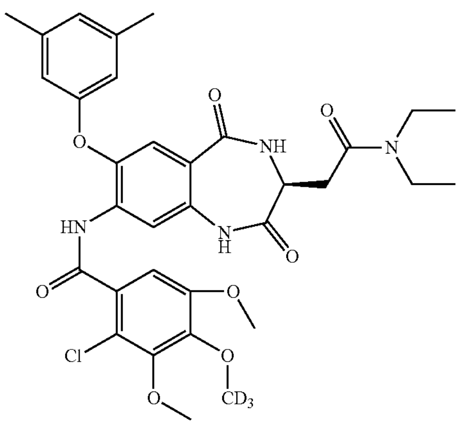
Compound 3
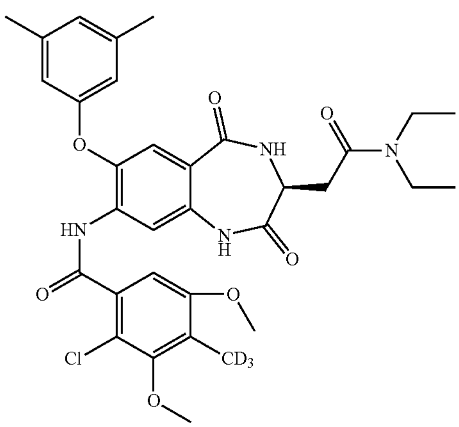
Compound 4
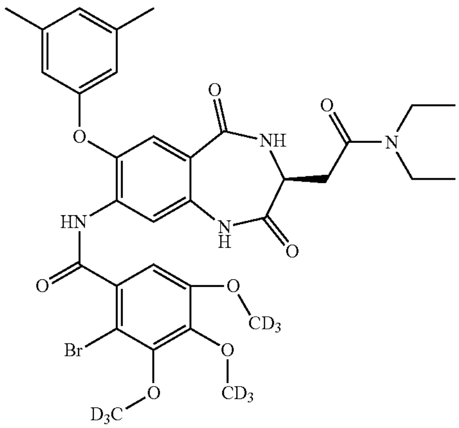
-continued
Compound 5
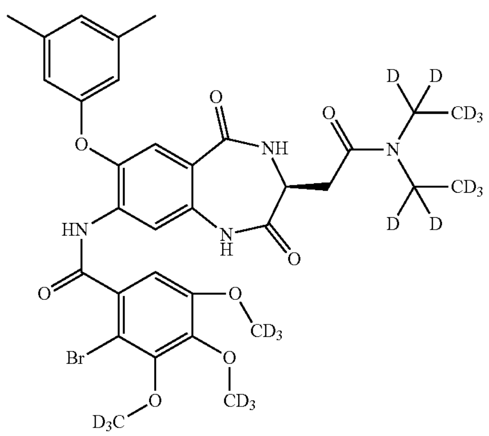
Compound 6
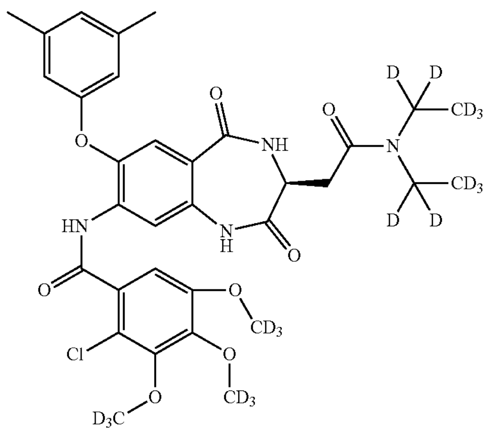
Compound 7
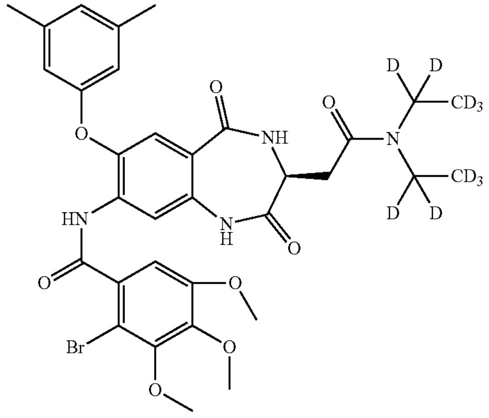

-continued
Compound 8
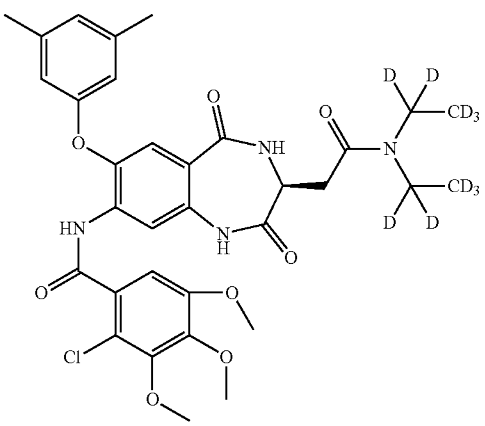
Compound 9
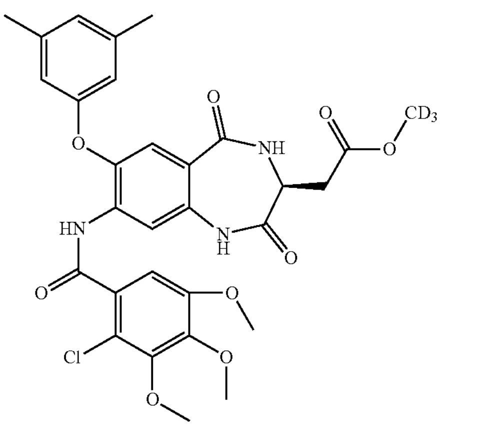
Compound 10
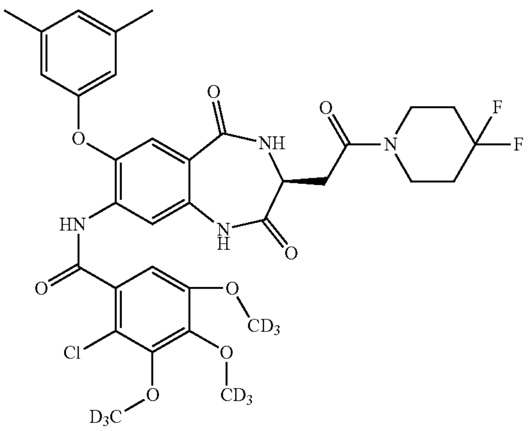
-continued
Compound 11
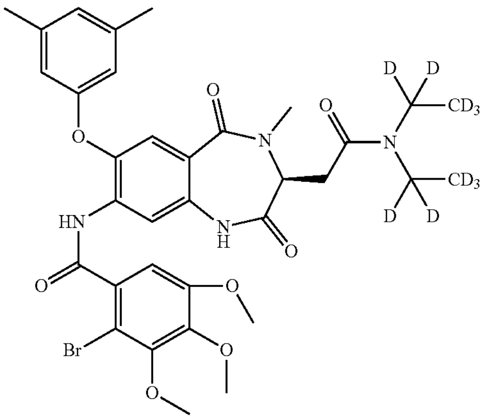
Compound 12
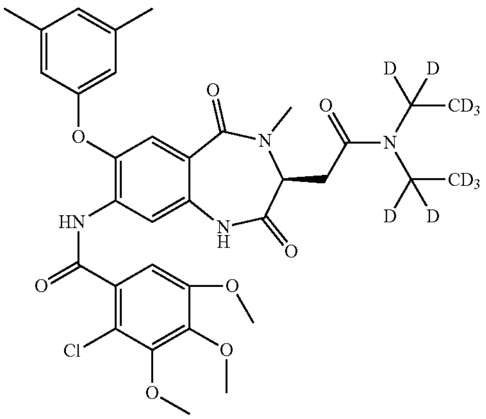
Compound 13
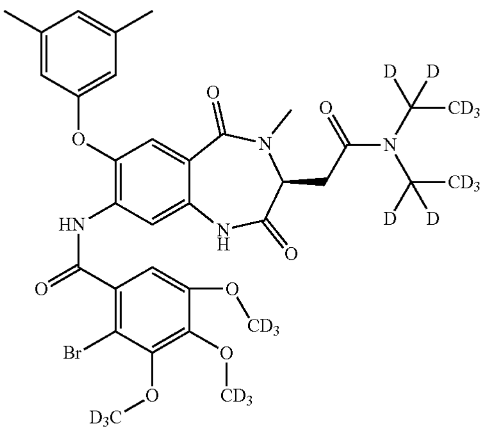

-continued
Compound 14
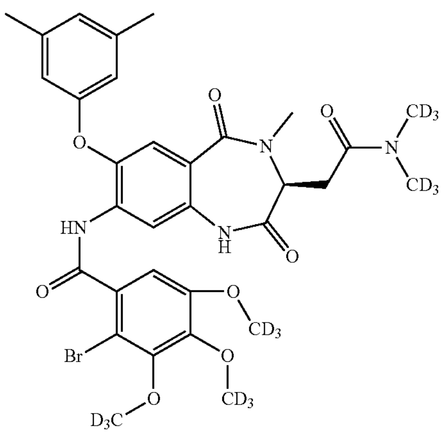
Compound 15
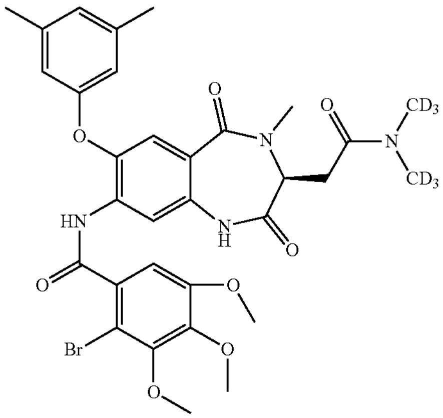
Compound 16
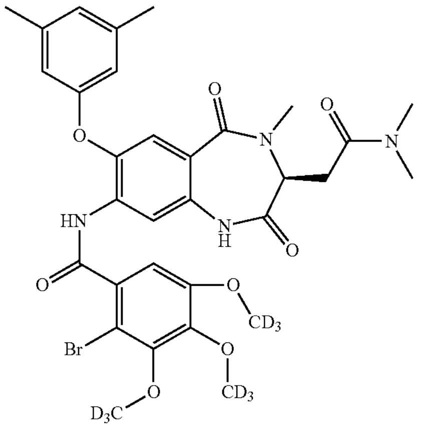
-continued
Compound 17
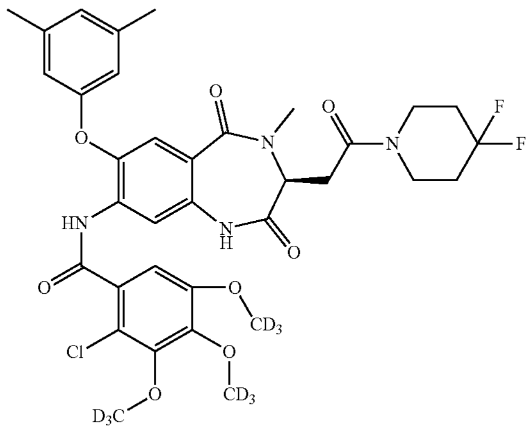
Compound 18
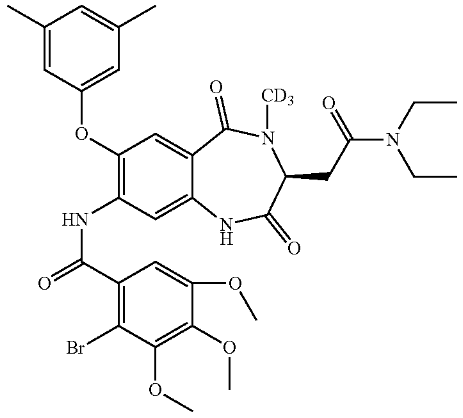
Compound 19
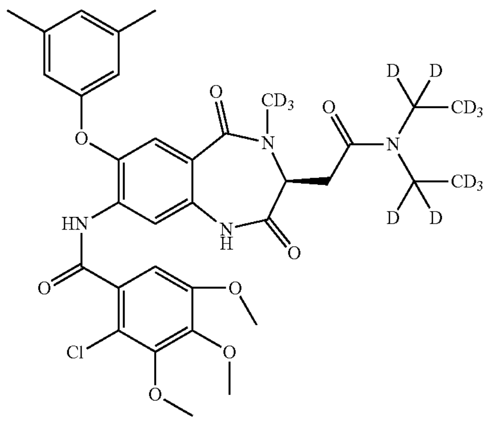

-continued
Compound 20
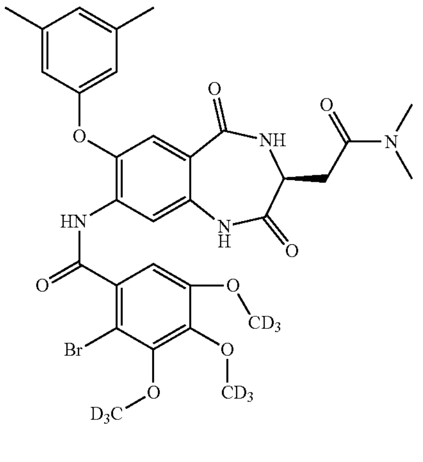
Compound 21
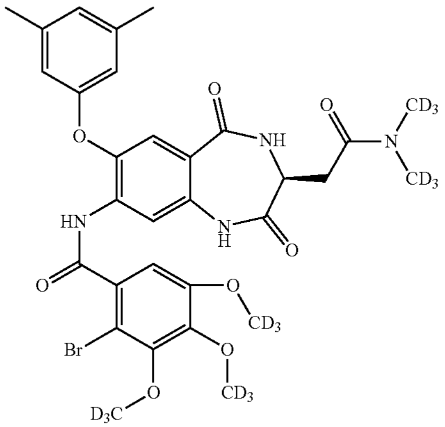
Compound 22
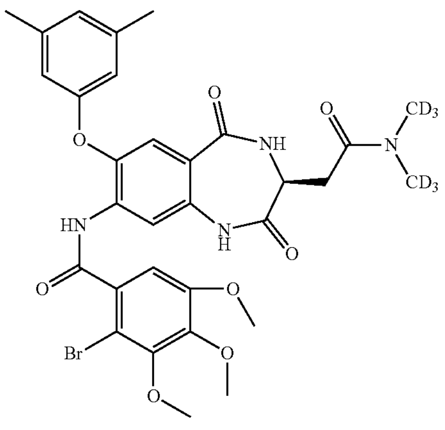
-continued
Compound 23
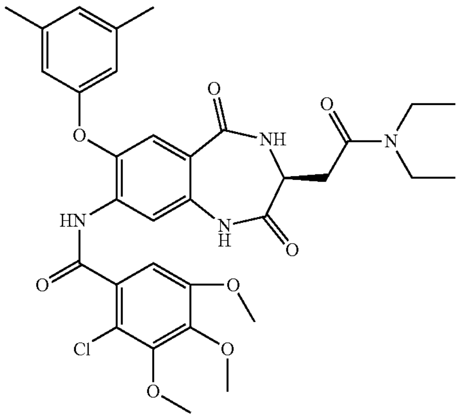
Compoung 25
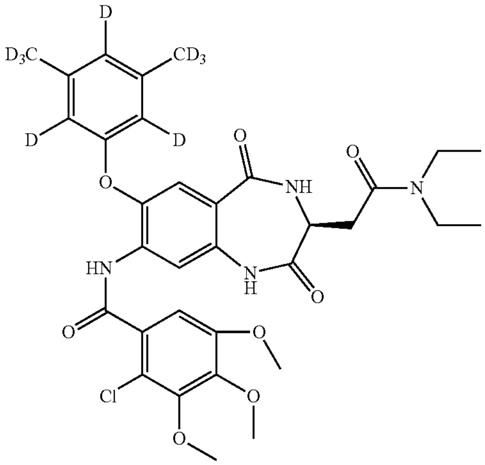
Compound 26
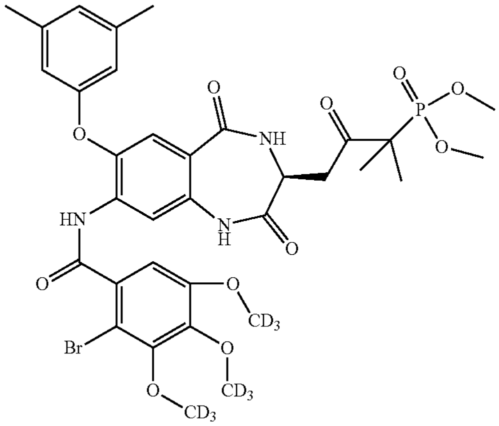

-continued
Compound 27
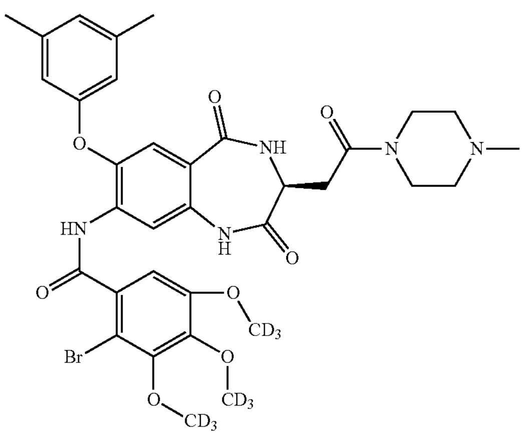
HCl
Compound 28
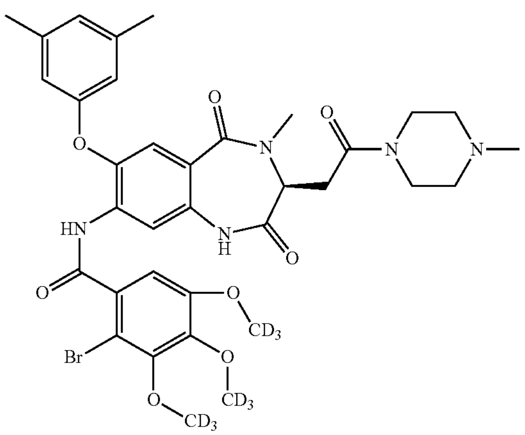
Compound 29
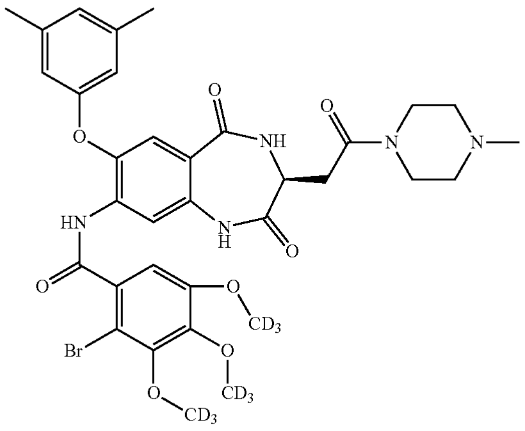
-continued
Compound 30
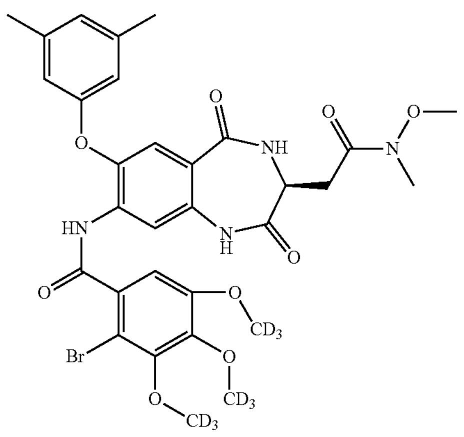
Compound 31
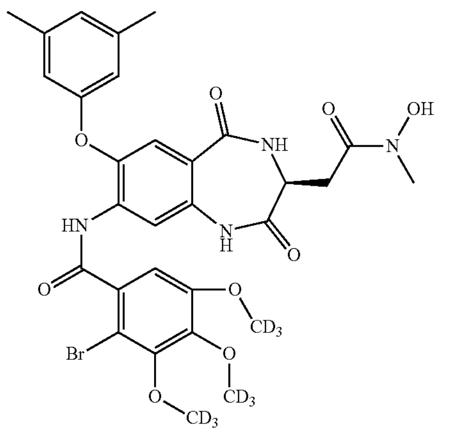
Compound 32
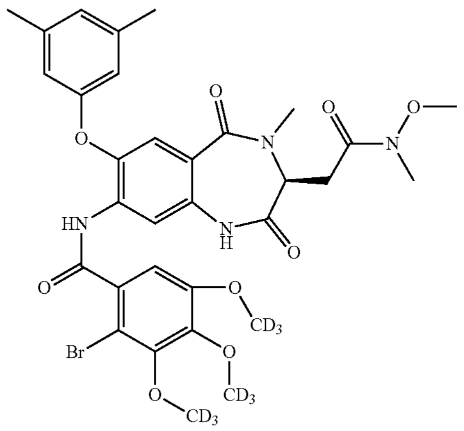

-continued
Compoound 33
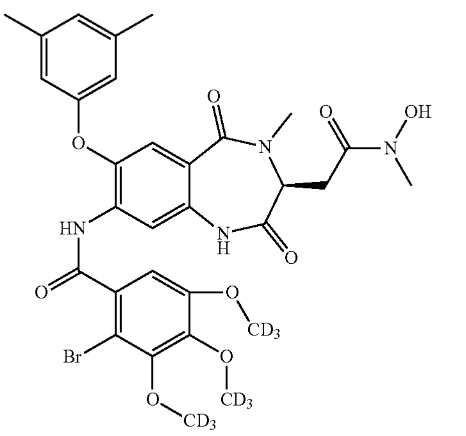
Compound 34
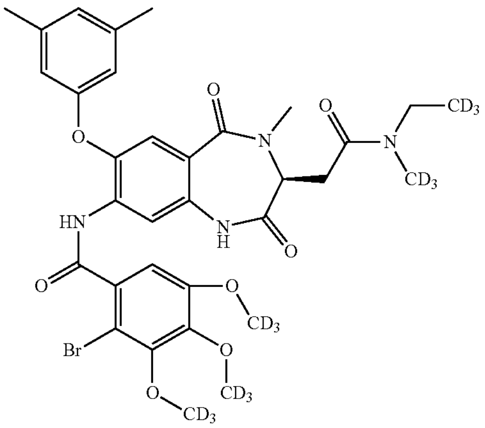
Compound 35
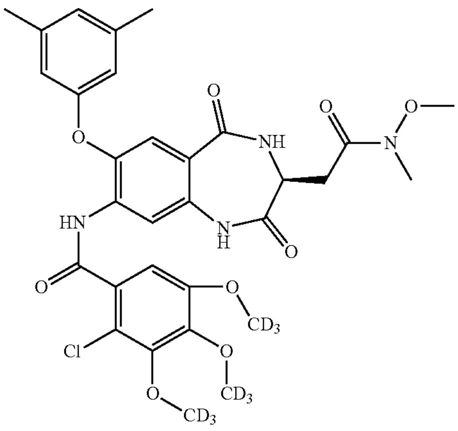
-continued
Compound 36
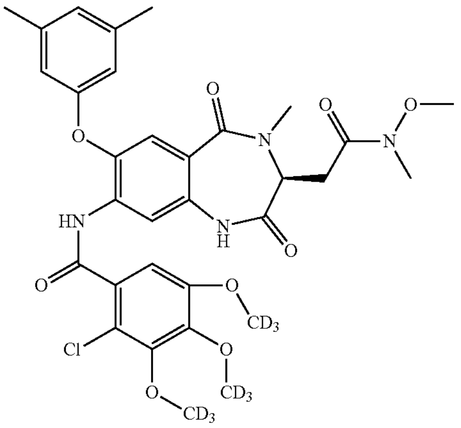
Compound 37
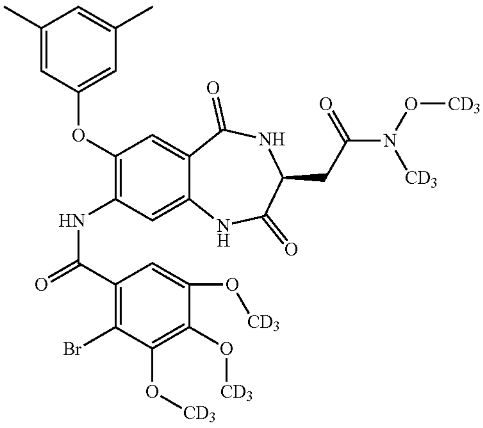
Compound 38
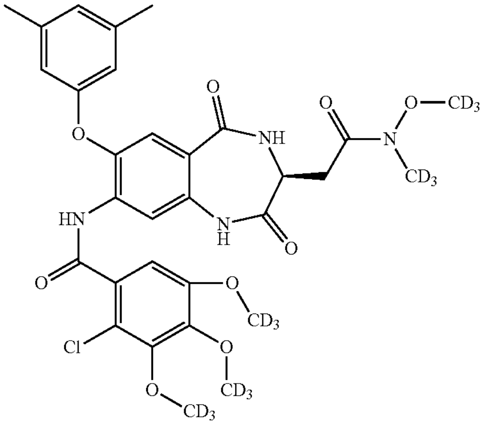

-continued

Compound 39

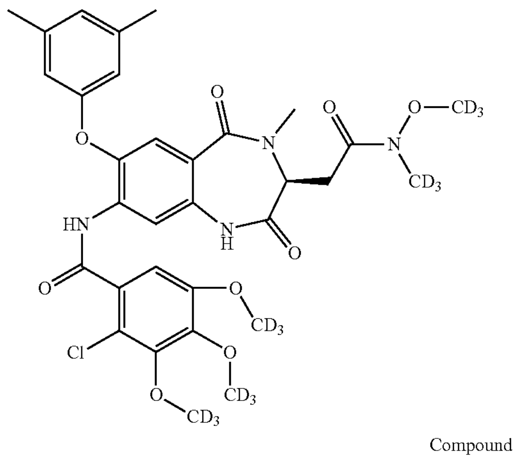

Compound 40

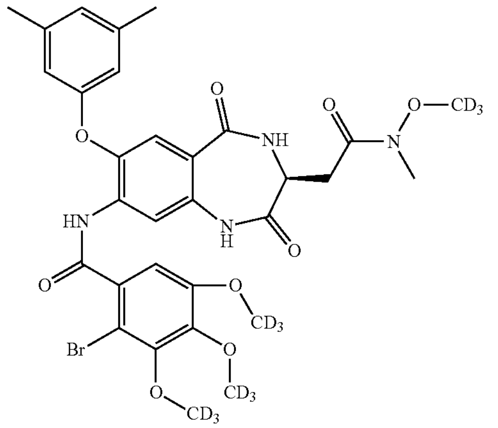

Compound 41

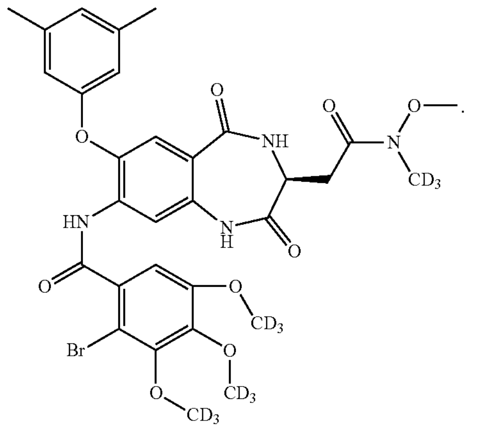

8. A pharmaceutical composition, which comprises the compound represented by formula I or the pharmaceutically acceptable salt thereof according to claim 1, and a pharmaceutically acceptable carrier, wherein the dosage of the compound represented by formula I or the pharmaceutically acceptable salt thereof is a therapeutically effective amount.

9. A method for treating a proliferative disease, comprising:

administering the compound represented by formula I or the pharmaceutically acceptable salt thereof according to claim 1 to the subject.

10. The compound represented by formula I or the pharmaceutically acceptable salt thereof according to claim 3, wherein, the compound satisfies any one of the following conditions:

(1) when $R^{1a}$ and $R^{1b}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl is methyl;

(2) when $R^3$, $R^4$ and $R^5$ are independently $C_{1-3}$ alkyl, $C_{1-3}$ alkyl-O—, deuterated $C_{1-3}$ alkyl or deuterated $C_{1-3}$ alkyl-O—, the $C_{1-3}$ alkyl in the $C_{1-3}$ alkyl, $C_{1-3}$ alkyl-O—, deuterated $C_{1-3}$ alkyl and deuterated $C_{1-3}$ alkyl-O— is methyl;

(3) when Re is $C_{1-3}$ alkyl or deuterated $C_{1-3}$ alkyl, the $C_{1-3}$ alkyl in the $C_{1-3}$ alkyl and the deuterated $C_{1-3}$ alkyl is methyl;

(4) when $R^{12}$, $R^{17}$ and $R^{18}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl is methyl;

(5) when $R^{15}$ and $R^{16}$ are independently $C_{1-3}$ alkyl or deuterated $C_{1-3}$ alkyl, the $C_{1-3}$ alkyl in the $C_{1-3}$ alkyl and the deuterated $C_{1-3}$ alkyl are methyl or ethyl;

(6) when $R^{13}$ and $R^{14}$ are independently $C_{1-3}$ alkyl, deuterated $C_{1-3}$ alkyl, $C_{1-3}$ alkyl-O— or deuterated $C_{1-3}$ alkyl-O—, the $C_{1-3}$ alkyl in the $C_{1-3}$ alkyl, deuterated $C_{1-3}$ alkyl, $C_{1-3}$ alkyl-O— or deuterated $C_{1-3}$ alkyl-O— is methyl or ethyl;

(7) when $R^{13}$ and $R^{14}$ together with the attached nitrogen atom form: a 4- to 6-membered aliphatic heterocycle or a 4-6-membered aliphatic heterocycle substituted by one or more $R^{19}$, the 4- to 6-membered aliphatic heterocycle in the 4- to 6-membered aliphatic heterocycle and the 4- to 6-membered aliphatic heterocycle substituted by one or more $R^{19}$ is 6-membered heterocyclic alkyl, wherein containing 0-1 heteroatoms selected from N, O or S, besides the 1 N attached to the shown carbonyl;

(8) when $R^{19}$ is halogen, the halogen is fluorine or chlorine; and (9) when $R^{19}$ is $C_{1-3}$ alkyl or deuterated $C_{1-3}$ alkyl, the $C_{1-3}$ alkyl in the $C_{1-3}$ alkyl and the deuterated $C_{1-3}$ alkyl is methyl.

11. The compound represented by formula I or the pharmaceutically acceptable salt thereof according to claim 3, wherein, the compound satisfies any one of the following conditions:

(1) when $R^{19}$ is halogen, the halogen is fluorine; and (2) when $R^{13}$ and $R^{14}$ together with the attached nitrogen atom form: a 4- to 6-membered aliphatic heterocycle or a 4-6-membered aliphatic heterocycle substituted by one or more $R^{19}$, the 4- to 6-membered aliphatic heterocycle in the 4- to 6-membered aliphatic heterocycle and the 4- to 6-membered aliphatic heterocycle substituted by one or more $R^{19}$ is 4- to 6-membered heterocyclic alkyl, wherein containing 0-1 heteroatoms selected from N, O or S, besides the 1 N attached to the shown carbonyl; the 4- to 6-membered heterocyclic alkyl is

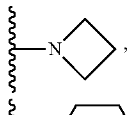, 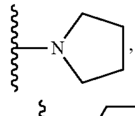, 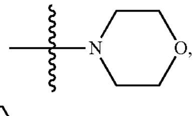

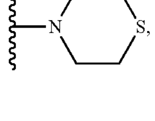, 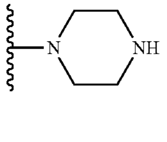 or

-continued

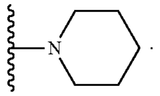

12. The compound represented by formula I or the pharmaceutically acceptable salt thereof according to claim 10, wherein, when $R^{13}$ and $R^{14}$ together with the attached nitrogen atom form: a 4- to 6-membered aliphatic heterocycle or a 4-6-membered aliphatic heterocycle substituted by one or more $R^{19}$, the 4- to 6-membered aliphatic heterocycle in the 4- to 6-membered aliphatic heterocycle and the 4- to 6-membered aliphatic heterocycle substituted by one or more $R^{19}$ is 6-membered heterocyclic alkyl; the 6-membered heterocyclic alkyl is

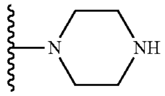

or

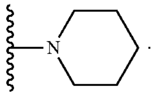

13. The compound represented by formula I or the pharmaceutically acceptable salt thereof according to claim 6, wherein, in Scheme 6, $R^{12}$, $R^{17}$ and $R^{18}$ are independently methyl or $CD_3$.

14. The method according to claim 9, wherein, the proliferative disease is selected from cancer, lymphatic hematopoietic system tumor, marrow hematopoietic system tumor, interstitial tumor, teratoma, and glioma.

15. The method according to claim 14, wherein, the method satisfies any one of the following conditions:

(1) the cancer is selected from bladder cancer, brain cancer, breast cancer, colon cancer, rectal cancer, renal cancer, liver cancer, lung cancer, ovarian cancer, pancreatic cancer, adrenal cancer, prostate cancer, stomach cancer, vaginal cancer, cervical cancer, endometrial cancer, central nervous system tumor, melanoma, seminoma, neuroblastoma, leukemia, thyroid cancer and skin cancer;

(2) the lymphatic hematopoietic system tumor is selected from acute lymphoblastic leukemia, B-cell lymphoma and Burketts lymphoma;

(3) the marrow hematopoietic system tumor is selected from acute and chronic myeloid leukemia and promyelocytic leukemia; and (4) the interstitial tumor is selected from fibrosarcoma and rhabdomyosarcoma.

16. The method according to claim 15, wherein a cell of the lung cancer is A549 non-small cell lung cancer cell; a cell of the colon cancer is HCT116 colon cancer cell; a cell of the central nervous system tumor is SF295 central nervous system tumor cell; a cell of the melanoma is LOX-IMVI melanoma cell; a cell of the renal cancer is 786-0 renal cancer cell; a cell of the leukemia is K562 leukemia cell; a cell of the prostate cancer is PC-3 prostate cancer cell; a cell of the ovarian cancer is OVCAR-3 ovarian cancer cell; a cell of the breast cancer is HS 578T breast cancer cell.

* * * * *